US010450593B2

(12) United States Patent
Gonzalez et al.

(10) Patent No.: US 10,450,593 B2
(45) Date of Patent: Oct. 22, 2019

(54) TYPE II FATTY ACID SYNTHESIS ENZYMES IN REVERSE β-OXIDATION

(71) Applicant: William Marsh Rice University, Houston, TX (US)

(72) Inventors: Ramon Gonzalez, Houston, TX (US); James M. Clomburg, Houston, TX (US); Jacob E. Vick, Houston, TX (US)

(73) Assignee: William Marsh Rice University, Houston, TX (US)

( * ) Notice: Subject to any disclaimer, the term of this patent is extended or adjusted under 35 U.S.C. 154(b) by 110 days.

(21) Appl. No.: 15/114,502

(22) PCT Filed: Jan. 26, 2015

(86) PCT No.: PCT/US2015/012932
§ 371 (c)(1),
(2) Date: Jul. 27, 2016

(87) PCT Pub. No.: WO2015/112988
PCT Pub. Date: Jul. 30, 2015

(65) Prior Publication Data
US 2016/0340699 A1 Nov. 24, 2016

Related U.S. Application Data

(60) Provisional application No. 61/932,057, filed on Jan. 27, 2014.

(51) Int. Cl.
*C12P 7/64* (2006.01)
*C12N 15/52* (2006.01)
*C12N 9/00* (2006.01)
*C10L 1/02* (2006.01)
*C10L 1/04* (2006.01)
*C12N 9/10* (2006.01)
*C12N 9/04* (2006.01)
*C12N 9/02* (2006.01)
*C12N 9/88* (2006.01)

(52) U.S. Cl.
CPC .......... *C12P 7/64* (2013.01); *C10L 1/02* (2013.01); *C10L 1/04* (2013.01); *C12N 9/00* (2013.01); *C12N 9/001* (2013.01); *C12N 9/0006* (2013.01); *C12N 9/0008* (2013.01); *C12N 9/0071* (2013.01); *C12N 9/1029* (2013.01); *C12N 9/1096* (2013.01); *C12N 9/88* (2013.01); *C12N 15/52* (2013.01); *C12Y 101/011* (2013.01); *C12Y 101/03013* (2013.01); *C12Y 102/01* (2013.01); *C12Y 102/01003* (2013.01); *C12Y 103/01009* (2013.01); *C12Y 114/00* (2013.01); *C12Y 203/01009* (2013.01); *C12Y 206/00* (2013.01); *C12Y 401/99005* (2013.01); *C12Y 402/01059* (2013.01); *Y02E 50/343* (2013.01)

(58) Field of Classification Search
None
See application file for complete search history.

(56) References Cited

U.S. PATENT DOCUMENTS

2013/0316413 A1* 11/2013 Gonzalez ............... C12P 5/026
435/146

FOREIGN PATENT DOCUMENTS

| EP | 2673369 | 4/2017 | |
| WO | WO 2013/036812 | * 3/2013 | ............... C12N 7/00 |
| WO | 2015191422 | 12/2015 | |

OTHER PUBLICATIONS

Yan R.T. & Chen J.S. (1990( Coenzyme A—acylating aldehyde dehydrogenase from Clostridium beijerinckii NRRL B592. Appl. Environ. Microbiol. 56, 2591-2599.
Zhu L., et al. (2013) The Two Functional Enoyl-Acyl Carrier Protein Reductases of Enterococcus faecalis Do Not Mediate Triclosan Resistance. MBio 4:10.
Atsumi, S., Cann, A. F., Connor, M. R., Shen, C. R., Smith, K. M., Brynildsen, M. P., . . . Liao, J. C. (2008). Metabolic engineering of *Escherichia coli* for 1-butanol production. Metabolic engineering, 10(6), 305-11.
Baba, T., Ara, T., Hasegawa, M., Takai, Y., Okumura, Y., Baba, M., . . . Mori, H. (2006). Construction of *Escherichia coli* K-12 in-frame, single-gene knockout mutants: the Keio collection. Molecular systems biology, 2, 2006.
Bergler, H., et al., (1994) Protein EnvM Is the NADH-dependent Enoyl-ACP Reductase (FabI) of *Escherichia coli*. The Journal of biological chemistry, 269(8), 5493-5496.
Bergler, H. et al., (1996) which catalyzes a key regulatory step in fatty acid biosynthesis , accepts NADH and NADPH as cofactors and is inhibited by palmitoyl-CoA, 694, 689-694.
Bi H.K., et al., (2014) Inefficient Translation Renders the Enterococcus faecalis fabK Enoyl-Acyl Carrier Protein Reductase Phenotypically Cryptic. J. Bacteriol. 196:170-179.
Binstock J.F. & Schulz H. (1981) Fatty acid oxidation complex from *Escherichia coli*. Methods Enzymol. 71 Pt C:403-411.

(Continued)

*Primary Examiner* — Nancy A Treptow
(74) *Attorney, Agent, or Firm* — Boulware & Valoir

(57) ABSTRACT

This disclosure describes enzymes from the type II (a discrete set of enzymes) fatty acid synthesis ("FAS") pathway that can be used in combination with thiolases to operate a functional reversal of the β-oxidation cycle. A combination of thiolases with one or more of 3-oxoacyl-[acyl-carrier-protein] reductase (FabG, others), 3-hydroxyacyl-[acp] dehydratase (FabA, FabZ, others), and enoyl-[acyl-carrier-protein] reductase (FabI, FabK, FabL, FabV, others) yields a functional reversal of the β-oxidation cycle. If only one or two enzymes are used, the remaining enzymes will be traditional beta oxidation enzymes. Once this cycle is coupled with the appropriate priming and termination pathways, the production of carboxylic acids, alcohols, hydrocarbons, amines and their α-, β-, and ω-functionalized derivatives from renewable carbon sources can be achieved.

45 Claims, 18 Drawing Sheets

(56) References Cited

OTHER PUBLICATIONS

Bond-Watts, B.B., et al., (2011a) Enzyme mechanism as a kinetic control element for designing synthetic biofuel pathways. Nature chemical biology, 7(4), 222-7. doi:10.1038/nchembio.537.

Campbell, J.W. & Jr, J.E.C. (2002) The Enigmatic *Escherichia coli* fadE Gene Is yafH, 184(13), 3759-3764.

Campbell, J.W., et al., (2003) A new *Escherichia coli* metabolic competency: growth on fatty acids by a novel anaerobic beta-oxidation pathway. Molecular microbiology, 47(3), 793-805.

Cheng, Q., Tet al., (2000) Genetic analysis of a gene cluster for cyclohexanol oxidation in *Acinetobacter* sp strain SE19 by in vitro transposition. J. Bacteriol. 182, 4744-4751.

Choi, Y.J., et al., (2010) Novel, versatile, and tightly regulated expression system for *Escherichia coli* strains. Applied and environmental microbiology, 76(15), 5058-66.

Clomburg J.M., et al., (2012) A Synthetic Biology Approach to Engineer a Functional Reversal of the β-Oxidation Cycle. ACS Synth. Biol. 1:541-554.

Datsenko, K.A. & Wanner, B.L. (2000) One-step inactivation of chromosomal genes in *Escherichia coli* K-12 using PCR products. Proceedings of the National Academy of Sciences of the United States of America, 97(12), 6640-5.

Dellomonaco, C., et al., (2011) Engineered reversal of the β-oxidation cycle for the synthesis of fuels and chemicals. Nature, 476(7360), 355-359.

Elssner, T., et al., (2000) Isolation, identification, and synthesis of gamma-butyrobetainyl-CoA and crotonobetainyl-CoA, compounds involved in carnitine metabolism of *E. coli*. Biochemistry, 39(35), 10761-9.

Harwood C.S., et al., (1994) Identification of the pcaRKF gene cluster from Pseudomonas putida: involvement in chemotaxis, biodegradation, and transport of 4-hydroxybenzoate. J. Bacteriol. 176, 6479-6488.

Heath, R.J. & Rock, C.O. (1995) Enoyl-Acyl Carrier Protein Reductase (fabI) Plays a Determinant Role in Completing Cycles of Fatty Acid Elongation in *Escherichia coli*. Journal of Biological Chemistry, 270(44), 26538-26542.

Heath R.J., et al., (2000) the enoyl-acyl-carrier-protein reductases FabI and FabL from Bacillus subtilis. J. Biol. Chem. 275:40128-40133.

Ishihama, Y., et al., (2008) Protein abundance profiling of the *Escherichia coli* cytosol. BMC genomics, 9, 102.

Ismail W., et al., (2003) Functional genomics by NMR spectroscopy. Phenylacetate catabolism in *Escherichia coli*. Eur. J. Biochem. 270, 3047-3054.

Jenkins L.S. & Nunn W.D. (1987) Genetic and molecular characterization of the genes involved in short-chain fatty-acid degradation in *Escherichia coli*: The ato system. J. Bacteriol. 169:42-52.

Julsing, M.K., et al., (2012) Outer Membrane Protein AlkL Boosts Biocatalytic Oxyfunctionalization of Hydrophobic Substrates in *Escherichia coli*. Appl. Environ. Microbiol. 78, 5724-5733.

Kang, Y., et al., (2004) Systematic mutagenesis of the *Escherichia coli* genome. Journal of bacteriology, 186, 4921-4930.

Kim, E.J., et al., (2014) Crystal structure and biochemical characterization of β-keto thiolase B from bolyhydroxyalkanoate-producing bacterium Ralstonia eutropha H16. Biochem. Biophys. Res. Commun. 444, 365-369.

Kitagawa, M., et al., (2005) Complete set of ORF clones of *Escherichia coli* ASKA library (a complete set of *E. coli* K-12 ORF archive): unique resources for biological research. DNA research: an international journal for rapid publication of reports on genes and genomes, 12(5), 291-9.

Kusunose, M., et al., (1964) Enzymatic ω-Oxidation of Fatty Acids: I. Products of Octanoate, Decanoate, and Laurate Oxidation. J. Biol. Chem. 239, 1374-1380.

Landini, P., et al., (1994) Structure and transcriptional regulation of the *Escherichia coli* adaptive response gene aidB. J. Bacteriol., 176(21), 6583-9.

Lennen R.M. & Pfleger B,F. (2012) Engineering *Escherichia coli* to synthesize free fatty acids. Trends Biotechnol. 30:659-667.

Lin S., et al., (2010) Biotin synthesis begins by hijacking the fatty acid synthetic pathway. Nat. Chem. Biol. 6, 682-688.

Magner, D.B., et al., (2007) RecQ promotes toxic recombination in cells lacking recombination intermediate-removal proteins. Molecular cell, 26(2), 273-86.

Martin C.H., et al., (2013) A platform pathway for production of 3-hydroxyacids provides a biosynthetic route to 3-hydroxy-γ-butyrolactone. Nat. Commun. 4, 1414.

Massengo-Tiasse R.P. & Cronan J.E. (2008) Vibrio cholerae FabV defines a new class of enoyl-acyl carrier protein reductase. J. Biol. Chem. 283:1308-1316.Miller, J. H. (1972) Experiments in Molecular Genetics. Cold Spring Harbor, New York: Cold Spring Harbor Laboratory Press.

McKenna, E.J. & Coon, M.J. (1970) Enzymatic ω-Oxidation: IV. Purification and Properties of the ω-Hydroxylase of Pseudomonas oleovorans. J. Biol. Chem. 245, 3882-3889.

O'Brien, W. J. & Fremian, F. E. (1977) Evidence fora complex of three beta-oxidation enzymes in *Escherichia coli*: induction and localization. Journal of bacteriology, 132(2), 532-40.

Preusser, A., et al., (1999) Crotonobetaine reductase from *Escherichia coli* consists of two proteins. Biochimica et biophysica acta, 1431(1), 166-78.

Rohankhedkar, M.S., et al., (2006) The AidB Component of the *Escherichia coli* Adaptive Response to Alkylating Agents Is a Flavin-Containing, DNA-Binding Protein, 188(1), 223-230.

Shams Yazdani, S. & Gonzalez, R. (2008) Engineering *Escherichia coli* for the efficient conversion of glycerol to ethanol and co-products. Metabolic engineering, 10(6), 340-51.

Shen, C.R., et al., (2011) Driving forces enable high-titer anaerobic 1-butanol synthesis in *Escherichia coli*. Applied and environmental microbiology, 77(9), 2905-15.

Schrewe, M., et al., (2011) Kinetic Analysis of Terminal and Unactivated C-H Bond Oxyfunctionalization in Fatty Acid Methyl Esters by Monooxygenase-Based Whole-Cell Biocatalysis. Adv. Synth. Catal. 353, 3485-3495.

Schrewe M., at al., (2013) Direct Terminal Alkylamino-Functionalization via Multistep Biocatalysis in One Recombinant Whole-Cell Catalyst. Adv. Synth. Catal. 355, 1693-1697.

Schrewe, M., et al., (2014) Reaction and Catalyst Engineering to Exploit Kinetically Controlled Whole-Cell Multistep Biocatalysis for Terminal FAME Oxyfunctionalization. Biotechnol. Bioeng. 111, 1820-1830.

Taguchi, S., et al., (2008) A microbial factory for lactate-based polyesters using a lactate-polymerizing enzyme. PNAS (USA), 105(45), 17323-7.

Thomason, L., et al., (2007) Recombineering: genetic engineering in bacteria using homologous recombination. Current protocols in molecular biology / edited by Frederick M. Ausubel . . . [et al.], Chapter 1, Unit 1.16.

Tseng, H.-C., & Prather, K. L. J. (2012). Controlled biosynthesis of odd-chain fuels and chemicals via engineered modular metabolic pathways. Proceedings of the National Academy of Sciences of the United States of America, 109 (44), 17925-30. doi:10.1073/pnas.1209002109.

Tucci, S. & Martin, W. (2007) A novel prokaryotic trans-2-enoyl-CoA reductase from the spirochete Treponema denticola. FEBS letters, 581(8), 1561-6.

Vick, J. E., et al., (2011) Optimized compatible set of BioBrickTM vectors for metabolic pathway engineering. Applied microbiology and biotechnology, 1275-1286.

Weeks, G. & Wakil, S. J. (1968) General Properties of the Reductases From *Escherichia* on the Mechanism of Fatty Acid.

Willis R.M., et al., (2011) Characterization of a Fatty Acyl-CoA Reductase from Marinobacter aquaeolei VT8: A Bacterial Enzyme Catalyzing the Reduction of Fatty Acyl-CoA to Fatty Alcohol. Biochemistry 50:10550-8.

White S.W., et al., (2005) The structural biology of type II fatty acid biosynthesis, p. 791-831, Annual Review of Biochemistry, vol. 74. Annual Reviews, Palo Alto.

Wiesenborn, D.P., et al., (1988) Thiolase from Clostridium acetobutylicum ATCC 824 and Its Role in the Synthesis of Acids and Solvents. App. Environ. Microbiol., 54(11), 2717-22.

(56) References Cited

OTHER PUBLICATIONS

European Search Report for related Application, No. 15740946.7, dated Jun. 29, 2017.

\* cited by examiner

TYPE II FATTY ACID SYNTHESIS ENZYMES IN REVERSE β-OXIDATION

PRIOR RELATED APPLICATIONS

This application is a National Phase filing under 35 U.S.C. § 371 of International Application PCT/US2015/12932, filed on Jan. 26, 2015, which claims priority to 61/932,057, filed Jan. 27, 2014. Each application is expressly incorporated by reference herein in its entirety for all purposes.

FEDERALLY SPONSORED RESEARCH STATEMENT

This invention was made with government support under Grant Nos: CBET-1134541, CBET-1067565, and EEC-0813570, awarded by the NSF. The government has certain rights in the invention.

FIELD OF THE DISCLOSURE

The disclosure generally relates to the use of microorganisms to make feedstock chemicals, e.g., fatty acids and derivatives thereof, by driving the beta oxidation cycle in reverse.

BACKGROUND OF THE DISCLOSURE

Much effort has been devoted in recent years to the production of biofuels, such as ethanol, butanol, higher-chain alcohols, and hydrocarbons via microbial fermentation of sugars and other biomass constituents.

To date, the fatty acid biosynthesis pathway has been widely used as the means to generate higher-chain (C≥4) acyl-CoA thioesters required for the synthesis of the aforementioned products. However, the operation of this pathway is not efficient because it consumes ATP in the synthesis of malonyl-ACP, which is the donor of two-carbon units for chain elongation. As a consequence, the ATP yield associated with the production of hydrocarbon through the fatty acid synthesis pathway is very low. This, in turn, greatly limits cell growth and hydrocarbon and other product production.

We have implemented an entirely novel approach, driving beta oxidation in reverse to make fatty acids instead of degrading them (see US20130316413, WO2013036812, each incorporated by reference in its entirety for all purposes). Unlike the fatty acid biosynthesis pathway, the reversal of the β-oxidation cycle operates with coenzyme-A (CoA) thioester intermediates and uses acetyl-CoA directly for acyl-chain elongation (rather than first requiring ATP-dependent activation to malonyl-CoA).

A engineered microorganism having a reverse beta oxidation cycle that produces alcohols, carboxylic acids, and hydrocarbons, and derivatives thereof, generally includes i) expression of the β-oxidation cycle in the absence of fatty acids and presence of a non-fatty acid carbon source, ii) functional operation of the β-oxidation cycle in the reverse or biosynthetic direction (e.g. making fats rather than degrading them), iii) overexpression of one or more termination enzymes that convert reverse beta oxidation cycle intermediates to a desired alcohol, carboxylic acid, or hydrocarbon, thus exiting or terminating the cycle for that intermediate. Further, any of the alcohols, carboxylic acids, and hydrocarbon products can be further modified to make other products, such as aldehydes, and the like, in secondary termination pathways.

The utility of this technology relates to the efficient synthesis of hydrocarbons, etc. using an engineered reversal of the β-oxidation cycle, which in turn will establish a new paradigm for the production of advanced biofuels. The ubiquitous nature of β-oxidation enzymes should enable the combinatorial synthesis of non-native products in industrial organisms with a minimum number of foreign genes, an approach that would ensure the efficient functioning of the engineered pathways. By enabling the production of products through a functional reversal of the β-oxidation cycle, this technology will contribute to the creation of fundamentally new approaches that could enable efficient production of second-generation biofuels.

We take the above research forward in this disclosure, adding further diversification of enzymes to be used as part of this pathway.

SUMMARY OF THE DISCLOSURE

This disclosure demonstrates that enzymes from the type II (a discrete set of enzymes) fatty acid synthesis ("FAS") pathway can be used in combination with thiolases to operate a functional reversal of the β-oxidation cycle. Specifically, a combination of thiolases with one or more of 3-oxoacyl-[acyl-carrier-protein] reductase (FabG, others), 3-hydroxyacyl-[acp] dehydratase (FabA, FabZ, others), and enoyl-[acyl-carrier-protein] reductase (FabI, FabK, FabL, FabV, others) yields a functional reversal of the β-oxidation cycle. If only one or two enzymes are used, the remaining enzymes will be traditional beta oxidation enzymes. Once this cycle is coupled with the appropriate priming and termination pathways, the production of carboxylic acids, alcohols, hydrocarbons, amines and their α-, β-, and ω-functionalized derivatives from renewable carbon sources can be achieved.

A thiolase that condenses acetyl-CoA with an acyl-CoA (or functionalized acyl-CoA) of varying chain length. One or more enzymes from the FAS pathway (see Table below) are then used for the dehydrogenation (FabG), dehydration (FabA, FabZ), and reduction (FabI, FabK, FabL, FabV) steps resulting in an acyl-CoA that is 2 carbons longer than the starting unit. The termination enzyme(s) pulls intermediates from the cycle, and makes one or more final product(s).

| RXN | FAS ENZYME | BOX ENZYME |
| --- | --- | --- |
| catalyzes the reduction of a β-ketoacyl-CoA to a (3R)-β-hydroxyacyl-CoA | 3-oxoacyl-[acyl-carrier-protein] reductase | 3-hydroxyacyl-CoA dehydrogenase |
| catalyzes the dehydration of a (3R)-β-hydroxyacyl-CoA to a transenoyl-CoA | hydroxyacyl-[acyl-carrier-protein] dehydratase | enoyl-CoA hydratase or 3-hydroxyacyl-CoA dehydratase |
| catalyzes the reduction of a transenoyl-CoA to an acyl-CoA | enoyl-[acyl-carrier-protein] reductase | acyl-CoA dehydrogenase or trans-enoyl-CoA reductase |

| RXN | FAS ENZYME | BOX ENZYME |
|---|---|---|
| that is two carbons longer than the acyl coA primer or starting unit | | |

The key difference between this and the FAS pathway is that we are circumventing the energy intensive step of the FAS pathway (decarboxylative condensation) with a non-decarboxylative condensation through the aforementioned thiolases. This and the fact that the enzymes will be working with CoA intermediates as opposed to the ACP intermediates used in the FA synthesis pathway are the key distinctions in this remaining a "reverse beta-oxidation pathway."

| Gene or Abbreviation | Definition |
|---|---|
| Δ | Refers to reduced activity wherein reduced activity is at least an 75% reduction of wild type activity, and preferably, 80, 85, 90, 95 or 100% reduction. 100% reduction in activity may also be called knockout or null mutant herein. |
| abaT | Gene encoding 4-aminobutyrate transaminase from *Mus musculus* |
| ACH2 | Gene encoding thioesterase from *Arabidopsis thaliana* |
| ackA | Gene encoding acetate kinase, required for synthesis of acetate from acetyl-CoA. |
| acot8 | Gene encoding thioesterase from *Mus musculus* |
| acr1 | Gene encoding a fatty aldehyde-forming acyl-CoA reductases from *Acinetobacter calcoaceticus* |
| acrM | Gene encoding a fatty aldehyde-forming acyl-CoA reductases from *Acinetobacter* sp. strain M-1 |
| adhE | Gene encoding aldehyde/alcohol dehydrogenase, required for synthesis of ethanol from acetyl-CoA |
| adhE2 | Gene encoding aldehyde/alcohol dehydrogenase from *Clostridium acetobutylicum* |
| ald | Gene encoding an aldehyde-forming coenzyme-A thioester reductase from *Clostridium beijerinckii* |
| arcA | Encodes the cytosolic transcription factor of *E. coli*'s ArcAB two-component system, a global regulator of gene expression under microaerobic and anaerobic conditions. ArcAB regulates the expression of a large number of operons involved in respiratory and fermentative metabolism (including repression of fad regulon). |
| arcB | Encodes the membrane associated sensor kinase and phosphatase of *E. coli*'s ArcAB two-component system, a global regulator of gene expression under microaerobic and anaerobic conditions. ArcAB regulates the expression of a large number of operons involved in respiratory and fermentative metabolism (including repression of fad regulon). |
| At3g11980 | Gene encoding an alcohol-forming coenzyme-A thioester reductase from *Arabidopsis thaliana* |
| At3g44560 | Gene encoding an alcohol-forming coenzyme-A thioester reductase from *Arabidopsis thaliana* |
| At3g56700 | Gene encoding an alcohol-forming coenzyme-A thioester reductase from *Arabidopsis thaliana* |
| At5g22500 | Gene encoding an alcohol-forming coenzyme-A thioester reductase from *Arabidopsis thaliana* |
| atoB | Gene encoding an acetyl-CoA acetyltransferase |
| atoC | Encodes the cytosolic transcription factor of *E. coli*'s AtoSC two-component system, which induces the ato operon (atoDAEB) for metabolism of short chain fatty acids in response to the presence of acetoacetate. |
| atoC(c) | atoC mutant that induces constitutive expression of the ato operon (atoDAEB) in the absence of acetoacetate. |
| atoD | Gene encoding acetyl-CoA:acetoacetyl-CoA transferase |
| atoS | Encodes the membrane associated sensor kinase of *E. coli*'s AtoSC two-component system, which induces the ato operon (atoDAEB) for metabolism of short chain fatty acids in response to the presence of acetoacetate. |
| betA | Gene encoding choline dehydrogenase; used as a surrogate of alcohol dehydrogenase in the synthesis of n-alcohols |
| bktB | Gene encoding beta-ketothiolase from *Ralstonia eutropha* |
| buk | Gene encoding carboxylate kinase from *Clostridium acetobutylicum* or *Enterococcus faecalis* |
| cat1 | Gene encoding Succinyl-CoA:coenzyme A transferase from *Clostridium kluyveri* |
| cat2 | Gene encoding 4-hydroxybutyrate CoA transferase from *Clostridium kluyveri* |
| catF | Gene encoding beta-ketoadipyl-CoA thiolase from *Pseudomonas* sp. Strain B13 |
| CER4 | Gene encoding an alcohol-forming coenzyme-A thioester reductase from *Arabidopsis thaliana* |
| cddC | Gene encoding alcohol dehydrogenase/oxidase from *Rhodococcus ruber* SC1 |
| cddD | Gene encoding aldehyde dehydrogenase from *Rhodococcus ruber* SC1 |
| chnD | Gene encoding alcohol dehydrogenase/oxidase from *Acinetobacter* sp. SE19 |
| chnE | Gene encoding aldehyde dehydrogenase from *Acinetobacter* sp. SE19 |
| crp | Encodes transcriptional dual regulator CRP, which upon binding to its allosteric effector cyclic AMP (cAMP) regulate the expression of about 200 genes (most of them involved in the catabolism of carbon sources, including the fad regulon). |
| crp* | crp mutant encoding a cAMP-independent CRP (i.e. CRP*, which does not require cAMP to regulate gene expression and hence prevents catabolite repression of fad regulon in the presence of glucose) |
| ctfB | Gene encoding butyrate-acetoacetate CoA-transferase from *Clostridium acetobutylicum* |
| CYP | Gene encoding a carboxylic acid omega hydroxylase family enzyme, such as those from *Arabidopsis* (CYP94B1, CYP94C1, and CYP86A subfamily), *V. sativa* (CYP94A1, CYP94A2), *Nicotiana tabacum* (CYP94A5), *Ps. hybrida* (CYP92B1, CYP703A1), *Zea mays* (CYP78A1), *C. tropicalis* (CYP52A1, CYP52A2), rat (CYP4A1), or human (CYP4A11, CYP4B1, and CYP4F2) |
| egTER | Gene encoding an NAD(P)H-dependent transenoyl-CoA reductase from *T. gracilis* |
| eutE | Gene encoding predicted aldehyde dehydrogenase with high sequence similarity to adhE |
| eutG | Gene encoding predicted alcohol dehydrogenase |
| fabA | Gene encoding 3-hydroxyacyl-[acp] dehydratase |

-continued

| Gene or Abbreviation | Definition |
|---|---|
| fabG | Gene encoding 3-oxoacyl-[acyl-carrier-protein]/β-ketoacyl-[ACP] reductase |
| fabI | Gene encoding enoyl-[acyl-carrier-protein] reductase |
| fabK | Gene encoding enoyl-[acyl-carrier-protein] reductase from *E. faecalis* |
| fabL | Gene encoding enoyl-[acyl-carrier-protein] reductase from *B. subtilis* ( |
| fabV | Gene encoding enoyl-[acyl-carrier-protein] reductase from *V. cholerea* |
| fabZ | Gene encoding 3-hydroxyacyl-[acp] dehydratase |
| FACoAR (Maqu2507) | Gene encoding an alcohol-forming coenzyme-A thioester reductase from *Marinobacter aquaeolei* VT8 |
| fadA | Gene encoding 3-ketoacyl-CoA thiolase (thiolase I), component of fatty acid oxidation complex |
| fadB | Gene encoding hydroxyacyl-CoA dehydrogenase, aka fused 3-hydroxybutyryl-CoA epimerase and delta(3)-cis-delta(2)-trans-enoyl-CoA isomerase and enoyl-CoA hydratase, part of fatty acid oxidation complex |
| fadBA | Both fadB and fadA |
| fadD | Gene encoding acyl-CoA synthetase (long-chain-fatty-acid--CoA ligase), part of fatty acyl-CoA synthetase complex |
| fadE | Gene encoding acyl-CoA dehydrogenase, a medium-long-chain fatty acyl-CoA dehydrogenase |
| fadI | Gene encoding 3-ketoacyl-CoA thiolase, part of fatty acid oxidation complex |
| fadJ | Gene encoding hydroxyacyl-CoA dehydrogenase, aka fused enoyl-CoA hydratase and epimerase and isomerase |
| fadK | Gene encoding short chain acyl-CoA synthetase |
| fadL | Gene encoding long-chain fatty acid outer membrane transporter |
| fadM | Gene encoding long-chain acyl-CoA thioesterase |
| fadR | Gene encoding a dual regulator of fatty acid metabolism, which exerts negative control over the fad regulon and positive control over expression of unsaturated fatty acid biosynthesis genes |
| fadR* | fadR mutant that allows expression of the fad regulon in the absence of fatty acids |
| Fnr | Gene encoding transcriptional dual regulator, regulates genes involved in the transition from aerobic to anaerobic growth |
| frdA | Gene encoding fumarate reductase, required for synthesis of succinate from fumarate |
| fucO | Gene encoding L-1,2-propanediol oxidoreductase |
| gabT | Gene encoding 4-aminobutyrate transaminase |
| ldhA | Gene encoding lactate dehydrogenase |
| mhpF | Gene encoding acetaldehyde dehydrogenase |
| MIT9313_pmt1231 | Gene encoding an aldehyde decarbonylase from or *Prochlorococcus marinus* MIT9313 |
| mgsA | Gene encoding methylglyoxal synthase; key enzyme in the synthesis of lactate through the methylglyoxal bypass |
| MXAN_0191 | Gene encoding fatty acid alpha-hydroxylase from *Myxococcus xanthus* |
| oleA | Gene encoding the enzyme that catalyzes non-decarboxylative Claisen condensation of CoA-thioesters in *Xanthomonas campestris* |
| oleB | Gene encoding a member of the α/β-hydrolase superfamily in *Xanthomonas campestris* |
| oleC | Gene encoding a member of the AMPdependent ligase/synthase superfamily or acetyl-CoA synthetase-like superfamily in *Xanthomonas campestris* |
| oleD | Gene encoding a member of the short-chain dehydrogenase/reductase superfamily in *Xanthomonas campestris* |
| paaJ | Gene encoding β-ketoadipyl-CoA thiolase catalyzing two beta-oxidation steps in phenylacetate catabolism |
| pcaF | Gene encoding acetyl-CoA acetyltransferase from *Rhodococcus opacus* or beta-ketoadipyl-CoA thiolase from *Streptomyces* sp. or *Pseudomonas putida* |
| PCC73102 npun_R1711 | Gene encoding an aldehyde decarbonylase from *Nostoc punctiforme* PCC73102 |
| PCC7942_orf1593 | Gene encoding an aldehyde decarbonylase from *Synechococcus elongatus* PCC7942 |
| pduL | Gene encoding phosphotransacylase from *Salmonella enterica* |
| pduW | Gene encoding carboxylate kinase from *Salmonella enterica* |
| phaA | Gene encoding beta-ketothiolase from *Ralstonia eutropha* |
| pmAD | Gene encoding an aldehyde decarbonylase from *Prochlorococcus marinus* MIT9313 |
| poxB | Gene encoding pyruvate oxidase, which catalyzes the oxidative decarboxylation of pyruvate to form acetate, reduced ubiquinone (ubiquinol), and $CO_2$ |
| pta | Gene encoding phosphotransacetylase, required for synthesis of acetate from acetyl-CoA |
| ptb | Gene encoding phosphotransacylase from *Clostridium acetobutylicum* or *Enterococcus faecalis* |
| PTE1 | Gene encoding thioesterase from *S. cerevisiae* |
| STIAU_3334 | Gene encoding fatty acid alpha-hydroxylase from *Stigmatella aurantiaca* |
| tdTER | Gene encoding an NAD(P)H-dependent transenoyl-CoA reductase from *T. denticola* |
| tesA | Gene encoding multifunctional acyl-CoA thioesterase I and protease I and lysophospholipase L1 |
| tesB | Gene encoding thioesterase II from *E. coli* or *A. Borkumensis* |
| thlA | Gene encoding acetoacetyl-CoA thiolase from *Clostridium acetobutylicum* |
| thlB | Gene encoding acetoacetyl-CoA thiolase from *Clostridium acetobutylicum* |
| ucpA | predicted oxidoreductase, sulfate metabolism protein (used as surrogate of aldehyde-forming acyl Coenzyme A Reductase) |
| yahK | Gene encoding alcohol dehydrogenase/oxidase |
| ybbO | predicted oxidoreductase with NAD(P)-binding Rossmann-fold domain (used as surrogate of aldehyde-forming acyl Coenzyme A Reductase) |
| ybdH | Gene encoding predicted oxidoreductase |
| ybgC | Gene encoding esterase/thioesterase |
| yciA | Gene encoding acyl-CoA thioesterase |
| ydiF | Gene encoding predicted acetyl-CoA:acetoacetyl-CoA transferase |
| ydiI | Gene encoding esterase/thioesterase |
| ydiL | Gene encoding fused predicted acetyl-CoA:acetoacetyl-CoA transferase: α subunit/β subunit |
| ydiO | Genes encoding predicted acyl-CoA dehydrogenase |

-continued

| Gene or Abbreviation | Definition |
|---|---|
| ydiQ | Gene encoding putative subunit of YdiQ-YdiR flavoprotein |
| ydiR | Gene encoding putative subunit of YdiQ-YdiR flavoprotein |
| ydiS | Gene encoding putative flavoprotein |
| ydiT | Gene encoding putative ferredoxin |
| yiaY | Gene encoding predicted Fe-containing alcohol dehydrogenase |
| yjgB | Gene encoding alcohol dehydrogenase/oxidase |
| yqeF | Gene encoding predicted acetyl-CoA acetyltransferases |
| yqhD | Gene encoding NADP-dependent aldehyde/alcohol dehydrogenase |
| + | Refers to an overexpressed activity, meaning at least 150% wild type activity, and preferably 200, 500, 1000% or more. |

See also Table A for various termination enzymes

As used herein a "reverse beta oxidation" or BOX-R cycle is a pathway that results in the synthesis of fatty acids by adding 2 carbon units to a primer molecule in each turn of the cycle. BOX-R uses acetyl-CoA as the extender unit, added on by a thiolase that uses a non-decarboxylating mechanism. Further, as noted above, any of the BOX-R intermediates can be pulled out of the cycle and further modified in the many ways shown herein.

By contrast, the fatty acid biosynthesis pathway uses keto-acyl-ACP synthases, which employ a decarboxylating mechanism, and malonyl-ACP as the extender or donor unit.

As used herein, a "primer" is a starting molecule for the BOX-R cycle to add two carbon donor units to. The initial primer is either typically acetyl-CoA or propionyl-CoA, but as the chain grows by adding donor units in each cycle, the primer will accordingly increase in size. In some cases, the bacteria can also be provided with larger primers, e.g., C4 primers, etc. added to the media or obtained from other cell pathways. Further, non-traditional primers can be used wherever atypical products are desired (i.e., hydroxylated primers, carboxylated primers, etc. . . . ). As used herein, the "donor" of the 2 carbon units is acetyl-CoA.

As used herein "type II fatty acid synthesis enzymes" refer to those enzymes that function independently, e.g., are discrete, monofunctional enzymes, used in fatty acid synthesis. Type II enzymes are found in archaea and bacteria. Type I systems, in contrast, utilise a single large, multifunctional polypeptide.

As used herein, a "thiolase" is an enzyme that catalyzes the condensation of an acyl-CoA or other primer with a 2-carbon donor acetyl-CoA to produce a β-ketoacyl-CoA in a non-decarboxylative condensation reaction.

Many examples of thiolase enzymes are provided herein and the following table provides several examples:

TABLE A

Example Thiolase Enzymes (EC Number 2.3.1.—)

| Source organism and gene name | Protein Accession Numbers |
|---|---|
| E. coli atoB | NP_416728.1 |
| E. coli yqeF | NP_417321.2 |
| E. coli fadA | YP_026272.1 |
| E. coli fadI | NP_416844.1 |
| Ralstonia eutropha bktB | AAC38322.1 |
| Pseudomonas sp. Strain B13 catF | AAL02407.1 |
| E coli paaJ | NP_415915.1 |
| Pseudomonas putida pcaF | AAA85138.1 |
| Rhodococcus opacus pcaF | YP_002778248.1 |
| Streptomyces sp. pcaF | AAD22035.1 |
| Ralstonia eutropha phaA | AEI80291.1 |
| Clostridium acetobutylicum thlA | AAC26023.1 |
| Clostridium acetobutylicum thlB | AAC26026.1 |

As used herein a "3-oxoacyl-[acyl-carrier-protein] reductase" or "3-oxoacyl-[ACP] reductase" is an enzyme that catalyzes the reduction of a β-ketoacyl-CoA to a (3R)-β-hydroxyacyl-CoA:

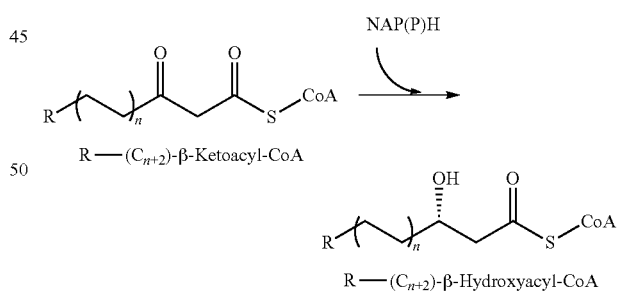

As used herein, a "3-hydroxyacyl-[ACP] dehydratase" is an enzyme that catalyzes the dehydration of a (3R)-β-hydroxyacyl-CoA to a transenoyl-CoA:

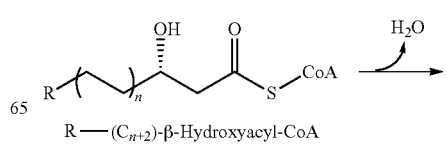

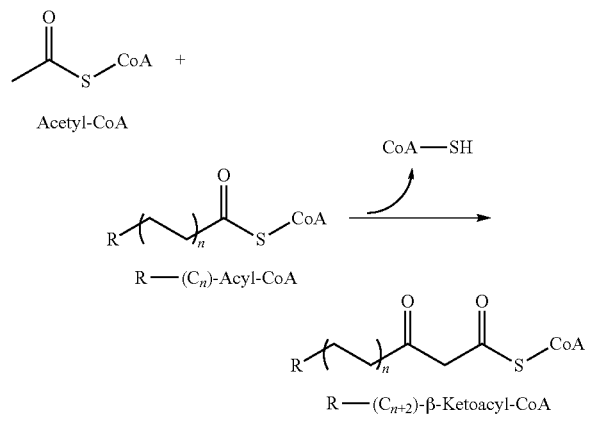

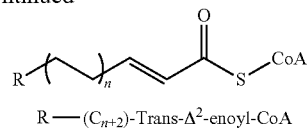

R—($C_{n+2}$)-Trans-$\Delta^2$-enoyl-CoA

As used herein, an "enoyl-[ACP] reductase" that catalyzes the reduction of a transenoyl-CoA to an acyl-CoA:

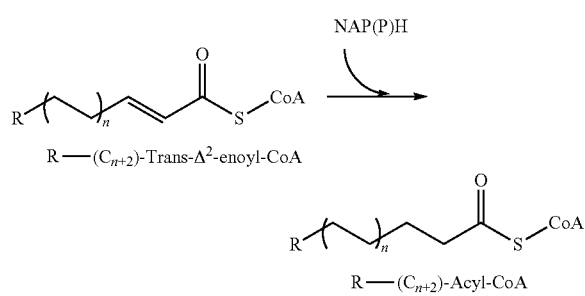

Many examples of FAS enzymes catalyzing these reactions are provided herein and the following table provides several examples:

TABLE B

| Reaction | Source organism and gene name | Protein Accession Numbers |
| --- | --- | --- |
| β-ketoacyl-CoA → (3R)-β-hydroxyacyl-CoA | E. coli fabG | NP_415611.1 |
| (3R)-β-hydroxyacyl-CoA → transenoyl-CoA | E. coli fabA | NP_415474.1 |
| | E. coli fabZ | NP_414722.1 |
| transenoyl-CoA →acyl-CoA | E. coli fabI | NP_415804.1 |
| | Enterococcus faecalis fabK | NP_816503.1 |
| | Bacillus subtilis fabL | KFK80655.1 |
| | Vibrio cholerae fabV | ABX38717.1 |

As used herein "termination pathway" refers to one or more enzymes (or genes encoding same) that will pull reaction intermediates out the BOX-R cycle and produce the desired end product or precursor thereof.

By "primary termination pathway" what is meant is a intermediate from the BOX-R is pulled out of the BOX-R by one (which can have more than one activity) or more termination enzymes and results in i) carboxylic acids, ii) primary alcohols, iii) hydrocarbons, or iv) primary amines, from CoA intermediates as described in FIG. 1.

By "secondary termination pathway" what is meant is that the intermediate pulled out of the BOX-R by a primary termination pathway enzyme is further modified by one or more enzymes.

Many examples of termination pathways are provided herein and the following table provides several examples:

TABLE C

Termination Pathways

| Reaction | Illustration | EC Numbers | Enzyme names | Source organism and gene name | Protein Accession Numbers |
| --- | --- | --- | --- | --- | --- |
| Acyl-CoA4 → Carboxylic acid | An acyl-CoA → A carboxylic acid | 3.1.2.- | Thioesterase | E. coli tesA | NP_415027.1 |
| | | | | E. coli tesB | NP_414986.1 |
| | | | | E. coli yciA | NP_415769.1 |
| | | | | E. coli fadM | NP_414977.1 |
| | | | | E. coli ydil | NP_416201.1 |
| | | | | E. coli ybgC | NP_415264.1 |
| | | | | Alcanivorax borkumensis tesB2 | YP_692749.1 |
| | | | | Fibrobacter succinogenes Fs2108 | YP_005822012.1 |
| | | | | Prevotella ruminicola Pr655 | YP_003574018.1 |
| | | | | Prevotella ruminicola Pr1687 | YP_003574982.1 |
| | | 2.8.3.8 | Acyl-CoA:acetyl-CoA transferase | E. coli atoD | NP_416725.1 |
| | | | | Clostridium kluyveri cat2 | AAA92344.1 |
| | | | | Clostridium acetobutylicum ctfAB | NP_149326.1, NP_149327.1 |
| | | | | E. coli ydiF | NP_416209.1 |
| | | 2.3.1.-; 2.7.2.1; 2.7.2.15 | Phosphotransacylase + Carboxylate kinase | Clostridium acetobutylicum ptb | NP_349676.1 |
| | | | | Enterococcus faecalis ptb | AAD55374.1 |
| | | | | Salmonella enterica pduL | AAD39011.1 |

TABLE C-continued

Termination Pathways

| Reaction | Illustration | EC Numbers | Enzyme names | Source organism and gene name | Protein Accession Numbers |
|---|---|---|---|---|---|
| | | | | *Clostridium acetobutylicum* buk | AAK81015.1 |
| | | | | *Enterococcus faecalis* buk | AAD55375.1 |
| | | | | *Salmonella enterica* pduW | AAD39021.1 |
| Acyl-CoA → Alcohol | 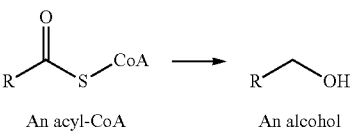 An acyl-CoA → An alcohol | 1.2.1.84 | Alcohol-forming CoA reductase | *Clostridium acetobutylicum* adhE2 | YP_009076789.1 |
| | | | | *Arabidopsis thaliana* At3g11980 | AEE75132.1 |
| | | | | *Arabidopsis thaliana* At3g44560 | AEE77915.1 |
| | | | | *Arabidopsis thaliana* At3g56700 | AEE79553.1 |
| | | | | *Arabidopsis thaliana* At5g22500 | AED93034.1 |
| | | | | *Arabidopsis thaliana* CER4 | AEE86278.1 |
| | | | | *Marinobacter aguaeolei* VT8 maqu_2220 | YP_959486.1 |
| | | | | *Marinobacter aguaeolei* VT8 maqu_2507 | YP_959769.1 |
| Acyl-CoA → Aldehyde | 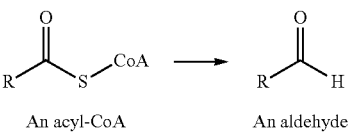 An acyl-CoA → An aldehyde | 1.2.1.10 | Aldehyde forming CoA reductase | *Acinetobacter calcoaceticus* acr1 | AAC45217.1 |
| | | | | *Acinetobacter* sp Strain M-1 acrM | BAB85476.1 |
| | | | | *Clostridium beijerinckii* ald | AAT66436.1 |
| | | | | *E. coli* eut E | NP_416950.1 |
| | | | | *Salmonella enterica* eutE | AAA80209.1 |
| | | | | *E. coli* mhpF | NP_414885.1 |
| Aldehyde → Alcohol | 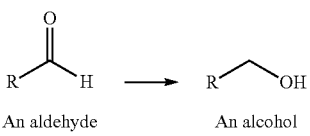 An aldehyde → An alcohol | 1.1.1.- | Alcohol dehydrogenase | *E. coli* betA | NP_414845.1 |
| | | | | *E. coli* dkgA | NP_417485.4 |
| | | | | *E. coli* eutG | NP_416948.4 |
| | | | | *E. coli* fucO | NP_417279.2 |
| | | | | *E. coli* ucpA | NP_416921.4 |
| | | | | *E. coli* yahK | NP_414859.1 |
| | | | | *E. coli* ybbO | NP_415026.1 |
| | | | | *E. coli* ybdH | NP_415132.1 |
| | | | | *E. coli* yiaY | YP_026233.1 |
| | | | | *E. coli* yjgB | NP_418690.4 |
| Aldehyde → Alkane | 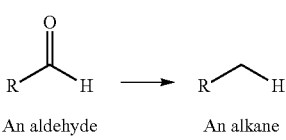 An aldehyde → An alkane | 4.1.99.5 | Aldehyde decarbonylase | *Synechococcus elongatus* PCC7942 orf1593 | Q54764.1 |
| | | | | *Nostoc punctiforme* PCC73102 npun_R1711 | B2J1M1.1 |
| | | | | *Prochlorococcus marinus* MIT9313 pmt1231 | Q7V6D4.1 |
| Aldehyde → Amine | 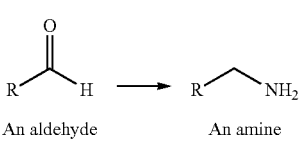 An aldehyde → An amine | 2.6.1.- | Transaminase | *Arabidopsis thaliana* At3g22200 | NP_001189947.1 |
| | | | | *Alcaligenes denitrificans* AptA | AAP92672.1 |
| | | | | *Bordetella bronchiseptica* BB0869 | WP_015041039.1 |
| | | | | *Bordetella parapertussis* BPP0784 | WP_010927683.1 |
| | | | | *Brucella melitensis* | EEW88370.1 |

TABLE C-continued

Termination Pathways

| Reaction | Illustration | EC Numbers | Enzyme names | Source organism and gene name | Protein Accession Numbers |
|---|---|---|---|---|---|
| | | | | BAWG_0478 *Burkholderia pseudomallei* BP102613_I0669 | AFI65333.1 |
| | | | | *Chromobacterium violaceum* CV2025 | AAQ59697.1 |
| | | | | *Oceanicola granulosus* OG2516_07293 | WP_007254984.1 |
| | | | | *Paracoccus denitrificans* PD1222 Pden_3984 | ABL72050.1 |
| | | | | *Pseudogulbenkiania ferrooxidans* ω-TA | WP_008952788.1 |
| | | | | *Pseudomonas putida* ω-TA | P28269.1 |
| | | | | *Ralstonia solanacearum* ω-TA | YP_002258353.1 |
| | | | | *Rhizobium meliloti* SMc01534 | NP_386510.1 |
| | | | | *Vibrio fluvialis* ω-TA | AEA39183.1 |
| | | | | *Mus musculus* abaT | AAH58521.1 |
| | | | | *E. coli* gabT | YP_490877.1 |
| Carboxylic Acid → ω-hydroxyacid | Carboxylic Acid → ω-Hydroxy-Carboxylic Acid | 1.14.- | Carboxylic acid omega hydroxylase | *Pseudomonas putida* alkBGT | YP_009076004.1, Q9WWW4.1, Q9L4M8.1 |
| | | | | *Marinobacter aguaeolei* CYP153A | ABM17701.1 |
| | | | | *Mycobacterium marinum* CYP153A16 | YP_001851443.1 |
| | | | | *Polaromonas* sp. CYP153A | YP_548418.1 |
| | | | | *Nicotiana tabacum* CYP94A5 | AAL54887.1 |
| | | | | *Vicia sativa* CYP94A1 | AAD10204.1 |
| | | | | *Vicia sativa* CYP94A2 | AAG33645.1 |
| | | | | *Arabidopsis thaliana* CYP94B1 | BAB08810.1 |
| | | | | *Arabidopsis thaliana* CYP86A8 | CAC67445.1 |
| | | | | *Candida tropicalis* CYP52A1 | AAA63568.1, AAA34354.1, AAA34334.1 |
| | | | | *Candida tropicalis* CYP52A2 | AAA34353.2, CAA35593.1 |
| | | | | *Homo sapiens* CYP4A11 | AAQ56847.1 |
| ω-hydroxyacid → ω-oxo-acid | ω-Hydroxy-Carboxylic Acid → ω-Oxo-Carboxylic Acid | 1.1.1.- | Alcohol oxidase/ alcohol dehydrogenase | *Rhodococcus ruber* SC1 cddC | AAL14237.1 |
| | | | | *Acinetobacter* sp. SE19 chnD | AAG10028.1 |
| | | | | *E. coli* yahK | NP_414859.1 |
| | | | | *E. coli* yjgB | NP_418690.4 |

TABLE C-continued

Termination Pathways

| Reaction | Illustration | EC Numbers | Enzyme names | Source organism and gene name | Protein Accession Numbers |
|---|---|---|---|---|---|
| ω-oxo-acid → dicarboxylic acid | ω-Oxo-Carboxylic Acid → Dicarboxylic Acid | 1.2.1.- | Aldehyde dehydrogenase | *Rhodococcus ruber* SC1 cddD | AAL14238.1 |
| | | | | *Acinetobacter* sp SE19 chn | AAG10022.1 |
| Carboxylic Acid → α-hydroxyacid | A carboxylic acid → An alpha-hydroxy-carboxylic acid | 1.14.- | Carboxylic acid alpha hydroxylase | *Myxococcus xanthus* MXAN_0191 | YP_628473.1 |
| | | | | *Stigmatella aurantiaca* STIAU_3334 | YP_003957653.1 |

As used herein, references to "cells," "bacteria," "microbes," "microorganisms" or "strains" and all such similar designations include progeny thereof. It is also understood that all progeny may not be precisely identical in DNA content, due to deliberate or inadvertent mutations that have been added to the parent. Mutant progeny that have the same function or biological activity as screened for in the originally transformed cell are included. Where distinct designations are intended, it will be clear from the context.

As used herein, "NAD(P)H" means either cofactor could be used, or both, depending on the enzyme selected and availability of the cofactors I the cell.

The terms "operably associated" or "operably linked," as used herein, refer to functionally coupled nucleic acid sequences.

As used herein "recombinant" is relating to, derived from, or containing genetically engineered material. In other words, the genome (including extrachromosomal elements) was intentionally manipulated by the hand of man in some way.

"Reduced activity" or "inactivation" is defined herein to be at least a 75% reduction in protein activity, as compared with an appropriate control species. Preferably, at least 80, 85, 90, 95% reduction in activity is attained, and in the most preferred embodiment, the activity is eliminated (100%, aka a "knock-out" or "null" mutants). Proteins can be inactivated with inhibitors, by mutation, or by suppression of expression or translation, and the like. Use of a frame shift mutation, early stop codon, point mutations of critical residues, or deletions or insertions, and the like, can completely inactivate (100%) gene product by completely preventing transcription and/or translation of active protein. Reduced activity genes can also be indicated by a minus supercript, e.g. Adh⁻.

"Overexpression" or "overexpressed" is defined herein to be at least 150% of protein activity as compared with an appropriate control species, and preferably 200, 500, 1000%) or more. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. Increased activity genes can also be indicated by a positive supercript, e.g. PYC⁺.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from *Clostridia* would not be endogenous to *Escherichia*, but a plasmid expressing a gene from *E. coli* would be considered to be endogenous to any genus of *Escherichia*, even though it may now be overexpressed. By contrast, an "exogenous" gene is from a different species. "Wild type" means the gene is in use natural form, e.g., it has not been modified by the hand of man.

The use of the word "a" or "an" when used in conjunction with the term "comprising" in the claims or the specification means one or more than one, unless the context dictates otherwise. The use of the term "or" in the claims is used to mean "and/or" unless explicitly indicated to refer to alternatives only or if the alternatives are mutually exclusive.

The term "about" means the stated value plus or minus the margin of error of measurement or plus or minus 10% if no method of measurement is indicated.

The terms "comprise", "have", "include" and "contain" (and their variants) are open-ended linking verbs and allow the addition of other elements when used in a claim. The phrase "consisting of" is closed, and excludes all additional elements. The phrase "consisting essentially of" excludes additional material elements, but allows the inclusions of non-material elements that do not substantially change the nature of the invention, such as instructions for use, buffers, and the like.

The following viations are used herein:

| ABBREVIATION | TERM |
| --- | --- |
| BOX-R | Beta oxidation pathway in reverse. |
| FA | Fatty acid |
| FAD | Flavin adenine dinucleotide |
| FAS | Fatty acid synthesis |
| ACP | Acyl carrier protein |
| BOX | Beta oxidation |
| ENR | enoyl-acyl carrier protein reductase |
| PCT | propionate CoA transferase |

BRIEF DESCRIPTION OF THE DRAWINGS

FIG. 3A. Mass spectrum analysis of FabI reduction of crotonyl-CoA to butyryl-CoA. (i) Controls of crotonyl-CoA (836.3 m/z—gray) and butyryl-CoA (838.3 m/z—black). (ii) Reaction mixture without FabI. (iii) Reaction mixture with FabI.

FIG. 4A. Both short-chain (AtoB) and long-chain (FadA) thiolases were activated in strain JC01(DE3) atoB$^{CT5}$fadBA$^{CT5}$ to facilitate operation of several turns of the BOX-R. The impact of deletion of fadD and yciA on product synthesis is also shown. Gene deletion represented by Δ"gene". All strains included either pETDuet or pET-Duet-fabI (indicated by fabI$^+$) vector. FIG. 4B. Production of odd chain carboxylic acids is facilitated in strain JC01 (DE3) atoB$^{CT5}$fadBA$^{CT5}$ ΔfadD ΔyciA pETDuet-fabI when mePCT is co-expressed from pCDFDuet and the medium is supplemented with 15 mM propionic acid.

FIG. 6A. Butyrate production upon overexpression of enoyl-ACP reductases from Enterococcus faecalis (efFabK), Vibrio cholerae (vcFabV), and Bacillus subtilis (bsFabL) in strain JC01(DE3) atoB$^{CT5}$fadB$^{CT5}$ ΔfadA; FIG. 6B. Longer chain carboxylic acids in JC01(DE3) atoB$^{CT5}$fadBA$^{CT5}$ ΔfadD ΔyciA upon the overexpression of fabI, efFabK or vcfabV. Gene overexpression from pETDuet indicted by listed gene.

Figure 9:
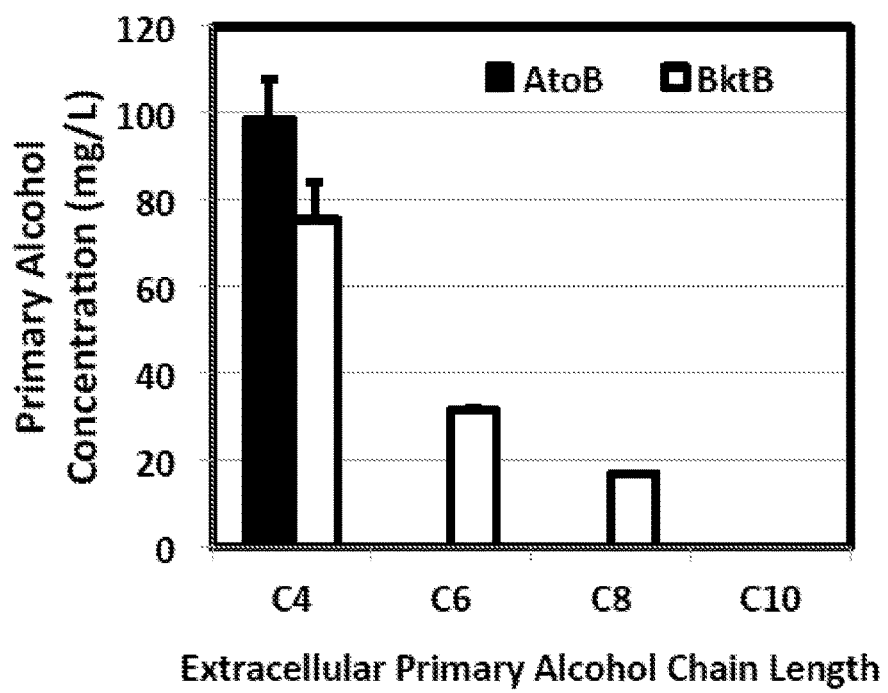

FIG. 9. Primary alcohol production through BOX-R with the use of enzymes from the type II FAS pathway with aldehyde-forming acyl-CoA reductase and alcohol dehydrogenase termination. Product chain length controlled through use of thiolase enzymes (AtoB or BktB) with varying chain length specificity. Data shown for strain JC01(DE3) ΔfadB ΔfadJ (pET-P1-fabI-P2-fabG-fabZ) with either atoB or btkB overexpression under cumate control at the atoB chromosomal locus and *Clostridium beijerinckii* aldehyde-forming acyl-CoA reductase ALD (cbjALD) and *E. coli* alcohol dehydrogenase FucO (fucO) overexpressed from pCDFDuet vector (pCDF-P1-cbjALD-P2-fucO).

Figure 10:
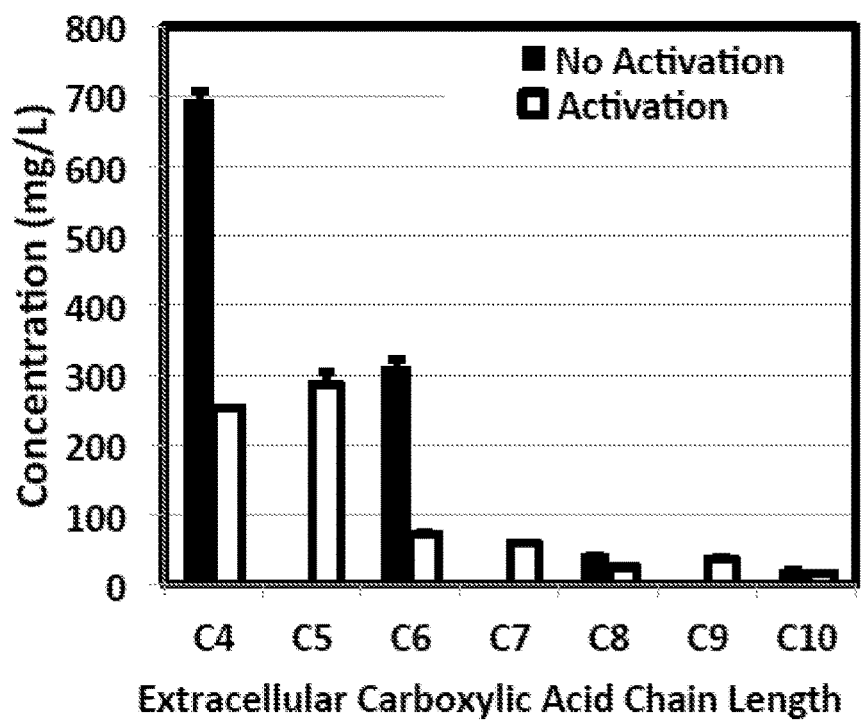

FIG. 10. Odd chain carboxylic acid production with propionate priming through BOX-R with the use of enzymes from the type II FAS pathway. Data shown for strain JC01(DE3) bktB$^{CT5}$ ΔfadB ΔfadJ (pET-P1-fabI-P2-fabG-fabZ) in the presence of 20 mM propionate with (Activation) or without (No Activation) vector for expression *M. elsdenii* propionyl-CoA transferase (mePCT) for the activation of propionate to propionyl-CoA. mePCT overexpressed from pCDFDuet vector (pCDFDuet-mePCT). Note: pCDPDuet may be abbreviated pCDF throughout.

Figure 11:
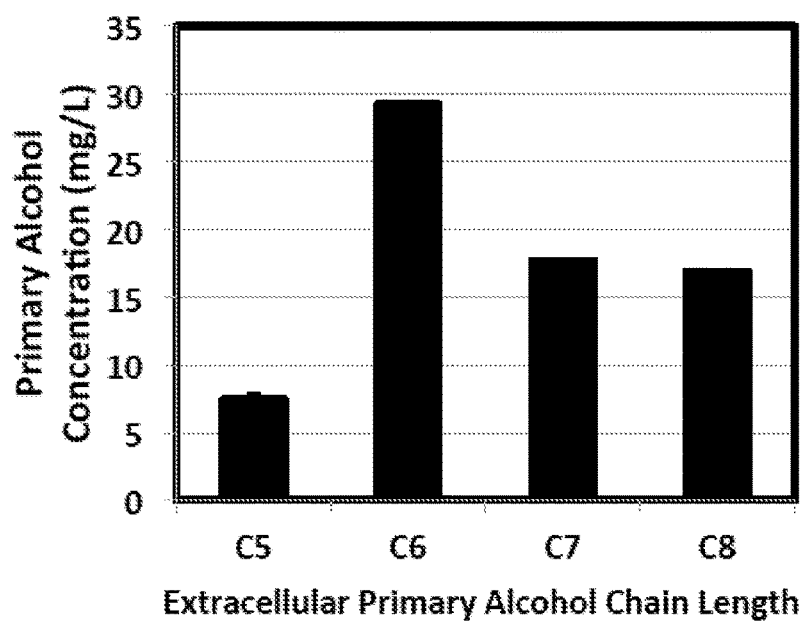

FIG. 11. Primary odd-chain alcohol production with propionate priming through a BOX-R with type II FAS enzymes and alcohol-forming acyl-CoA reductase termination. Data shown for strain JC01(DE3) bktB$^{CT5}$ ΔfadB ΔfadJ (pET-P1-fabI-P2-fabG-fabZ) in the presence of 20 mM propionate with pCDF-P1-mePCT-P2-maqu2507 vector for the overexpression of *M. elsdenii* propionyl-CoA transferase (mePCT) for the activation of propionate to propionyl-CoA and *M. aquaeolei* VT8 alcohol-forming acyl-CoA reductase Maqu2507 (maqu2507) for alcohol forming termination pathway.

Figure 12:
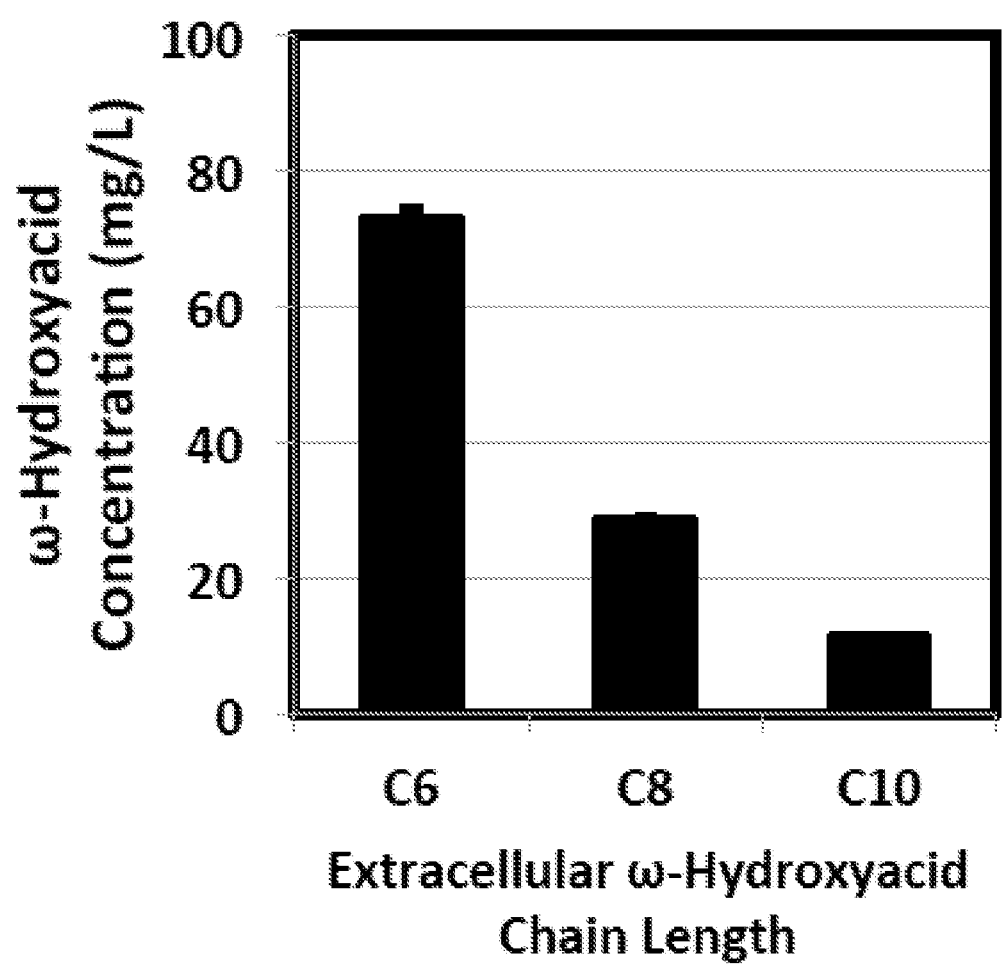

FIG. 12. Synthesis of ω-functionalized products through BOX-R with type II FAS enzymes and ω-oxidation termination. Endogenous thioesterase termination combined with ω-oxidation pathways enables the synthesis of ω-hydroxyacids of varying chain length. ω-hydroxyacids products shown for strain JC01(DE3) bktB$^{CT5}$ ΔfadB ΔfadJ (pET-P1-fabI-P2-fabG-fabZ) expressing *P. putida* alkane monooxygenase (AlkBGT) in pCDFDuet vector (pCDF-P1-alkBGT).

Figure 13A:
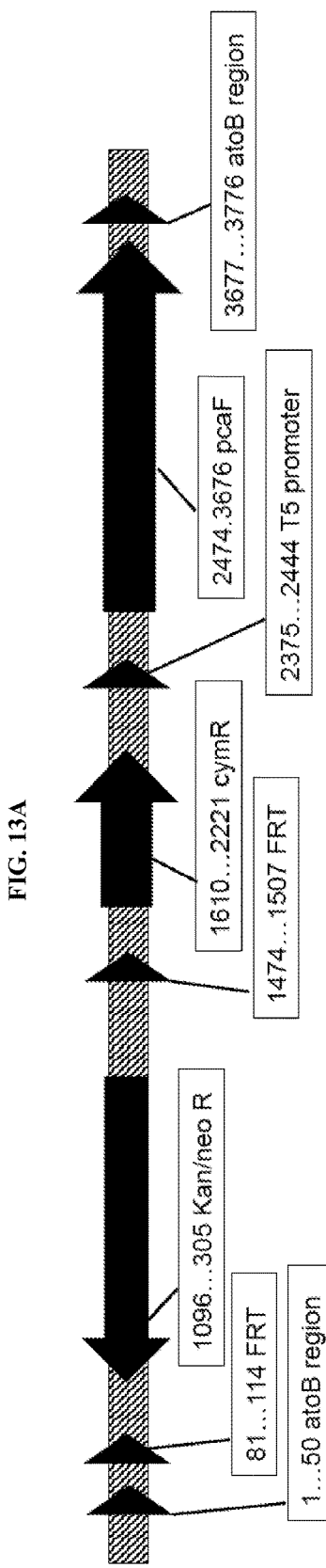
Figure 13B:
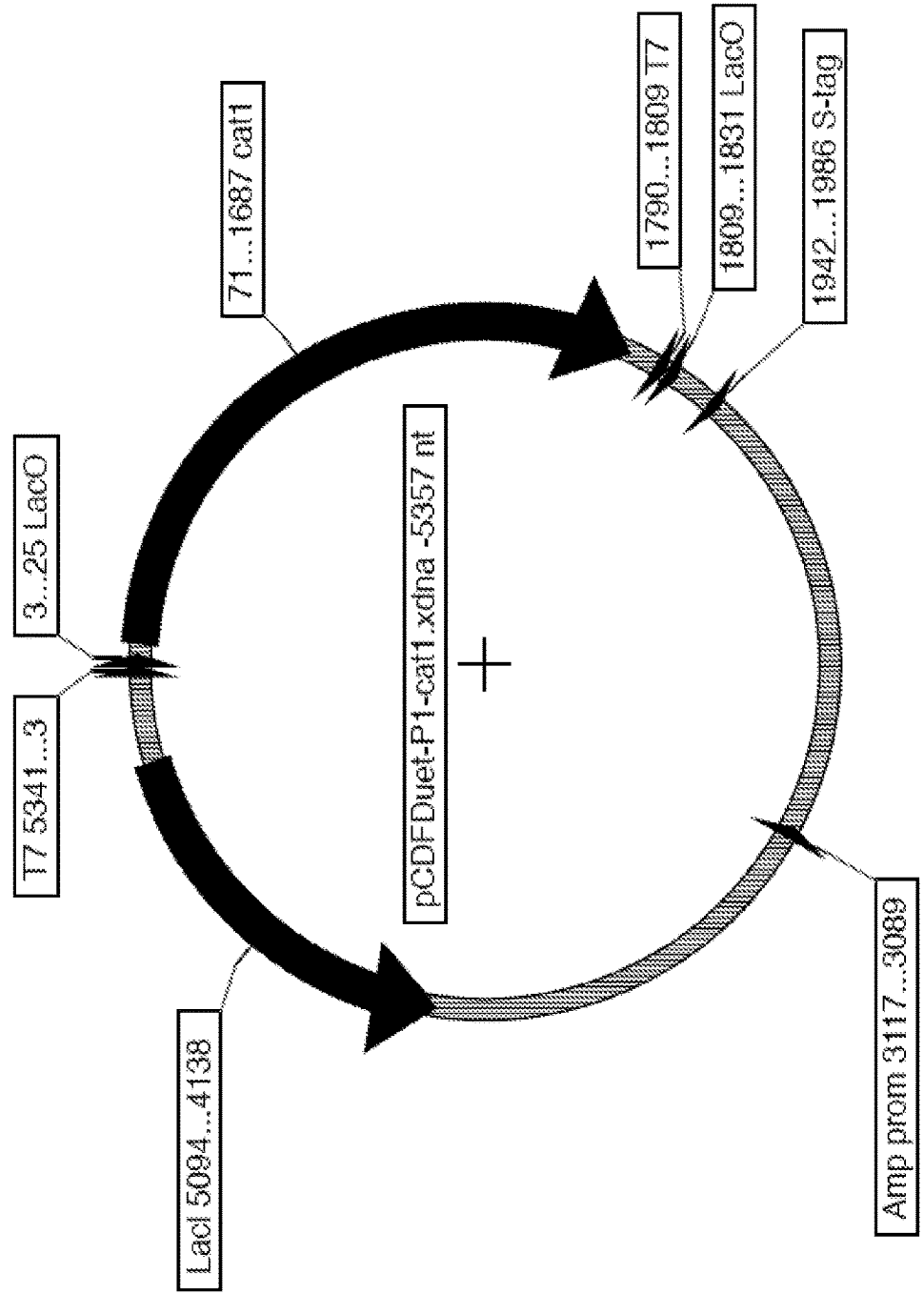

FIG. 13. Genetic constructs for the synthesis of ω-functionalized products with succinate priming through BOX-R with enzymes from type II FAS. FIG. 13A. Chromosomal expression construct for cumate-controlled overexpression of *P. putida* thiolase PcaF at the *E. coli* atoB locus. FIG. 13B. pCDFDuet vector for the overexpression of *C. kluyveri* succinyl-CoA:coenzyme A transferase Cat1 for the activation of succinate to succinyl-CoA (pCDF-P1-cat1).

DETAILED DESCRIPTION

The technology herein is based on developing an alternative strategy to the efficient production of α-, β-, and ω-functionalized carboxylic acids, alcohols, hydrocarbons, and amines that focuses on the use of type II fatty acid biosynthesis pathway genes/enzymes in *E. coli* and *S. cerevisiae* (as examples) to assemble a functional reversal of the β-oxidation cycle by combining these type II fatty acid biosynthesis enzymes with the non-decarboxylating condensation reaction catalyzed by thiolases. However, these pathways are ubiquitous, and any type II FAS enzyme from any species can be used.

Technologies developed prior to this are based on the native version of the FAS pathway, which uses a decarboxylative condensation step catalyzed by keto-acyl-ACP/CoA synthases. However, the operation of this pathway is less efficient because it consumes ATP in the synthesis of malonyl-ACP, which is the donor of two-carbon units for chain elongation/decarboxylating condensation reaction. As a consequence, the ATP yield associated with the production of products through the FAS pathway is very low. This, in turn, greatly limits cell growth and production of products.

In more detail, the recombinant engineering to make the BOX-R is:

1) Express the Enzymes Required for a Functional β-Oxidation Cycle Reversal Using Enzymes of the Type II Fatty Acid Biosynthesis Pathway. Previously, expression of the β-oxidation cycle was accomplished through an approach in which, first 1) mutations fadR and atoC(c) enable expression of the genes encoding beta oxidation enzymes in the absence of fatty acids; 2) an arcA knockout (ΔarcA) enabled the expression of genes encoding beta oxidation cycle enzymes/proteins under anaerobic/microaerobic conditions (microaerobic/anaerobic conditions are used in the production of fuels and chemicals but lead to repression of beta oxidation genes by ArcA); and 3) replacement of native cyclic AMP receptor protein (crp) with a cAMP-independent mutant (crp*) enabled the expression of genes encoding beta oxidation cycle enzymes/proteins in the presence of a catabolite-repressing carbon source such as glucose (glucose is the most widely used carbon source in fermentation processes and represses the beta oxidation genes).

However, the cycle can also be made to run in reverse by individually overexpressing the rate limiting enzymes as opposed to this regulatory approach. Furthermore, the active enzymes can be purified and combined in vitro and made to run the BOX-R pathway in a test tube or flask, or resting cells could be used as a bioreactor for same.

The overall idea in this disclosure, however is to replace some or all genes (other than the thiolase) with type II FAS enzymes (i.e. 3-oxoacyl-[acyl-carrier-protein] (FabG, others), 3-hydroxyacyl-[acyl-carrier-protein] dehydratase (FabA, FabZ, others), and enoyl-[acyl-carrier-protein] reductase (FabI, FabK, FabL, FabV)).

Thus, for a functional reversal of the BOX-R using type II FAS enzymes, 1) non-decarboxylative thiolase(s) are expressed in combination with 2) 3-oxoacyl-[acyl-carrierprotein]/p-ketoacyl-[ACP] reductase (FabG, others), 3) 3-hydroxyacyl-[acp] dehydratase (FabA, FabZ, others), and 4) enoyl-[acyl-carrierprotein] reductase/enoyl-ACP reductase (FabI, FabK, FabL, FabV) to enable the generation of a diverse set of CoA thioester intermediates (FIG. 1). This approach ensures that the key requirements of a beta-oxidation reversal, non-decarboxylative condensation and the use of CoA thioester intermediates, are preserved even with the use of type II FAS enzymes. See e.g., FIG. 1A.

2) Driving the Beta Oxidation Cycle in the Reverse/Biosynthetic Direction (as Opposed to its Natural Catabolic/Degradative Direction). In addition to functionally expressing the β-oxidation cycle with non-decarboxylative thiolase(s) and type II fatty acid biosynthesis enzymes, we propose the following modifications to improve yields on the reverse operation of this pathway: 1) the use of microaerobic/anaerobic conditions prevents/minimizes the metabolism of acetyl-CoA through the tricarboxylic acids (TCA) cycle and makes acetyl-CoA available to drive the beta oxidation cycle in the reverse/biosynthetic direction; 2) pta (or ackA or both), poxB, adhE, yqhD, and eutE knockouts block/reduce the synthesis of acetate (Δpta or ΔackA and poxB) and ethanol (ΔadhE, ΔyqhD, and ΔeutE) from acetyl-CoA and therefore make acetyl-CoA available to drive the beta oxidation cycle in the reverse/biosynthetic direction; 3) ldhA, mgsA, and frdA knockouts block/reduce the synthesis of lactate (ΔldhA and ΔmgsA) and succinate (ΔfrdA) from pyruvate and phosphoenolpyruvate, respectively, making more phosphoenolpyruvate and pyruvate available for the synthesis acetyl-CoA and therefore making acetyl-CoA available to drive the beta oxidation cycle in the reverse/biosynthetic direction.

3) Conversion of CoA thioester intermediates to the desired end products. Generally speaking, there are several termination enzymes that will pull reaction intermediates out the reverse β-oxidation cycle and produce the desired end product (FIG. 1B-E), and a nonexclusive list is provided in Table C, above.

One or more of these termination enzymes can be overexpressed, as needed depending on the desired end product. The termination enzymes can be native or non-native as desired for particular products, but it may be preferred that the reverse beta oxidation cycle use native genes.

4. Regulation of Product Chain Length. The chain length of thioester intermediates determines the length of end products, and can be controlled by using appropriate termination enzymes with the desired chain-length specificity. Additionally, chain elongation can be inhibited or promoted by reducing or increasing the activity of thiolases with the desired chain-length specificity. These two methods can be used together or independently. For example:

1) knockout of fadA, fadI, and paaJ to avoid chain elongation beyond 1-to-2 turns of the cycle (generates 4- & 6-carbon intermediates and products, or 5- & 7-carbon intermediates and products, depending on the use of acetyl-CoA or propionyl-CoA as primer/starter molecule) and overexpression of the short-chain thiolases yqeF or atoB and short chains alcohol dehydrogenases such as fucO or yqhD for alcohol production for example.

2) overexpression of thiolase(s) of appropriate substrate length specificity (such as *E. coli* atoB, *E. coli* yqeF, *E. coli* fadA, *E. coli* fadI, *Ralstonia eutropha* bktB, *Pseudomonas* sp. Strain B13 catF, *E coli* paaJ, *Pseudomonas putida* pcaF *Rhodococcus opacus* pcaF, *Streptomyces* sp. pcaF, *Ralstonia eutropha* phaA, *Clostridium acetobutylicum* thlA, or *Clostridium acetobutylicum* thlB) to promote chain elongation and overexpression of specific chain length termination pathways such as long-chain thioesterases (such as *E. coli* tesA, tesB, fadM, ybgC or yciA, among others) or long chain alcohol dehydrogenases (such as ucpA, ybbO, yiaY, betA, ybdH or eutG) for carboxylic acid or alcohol production, respectively. The term "appropriate" is used herein to refer to an enzyme with the required specificity toward a given intermediate (i.e. acyl-CoA, enoyl-CoA, hydroxyacyl-CoA, and ketoacyl-CoA) of a specific chain length.

Clomburg et al (2012) focused on bottom-up/synthetic approach to reconstruct a beta-oxidation pathway in reverse ("BOX-R") and hence address short-coming of an early system-level approach that focused on the use of global regulators. Clomburg et al (2012) was successful on identifying and exploiting native enzymes for 3 of the four steps of the BOX-R: thiolase (e.g. AtoB, FadA), 3-hydroxyacyl-CoA dehydrogenase (FadB) and enoyl-CoA dehydratase (fadB). While both of our previous reports (Dellomonaco et al. 2011 and Clomburg et al. 2012) indicate that there is a native *E. coli* enzyme that catalyzes the last step of the BOX-R (trans-enoyl-CoAs to acyl-CoAs), the identity of this enzyme remained elusive.

In this study, we identified fabI-encoded enoyl-CoA reductase as the activity responsible for this conversion and demonstrated that enoyl-ACP reductases of different families can support the efficient operation of an engineered functional reversal of the β-oxidation cycle.

Since acetyl-coA dehydrogenases (ACDH) utilize a bound FAD cofactor to reduce the 2,3 enoyl-CoA bonds, they often require additional enzymes such as flavoproteins and ferrodoxins in order to function, although the initial reducing equivalents may be sourced to NAD(P)H. Because these enzymes utilize FAD molecules, the chemical reduction/dehydrogenation can be considered reversible, though that might not be the practical result in vivo and they are generally considered to be slow enzymes. In contrast to ACDHs, trans-enoyl-CoA reductase (TER) enzymes that directly utilize NAD(P)H molecules to reduce enoyl bonds are considered irreversible reactions as exampled by their inability to oxidize butyryl-CoA substrates (Tucci & Martin, 2007) and do not require electron transfer proteins to function.

This effectively irreversible activity for reduction of crotonyl-CoA by TER-like enzymes has previously been identified as a beneficial property in improving butanol titers (Atsumi et al., 2008; Bond-Watts, Bellerose, & Chang, 2011b; Shen et al., 2011). In addition, modeling studies have shown that *E. coli* engineered for butyrate production by the reversal of β-oxidation cycle would benefit from crotonyl-CoA reduction by enzymes that utilize NADH, given the stoichiometric constraints imposed by the use of ferrodoxins (Cintolesi et al., 2014).

Strains, Plasmids, and Methods

Genomic DNAs from *E. faecalis* V583 (ATCC 700802), *B. subtilis* (Ehrenberg) Cohn (ATCC 23857), and *V. cholerea* N16961 (ATCC 39315), as well as, the *M. elsdenii* Rogosa strain were acquired from ATCC (Manassas, Va.). *E. coli* genomic DNA from MG1655 (Kang et al., 2004) and *M. elsdenii* Rogosa were purified using the Wizard Genomic DNA Purification Kit (PROMEGA™, Madison, Wis.). *E. gracilis* TER was amplified from a plasmid harboring a codon-optimized egTER synthesized by GENSCRIPT™ (Piscataway, N.J.).

All restriction enzymes were purchased from NEW ENGLAND BIOLABS™ (Ipswich, Mass.). Plates were prepared using LB medium containing 1.5% agar, and antibiotics were included at the following concentrations when appropriate: ampicillin (100 µg/mL), kanamycin (50 µg/mL), spectinomycin (50 µg/mL), chloramphenicol (12.5 µg/mL chromosomal/34 µg/mL plasmids) and zeocin (25-50 µg/mL).

Gene overexpression was achieved by cloning the desired gene(s) into either pETDuet-1 (pET) or pCDFDuet-1 (pCDF) (NOVAGEN™, Darmstadt, Germany) digested with NcoI and EcoRI restriction enzymes utilizing In-Fusion PCR cloning technology (CLONTECH LABORATORIES™, Mountain View, Calif.). These vectors have 2 promotors that genes can be cloned behind, referred to herein as P1 and P2.

Cloning inserts were created via PCR of ORFs of interest from their respective genomic or codon-optomized DNA with Phusion DNA polymerase (THERMO SCIENTIFIC™, Waltham, Mass.). The resulting In-Fusion products were used to transform *E. coli* Stellar cells (CLONTECH LABORATORIES™) and PCR identified clones were confirmed by DNA sequencing.

Strain JC01 (MG1655 ΔldhA ΔpoxB Δpta ΔadhE ΔfrdA) (Clomburg, Vick, Blankschien, Rodriguez-moya, & Gonzalez, 2012), a derivative of wild-type K12 *E. coli* strain MG1655 (Kang et al., 2004), was used as the host for all genetic modifications. JC01 (DE3) was constructed from JC01 using a λDE3 Lysogenization Kit (NOVAGEN™) to allow the expression of genes under the T7lac promoter.

Gene knockouts were introduced in JC01 (DE3) and its derivatives by P1 phage transduction (Miller, 1972; Shams Yazdani & Gonzalez, 2008). Single gene knockout mutants from the National BioResource Project (NIG, Japan) (Baba et al., 2006) were used as donors of specific mutations. All mutations were confirmed by polymerase chain reaction and the disruption of multiple genes in a common host was achieved as previously described (Shams Yazdani & Gonzalez, 2008).

Strain JC01 (DE3) was further modified to allow for cumate inducible control (Choi et al., 2010) from the genome. To enable this, first the construction of pUCBB-$P^{CT5}$-ntH6-eGFP based on previous BioBrick™ vector designs (Vick et al., 2011).

*E. coli* atoB and fadB genes were PCR amplified and digested with BglII and NotI and ligated by T4 ligase (Invitrogen, Carlsbad, Calif.) into pUCBB-$P^{CT5}$-ntH6-eGFP that was previously digested with BglII and NotI to produce pUCBB-$P^{CT5}$-atoB and pUCBB-$P^{CT5}$-fadB. The resulting ligation products were used to transform *E. coli* DH5α (INVITROGEN™, Carlsbad, Calif.) and positive clones identified by PCR were confirmed by DNA sequencing.

To integrate the cumate-controlled atoB and fadB constructs onto the chromosome, first the cumate repressor (cymR), promoter/operator regions ($P^{CT5}$), and respective ORFs were PCR amplified, as well as, kanamycin or chloramphenicol drug constructs (respectively via pKD4 and pKD3 (Datsenko & Wanner, 2000). These respective products were linked together via overlap extension PCR to create a final chromosomal targeting construct. Integration of the cumate-controlled constructs was achieved via standard recombineering protocols using strain HME45 and selecting on respective LB drug plates (Thomason et al., 2007).

The gene fadA was separately deleted via recombineering in the HME45 derivative harboring the cumate-controlled fadBA contract by replacement of the fadA ORF with a zeocin-resistance marker amplified from pKDzeo (Magner et al., 2007). All constructs were verified via PCR and sequencing.

All chemicals were obtained from FISHER SCIENTIFIC™ (Pittsburgh, Pa.) and SIGMA-ALDRICH™ (St. Louis, Mo.). Fermentations were conducted as previously described using the identical medium formulation (Clomburg et al., 2012) with the exception of 5.0 μM Isopropyl β-D-1-thiogalactopyranoside (Vector-based expression) and 0.1 mM cumate (chromosomal-based expression) included for induction when appropriate.

Measurement of cell growth, quantification of glycerol and metabolic products by high-performance liquid chromatography (HPLC), quantification of fatty acids (C4-C6) by HPLC, and quantification of fatty acids (C7-C14,C16, C18) by Gas Chromatography—Flame Ionization Detection (GC-FID) were performed as previously described (Clomburg et al., 2012).

For quantification purposes of odd-chain fatty acids, samples were run with and without the C13 fatty acid internal standard, verifying that C13 was not produced. Propionic ($C_{3:0}$), Valeric ($C_{5:0}$), Enanthic ($C_{7:0}$), Pelargonic ($C_{9:0}$) and Undecyclic ($C_{11:0}$) acid (SIGMA-ALDRICH CO.) standards were used to calibrate HPLC and GC-FID analysis.

For measurement of enzymatic activities from fermentation samples, cells were disrupted as previously reported (Dellomonaco, Clomburg, Miller, & Gonzalez, 2011). The HIS Tagged FabI protein was expressed from pCA24N-FabI from the ASKA collection (Kitagawa et al., 2005) in BL21 (DE3) cells (NEW ENGLAND BIOLABS™) induced at $OD_{600}≈0.4$ with 0.1 mM IPTG and shaken O/N at Room Temperature. FabI protein was harvested and purified as previously reported using Talon Metal Affinity Resin (CLONTECH LABORATORIES™) (Clomburg et al., 2012).

Thiolase activity (Wiesenborn, Rudolph, & Papoutsakis, 1988) and β-hydroxybutyryl-CoA dehydrogenase activity (Bond-Watts, Bellerose, & Chang, 2011a) were monitored accordingly as previously described (Clomburg et al., 2012). Trans-enoyl-CoA reductase activity for egTER, FabI, bsFabL, efFabK and vcFabV were monitored by loss of NADH (Bond-Watts et al., 2011a; Clomburg et al., 2012). Acyl-CoA dehydrogenase activity was monitored by measuring the reduction of Methyl-Thiazolyl Blue (MTT) coupled to the oxidation of butyryl-CoA (O'Brien & Frerman, 1977) in cellular extracts disrupted as above with the addition of 5 μM flavin adenine dinucleotide (FAD).

Reactions conditions were as follows: 25 mM Tris pH 7.5, 240 μM MTT, 1.7 mM phanazine methosulfate (PMS), 15 mM sodium cyanide, and 250 μM butyryl-CoA in a final volume of 200 μL at 30° C. All substrates and chemicals for enzyme assays were obtained from FISHER SCIENTIFIC™ and SIGMA-ALDRICH™.

High performance liquid chromatography-mass spectrometry (HPLC-MS) was performed on a BRUKER™ MicroTOP ESI (Fremont, Calif.) with an AGILENT™ 1200 HPLC System (Santa Clara, Calif.). Enzymatic reactions were quenched with 10% of IN HCl and diluted 10 fold with $dH_2O$, 2 μL of which was used for injection. HPLC-MS assays were performed using a SHIMADZU™ Shim-pack XR-ODS II column (2.0 mm I,d.×75 mm) (Tokyo, Japan) at a flow rate of 0.15 mL/min with a maximum pressure of 380 bar at room temperature. Liquid chromatography was performed with 40 mM ammonium acetate (Buffer A) and methanol (Buffer B). The time course was as follows: 0 min-2.5% methanol, linear gradient to 70% methanol at 7 min, hold at 70% methanol to 12 min, linear gradient to 2.5% methanol at 12.1 min, hold at 2.5% methanol to 24 min.

Chromosomal Expression

Previously, an engineered reversal of BOX-R was constructed in *E. coli* by utilizing strain JC01, a fermentation-deficient derivative of *E. coli* K12 strain MG1655 (MG1655 ΔldhA ΔpoxB Δpta ΔadhE ΔfrdA), with the vector level expression of native thiolase (AtoB), 3-hydroxyacyl-CoA dehydrogenase (FadB), and enoyl-CoA hydratase (FadB), as well as the foreign trans-enoyl-CoA reductase from *Euglena gracilis* (egTER) (Clomburg et al., 2012).

An interesting result of this work was the ability to produce small amounts of butyrate in the absence of an overexpressed acyl-CoA dehydrogenase (ACDH) or trans-enoyl-CoA reductase (TER). Using strain JC01 with the pTH.atoB.fadB vector, the two main products from the reversal of the β-oxidation cycle were 3-hydroxybutyrate (3-HB) (2.5 g/L) and butyrate (0.2 g/L). When *E. gracilis* trans-enoyl-CoA reductase (egTER) is overexpressed via pTH.atoB.fadB.egTER, a 17-fold increase in butyrate production is observed (3.4 g/L) while virtually eliminating production of the 3-hydroxybutyrate (Clomburg et al., 2012).

The product profile can then be altered to longer-chain carboxylic acids (up to C12) with the inclusion of a longer chain specific thiolase (FadA). This work clearly established thiolases (AtoB, FadA), 3-hydroxyacyl-Coa dehydrogenase (FadB), and enoyl-CoA dehydratase (FadB) as key native enzymes necessary to facilitate the functional reversal of β-oxidation (FIG. 1). However, the identity of native ACHD or TER-like enzyme(s) reported to be able to catalyze the conversion of enoyl-CoA to acyl-CoAs (Clomburg et al., 2012; Dellomonaco et al., 2011) was elusive.

In order to establish a clean, vector-free platform to identify the unknown native ACDH or TER-like enzymes that catalyze the final step of the β-oxidation reversal, we constructed a strain with tunable chromosomal expression of AtoB and FadB by engineering their native chromosomal loci. Using an in-house developed expression system based on a cumate-inducible promoter (Choi et al., 2010) adapted into a BioBrick vector system (Vick et al., 2011), atoB and fadB genomic level expression was altered to be controlled by cumate while the fadA gene was knocked out.

For atoB and fadB, the native promoter was replaced by both the T5 promoter controlled by the CymR operator (CT5) as well as an upstream constitutive expression system for CymR. By removing FadA expression, butyrate production can be utilized as proxy for flux through a single turn of the reversal of β-oxidation cycle, thus facilitating the identification of native enzyme(s) responsible for the reduction of crotonyl-CoA.

Prior to the aforementioned modifications, strain JC01 was modified to include the DE3 cassette to allow the use of Novagen's Duet vector system for the expression of hypothesized ACDHs and TER-like enzymes. The resulting strain will be referred to throughout the manuscript as JC01(DE3) atoB$^{CT5}$ fadB$^{CT5}$ ΔfadA.

Enzyme activities and fermentation profiles of JC01 (DE3) atoB$^{CT5}$ fadB$^{CT5}$ ΔfadA were compared to those of the vector-based expression system in strain JC01(DE3) [pETDuet-atoB pCDFDuet-fadB]. The chromosomal expression strain produced more butyrate (0.63±0.01 g/L) and 3-hydroxybutyrate (4.33±0.04 g/L) than the vector based system (butyrate=0.42±0.03 g/L, 3-hydroxybutyrate=3.23±0.07 g/L) (data not shown). The chromosomal strain had similar 3-hydroxybutyryl-CoA dehydrogenase activity (2.2±0.7 μmol/mg/min) to that of pCDFDuet-fadB (1.7±0.7 μmol/mg/min) while thiolase activity was greater from pETDuet-atoB (25.0±3.2 μmol/mg/min) in comparison to atoB expression from the chromosome (3.8±0.3 μmol/mg/min). The higher product yield from JC01(DE3) atoB$^{CT5}$ fadB$^{CT5}$ ΔfadA indicates that adequate amounts of thiolase and 3-hydroxybutryl-CoA dehydrogenase activities are produced by chromosomal expression.

Identification of Native Enzyme(s)

Figure 1A:
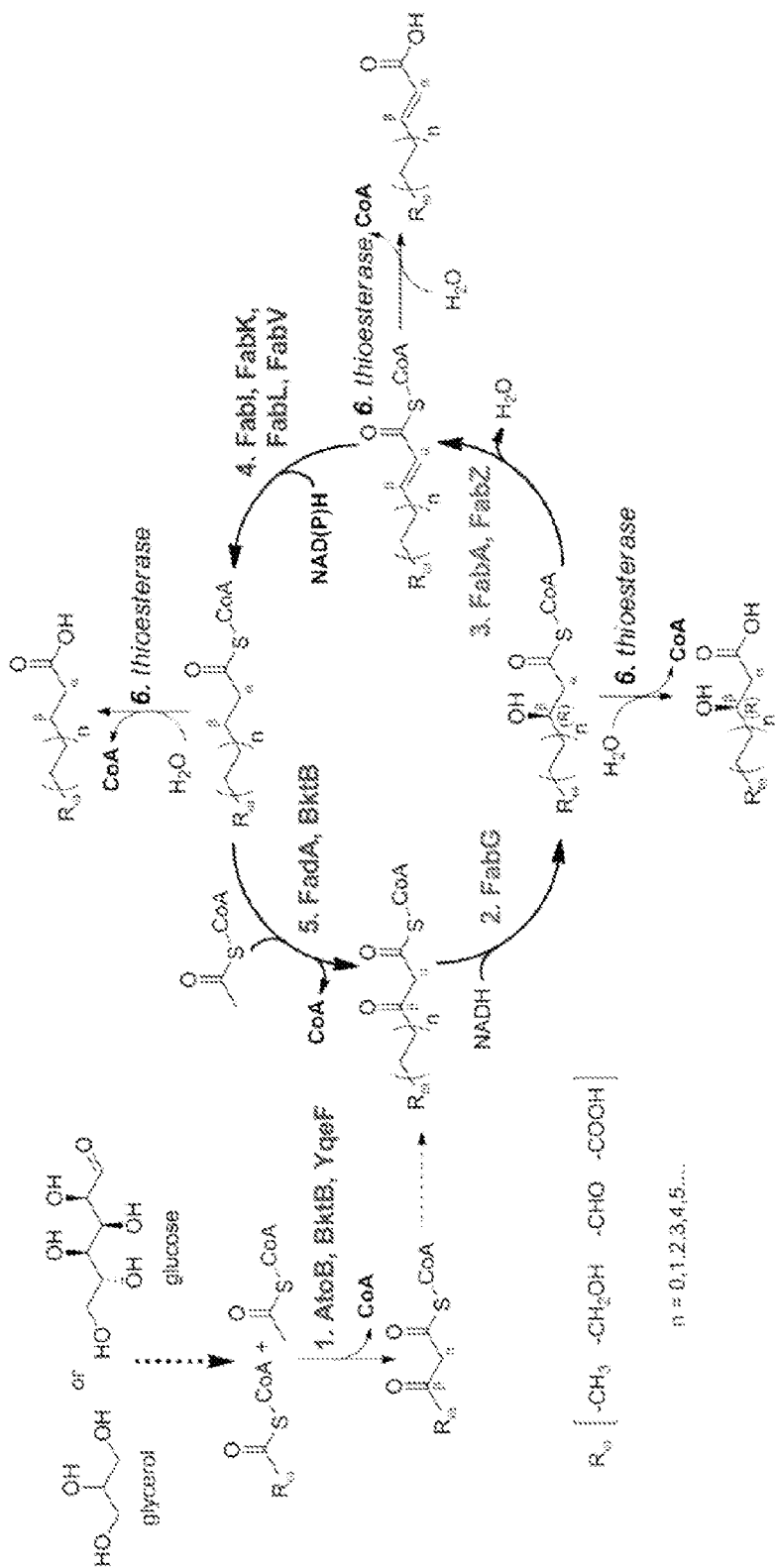
FIG. 1A. Modified BOX-R cycle with type II fatty acid biosynthesis enzymes. AtoB, BktB, YqeF, FadA: example of overexpressed thiolases that catalyze the non-decarboxylative condensation of an acyl-CoA primer with 2-carbon donor acetyl-CoA to produce a β-ketoacyl-CoA; FabG: example of overexpressed 3-oxoacyl-[acyl-carrier-protein] reductase that catalyzes the reduction of a β-ketoacyl-CoA to a (3R)-β-hydroxyacyl-CoA; FabA, FabZ: example of overexpressed 3-hydroxyacyl-[acyl-carrier-protein] dehydratases that catalyzes the dehydration of a (3R)-β-hydroxyacyl-CoA to a trans-enoyl-CoA; FabI, FabK, FabL, FabV: example of overexpressed enoyl-[acyl-carrier-protein] reductases that catalyzes the reduction of a trans-enoyl-CoA to an acyl-CoA; Thioesterase: example of overexpressed termination pathway.
Figure 1B:
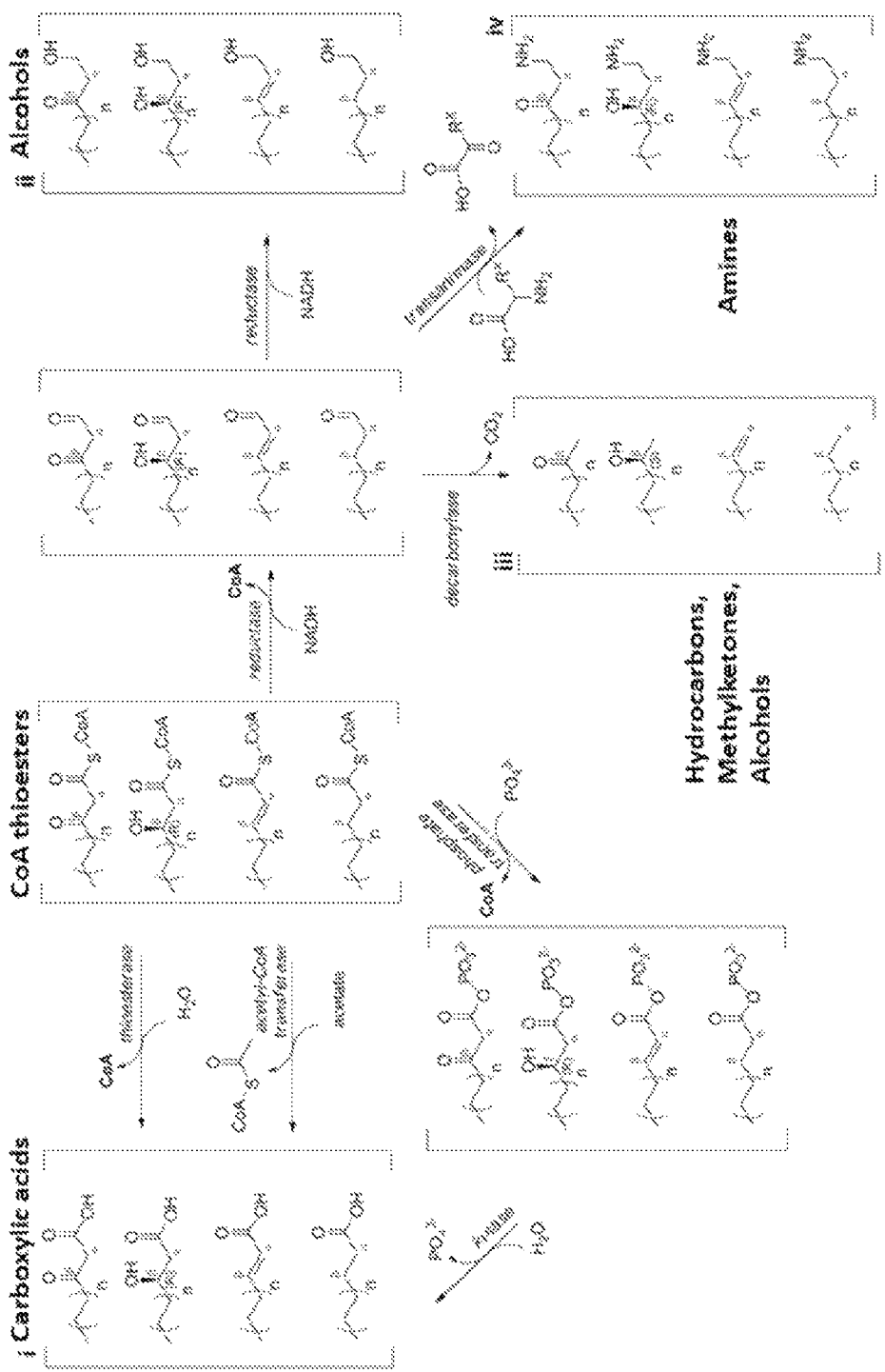
FIG. 1B. Primary termination pathways. Pathways that act on the CoA thioester group/carbon, resulting in the synthesis of i) carboxylic acids, ii) primary alcohols, iii) hydrocarbons, and iv) n primary amines, along with their β-hydroxy, β-keto, and α,β-unsaturated derivatives are illustrated.
Figure 1C:
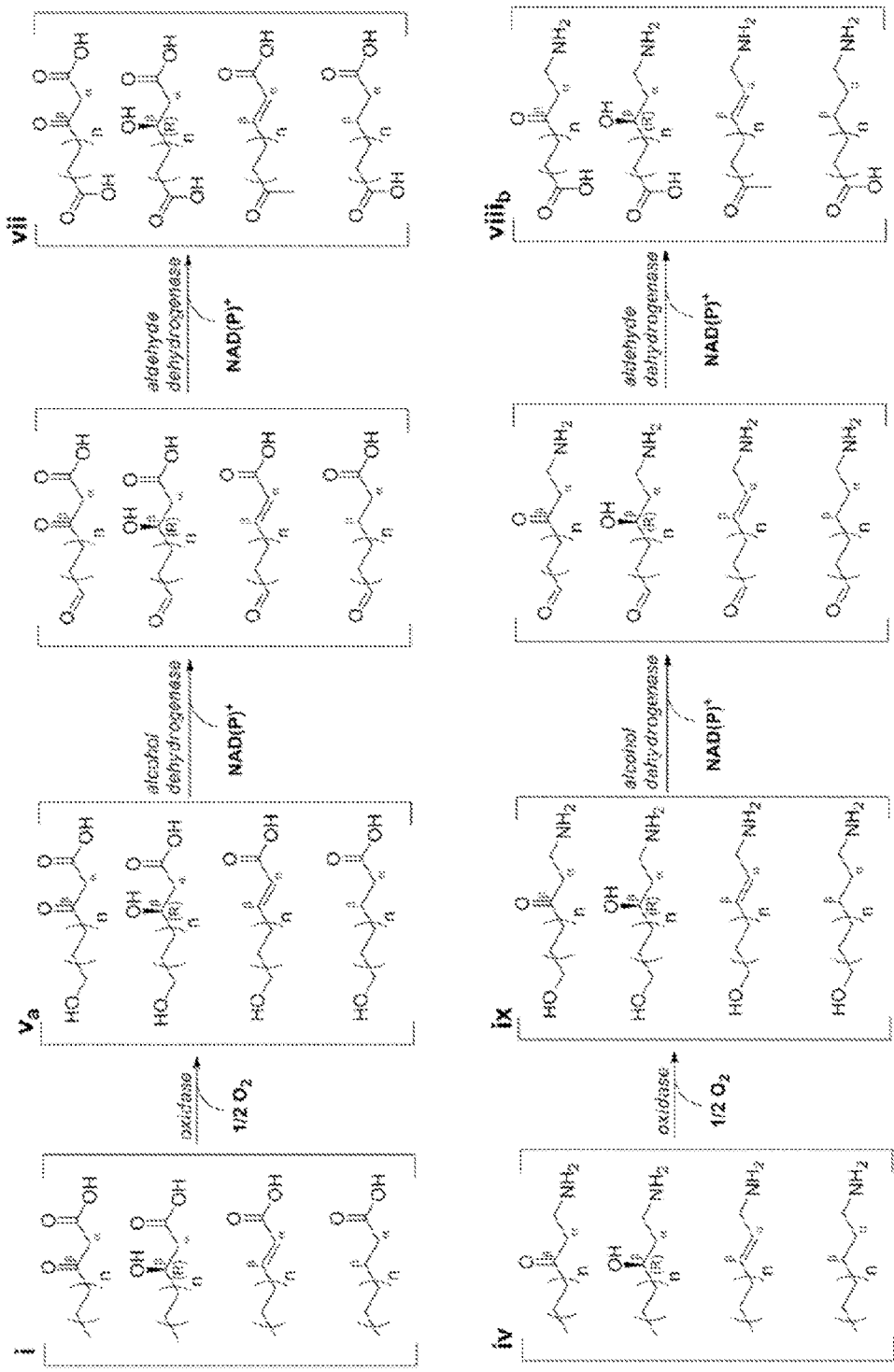
FIG. 1C. Secondary termination pathways continuing from the primary pathways shown in FIG. 1B. Pathways for the production of omega-hydroxylated carboxylic acids (va), dicarboxylic acids (vii), omega-hydroxylated primary amines (ix), and omega carboxylic acid primary amines (viiib) along with their β-hydroxy, β-keto, and α,β-unsaturated derivatives from the carboxylic acids (i) and primary amines (iv) generated from BOX-R with primary termination pathways are illustrated.
Figure 1D:
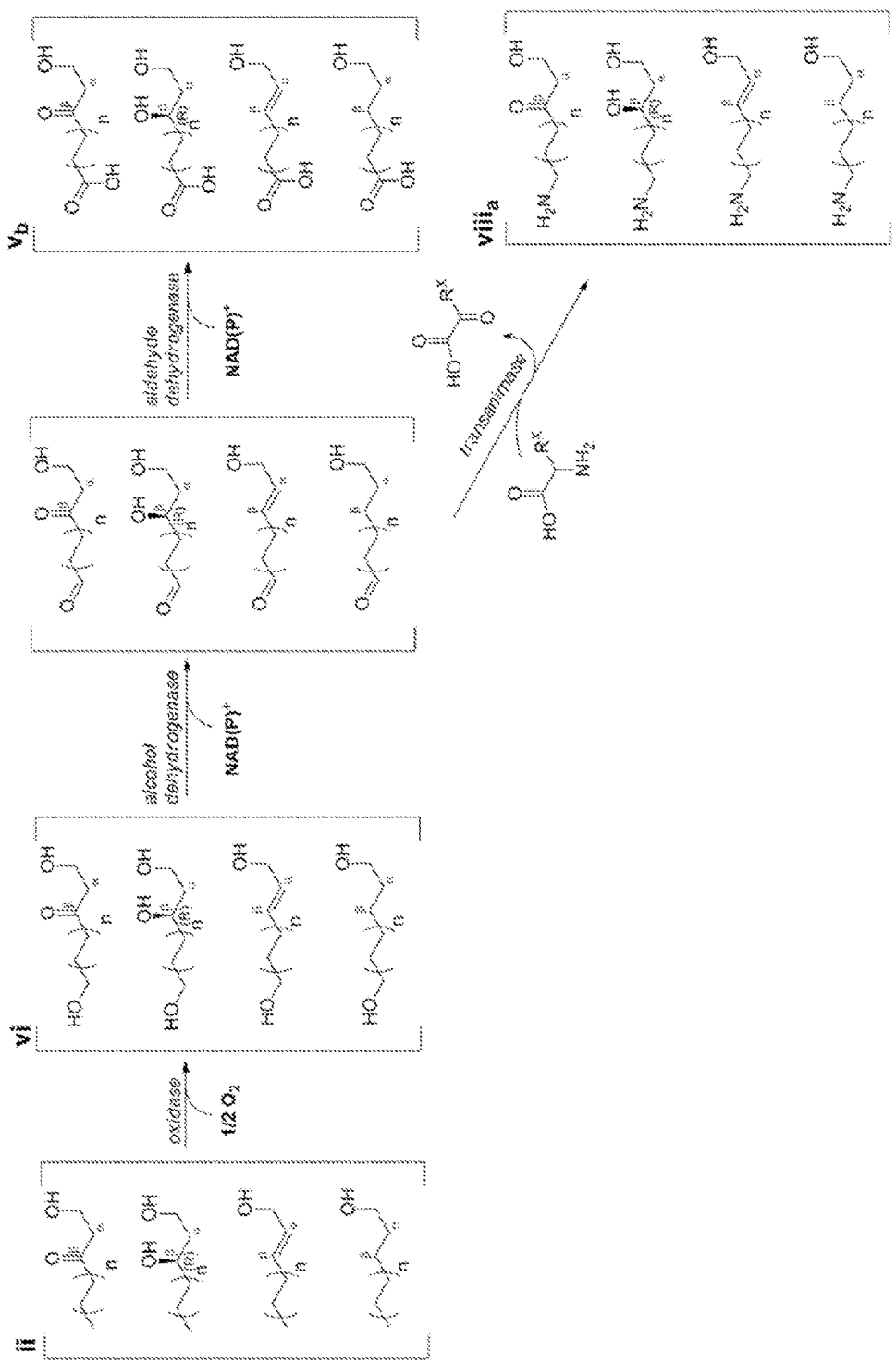
FIG. 1D. Secondary termination pathways. Pathways for the production of omega-hydroxylated primary alcohols (vi), omega carboxylic acid primary alcohols (vb), and omega amino primary alcohols (viiia) along with their β-hydroxy, β-keto, and α,β-unsaturated derivatives from the primary alcohols (ii) generated from BOX-R with primary termination pathways are illustrated.
Figure 1E:
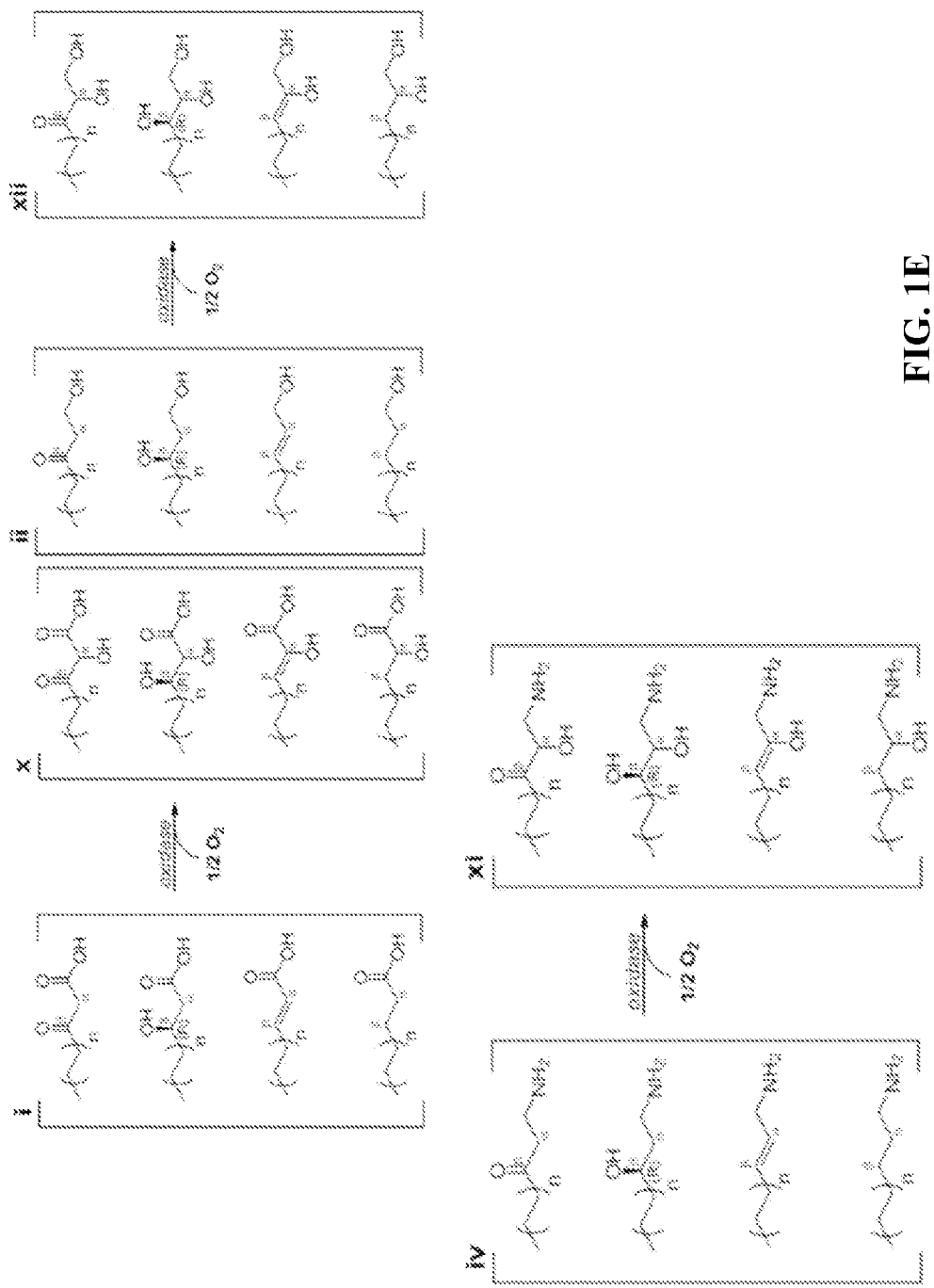
FIG. 1E. Secondary termination pathways. Pathways for the production of alpha-hydroxylated carboxylic acids (x), alpha-hydroxylated primary alcohols (xii), and alpha-hydroxylated primary amines (xi) along with their β-hydroxy, β-keto, and α,β-unsaturated derivatives from the carboxylic acids (i), primary alcohols (ii), and primary amines (iv), generated from BOX-R with primary termination pathways are illustrated.
Figure 2:
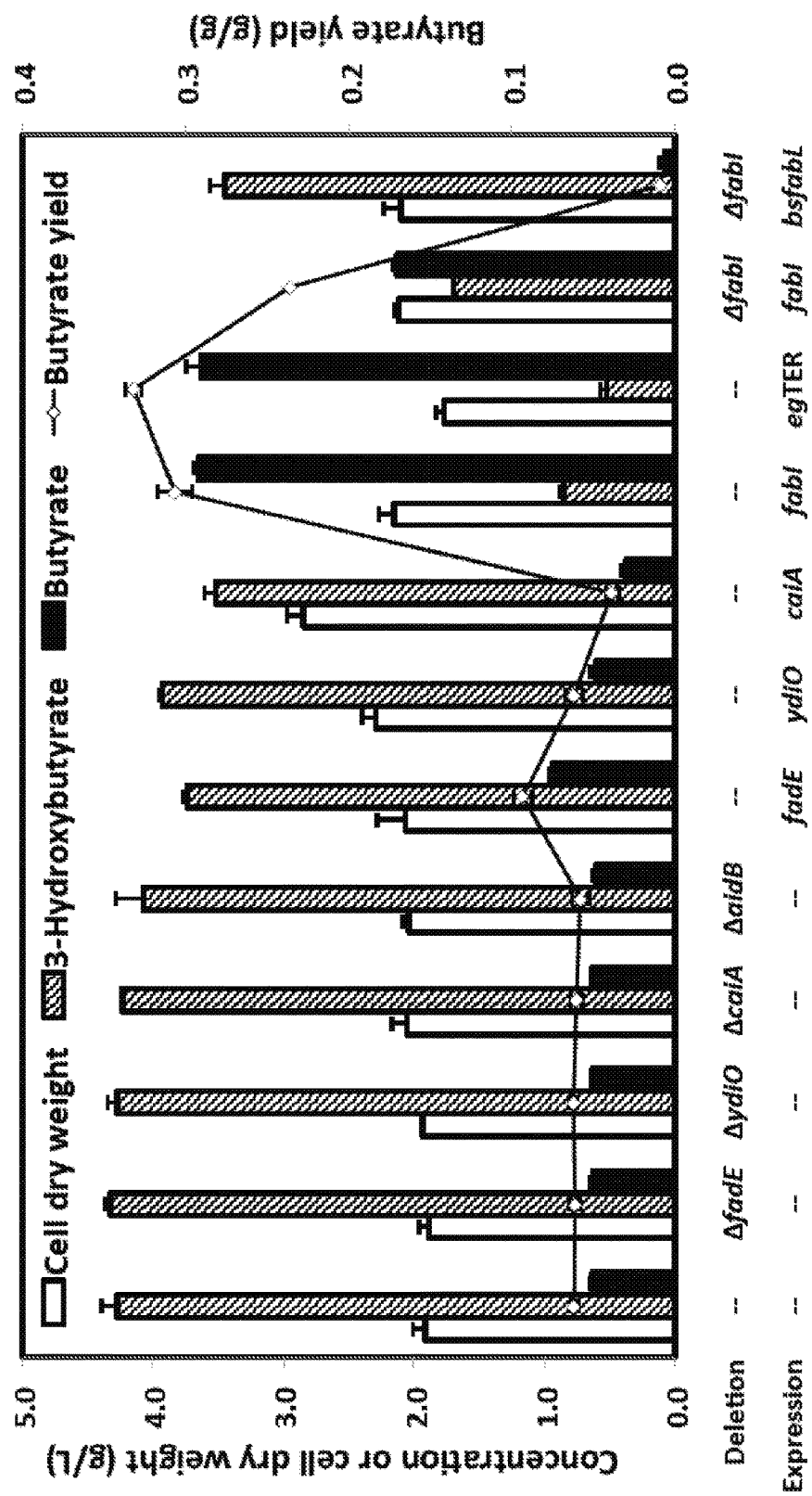
FIG. 2. Impact of deletion and over-expression of genes encoding enzymes potentially responsible for the reduction of crotonyl-CoA on cell growth and product synthesis by strain JC01(DE3) atoB$^{CT5}$ fadB$^{CT5}$ ΔfadA. Chromosomal gene deletions (Δ"gene") or plasmid based (vector pET-Duet) gene overexpression are indicated. Strain JC01 is a fermentation-deficient derivate of E. coli MG1655 containing the following gene deletions: ΔldhA, ΔpoxB, Δpta, ΔadhE, and ΔfrdA.

Multiple enzymes in *E. coli* have the potential to reduce a 2,3-trans enoyl-CoA (e.g. crotonyl-CoA) to the corresponding acyl-CoA (e.g. butyryl-CoA). *E. coli* has two reported ACDHs as part of β-oxidation pathways. FadE is the reported aerobic ACDH (Campbell & Jr, 2002; O'Brien & Freman, 1977) while YdiO is a member of a butyryl-CoA dehydrogenase (BCD) electron transfer protein (Etf) complex (BCD/EtfBA) necessary for growth on fatty acids under anaerobic conditions (Campbell 2003). Two additional ACDH enzymes are present that could potentially reduce crotonyl-CoA as a promiscuous substrate; the crotonobetaine reductase complex CaiAB (Elssner 1999) and AidB, the isovaleryl-CoA dehydrogenase (Landini 1994; Rohankhedkar 2006), although AidB is reported to not work on butyryl-CoA. In an attempt to identify the native enzyme reducing crotonyl-CoA, the genes encoding these ACDH enzymes were knocked out and their effect on butyrate production in JC01(DE3) atoB$^{ct5}$ fadB$^{ct5}$ ΔfadA was assessed. Interestingly, the individual deletion of these enzymes had little impact on either butyrate or 3-HB production levels (FIG. 2).

The genes encoding the aforementioned ACDHs were deleted and overexpressed in strain JC01(DE3) atoB$^{CT5}$ fadB$^{CT5}$ ΔfadA and their effect on butyrate production assessed. The deletions had little impact on either butyrate or 3-hydroxybutyrate production levels and did not impair growth (FIG. 2). The only ACDH over-expression that affected butyrate yield was FadE, which resulted in a 44% increase in comparison to a control with the pETDuet vector alone (FIG. 2). Similarly, only the overexpression of FadE resulted in a change in measurable dehydrogenase activity on butyryl-CoA with a specific activity of 0.019±0.0017 μmol/mg/min, which is an order of magnitude greater than any other tested (Table 3). Since deletion or overexpression of ACDHs did not result in significant changes to butyrate levels when combined with AtoB and FadB overexpression, alternative candidates for enzymes catalyzing the conversion of crotonyl-CoA to butyryl-CoA were explored.

Given the advantageous nature of TER enzymes and the fact that none of the investigated ACDH enzymes significantly altered butyrate production, another potential native enzyme that can catalyze the NAD(P)H-dependent conversion of crotonyl-CoA to butyryl-CoA is FabI, an essential enzyme from the fatty acid biosynthesis pathway (Heath & Rock, 1995). Although the fatty acid biosynthesis pathway utilizes Acyl Carrier Proteins (ACP) as substrates, FabI has been demonstrated to reduce crotonyl-CoA to butyryl-CoA (Helmut Bergler, 1996; Weeks & Wakil, 1968).

Despite the potential for the native enzyme, when crude extracts from JC01(DE3) atoB$^{ct5}$ fadB$^{ct5}$ ΔfadA were assayed for NAD(P)H dependent reduction of crotonyl-CoA no detectable activity was observed (Table 1). However, this is not necessarily an unexpected result, as FabI only reduces crotonyl-CoA as a promiscuous substrate with a $K_M$ (2.7 mM) (Helmet Bergler 1994) that is roughly 30-fold higher than the concentration of crotonyl-CoA (80 μM) used in the standard assay of trans-enoyl-CoA reductases (80 μM crotonyl-CoA) (Bond-Watts 2011a).

To better assess the potential involvement of FabI, the trans-enoyl-CoA reductase assay was performed using 1 mM crotonyl-CoA, a concentration that is similar to the reported $K_M$ of 2.7 mM. Utilizing this substrate concentration, NADH-dependent crotonyl-CoA reduction activities of 0.100±0.001 μmol/mg/min and 0.080±0.007 μmol/mg/min were observed in crude cell extracts from fermentation samples of JC01(DE3) atoB$^{ct5}$ fadB$^{ct5}$ ΔfadA harvested at 8 hrs and 48 hrs, respectively (Table 1). These results revealed the potential involvement of FabI in butyrate production from a one-turn reversal of the β-oxidation cycle.

To further investigate the potential role of FabI, vectors containing fabI or egTER were constructed and transformed into JC01(DE3) atoB$^{cT5}$ fadB$^{cT5}$ ΔfadA to assess butyrate production from a one-turn BOX-R. In FIG. 2 FabI overexpression resulted in significant increase in butyrate production compared to that with only AtoB and FadB expression. Even more surprising, the overexpression of FabI resulted in butyrate production at levels comparable to egTER overexpression (3.66 g/L and 3.64 g/L, respectively), while also showing similar reduction in 3-hydroxybutyrate levels (to 0.9 and 0.5 g/L respectively) (FIG. 2). When comparing the trans-enoyl-CoA reductase activities of these fermentations samples (using the standard 80 µM crotonyl-CoA), fabI-overexpressing cultures showed six times lower activity than the activity observed upon egTER-overexpression (Table 2). Despite these lower levels of activity, the comparable levels of butyrate production with either fabI or egTER overexpression demonstrates the potential of an enoyl-ACP reductase from the type II fatty acid biosynthesis pathway to function with CoA intermediates in the context of a reversal of the β-oxidation cycle.

In order to provide further evidence that promiscuous crotonyl-CoA reduction by FabI is involved in native BOX cycle, fabI deletion is required. Given the essential nature of FabI (this is the only ENR in $E.\ coli$), construction of a ΔfabI strain requires complementation with another trans-enoyl-ACP activity. Moreover, to verify the hypothesis that FabI indeed functions as the enoyl-CoA reductase of the BOX-R, the complementing enoyl-ACP reductase should not promiscuously reduce crotonyl-CoA as well. Since no enoyl-ACP reductase has been reported with these explicit characteristics, we investigated the following representative members of bacterial ENR families for their lack of crotonyl-CoA reductase activity: $Bacillus\ subtilis$ FabL (bsFabL) (Heath 2000), $Enterococcus\ faecalis$ FabK (efFabK) (Bi 2014, Zhu 2013), and $Vibrio\ cholerae$ FabV (vcFabV) (Massengo-Tiasse 2008).

Genes encoding each of the aforementioned ENRs were cloned into pETDuet and the resulting vectors transformed into JC01(DE3) atoB$^{CT5}$ fadB$^{CT5}$ ΔfadA, and the resulting strains assayed for crotonyl-CoA reductase activity using 80 µM crotonyl-CoA. While detectable activity was measured for cells with efFabK or vcFabV, no activity was detected for the cells overexpressing bsFabL (Table 1). Even when assayed with 1 mM crotonyl-CoA, the levels of crotonyl-CoA reductase activity shown by cell extracts of JC01(DE3) atoB$^{CT5}$ fadB$^{CT5}$ ΔfadA ΔfabI [pETDuet-bsfabL] are similar to the background levels measured for JC01(DE3) atoB$^{CT5}$ fadB$^{CT5}$ ΔfadA [pETDuet], making bsfabL an ideal candidate to complement a fabI deletion without also providing the ability to promiscuously reduce crotonyl-CoA. As such, JC01(DE3) atoB$^{CT5}$fadB$^{CT5}$ ΔfadA ΔfabI strains were constructed in the presence of either pETDuet fabI or pETDuet-bsfabL. These vectors complemented the fabI deletion equally well, as evidenced by the isolation of viable transductions as well as the similar growth of both strains during fermentations (FIG. 2). However, significant differences in butyrate production (FIG. 2) and enoyl-CoA reductase activity (Table 1) were observed between the two strains. JC01 (DE3) atoB$^{CT5}$fadB$^{CT5}$ ΔfadA ΔfabI [pETDuet fabI] still produced large amounts of butyrate and exhibited enoyl-CoA reductase activity, characteristics not observed with JC01(DE3) atoB$^{CT5}$ fadB$^{CT5}$ ΔfadA ΔfabI [pETDuet-bsfabL]. These results strongly support the hypothesis that FabI is the unknown enzyme responsible for enoyl-CoA reduction in the experiments discussed above and as such could also have played a role in product synthesis through the previously engineered BOX-R cycle in $E.\ coli$ (Clomburg 2012, Delmonaco 2011).

When assayed with NADPH, FabI is able to reduce enoyl-ACPs at an optimum of pH 6.5 on chain lengths of C4 to C10, while not able to reduce enoyl-CoAs. With NADH, FabI has a broader pH range for enoyl-ACP reduction that is optimal at pH 7.5 and is active over a chain length from C4 to C16. NADH is also necessary for FabI to reduce CoA substrates, though the reported catalytic efficiency with crotonyl-CoA ($k_{cat}/K_M$=8.52×10$^1$ M$^{-1}$ sec$^{-1}$) is several orders of magnitude lower than that reported with crotonyl-ACP ($k_{cat}/K_M$=1.91×10$^6$M$^{-1}$ sec$^{-1}$) at pH 7.5.

The low catalytic efficiency reported for FabI with crotonyl-CoA contrasts with our observation that this enzyme supports butyrate synthesis fluxes as high as those supported by egTER, an enzyme with a very high catalytic efficiency with crotonyl-CoA ($k_{cat}/K_M$=1.2±0.1 M$^{-1}$ sec$^{-1}$) (Clomburg et al., 2012). A comparison of crotonyl-CoA reduction activity observed in our cultures to the expected activity based on reported kinetic parameters (Helmet Bergler et al., 1994) revealed an interesting picture. After 8 hours of cultivation, strain JC01(DE3) atoB$^{ct5}$ fadB$^{ct5}$ ΔfadA exhibited an NADH-dependent crotonyl-CoA reduction activity of 0.100±0.001 µmol/mg/min, which corresponds to an observed rate of 4.88×10$^{-8}$ M s$^{-1}$. The total protein concentration of the same culture was 2.94 mg/mL, from which the concentration of FabI is estimated to be between 6.83×10$^{-8}$ M and 6.83×10$^{-12}$M (Ishihama et al., 2008). Considering this concentration of FabI in the culture, the reported kcat (0.23 s$^{-1}$) and Km (2.7 mM) (Helmet Bergler et al., 1994), and a 1 mM crotonyl-CoA concentration, the expected rate of crotonyl-CoA reduction by FabI was calculated to be between 7.86×10$^{-13}$M s$^{-1}$ and 7.86×10$^{-9}$M s$^{-1}$. These calculations indicate that the expected rate calculated from reported kinetic parameters is only a small fraction of the rate observed in our cultures, which warrants re-evaluation of the kinetic parameters of FabI using crotonyl-CoA as the substrate.

Figure 3:
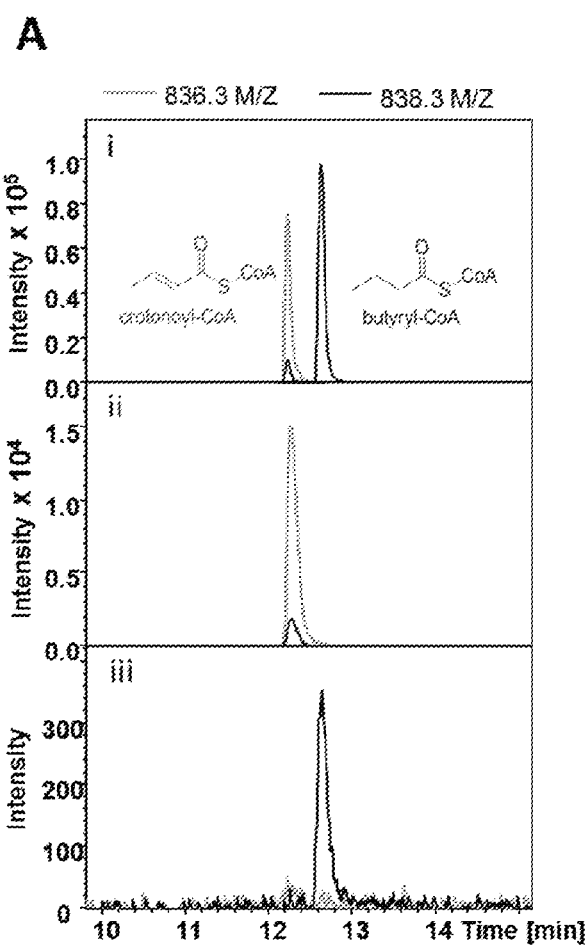
FIG. 3. Characterization of crotonyl-CoA reduction to butyryl-CoA by FabI.

N-terminal His-tagged FabI was purified from an ASKA collection vector (Kitagawa et al., 2005) expressed in the strain BL21(DE3). The purified enzyme had a $K_M$ (4.6±0.6 mM) quite similar to the reported $K_M$ of 2.7 mM (Helmet Bergler et al., 1994), but our measurement of $k_{cat}$ was 5.3±0.6 s$^{-1}$ in comparison to 0.23 s$^{-1}$ that was previously reported, resulting in a 13-fold improvement of catalytic efficiency ($k_{cat}/K_M$) from 8.52×10$^1$ M$^{-1}$ sec$^{-1}$ to 1.15×10$^3$. This change in $k_{cat}$ increases the expected rate of crotonyl-CoA reduction by FabI to a value between 1.02×10$^{-7}$M s$^{-1}$ and 7.86×10$^{-11}$ M s$^{-1}$, which is in agreement with the rate observed in our cultures. To verify that FabI is utilizing NADH to convert crotonyl-CoA to butyryl-CoA, the reaction was monitored via HPLC-MS, which confirmed that FabI converts crotonyl-CoA almost completely to butyryl-CoA (FIG. 3$a$).

Factors such as the presence of Mg$^{2+}$ during our purification as well as Trisma-HCl vs. phosphate based buffer systems had marginal effect on activity levels (data not shown), and the most likely cause for this discrepancy is that previous studies used a maximum of approximately 1.25 mM crotonyl-CoA, which is less than their reported $K_M$ indicating that there was an inaccurate estimation of $V_{max}$.

As an essential gene for FAS, FabI is inhibited when large amounts of palmitic acid (C16) is present, and has been demonstrated to have a $K_i$ of 5.4 µM towards palmitoyl-ACP and 20 µM towards palmitoyl-CoA, but this inhibition is quickly lost for shorter fatty acids as the $K_i$ for decaonyl-CoA is approx 900 µM (Helmut Bergler 1996).

Figure 3B:
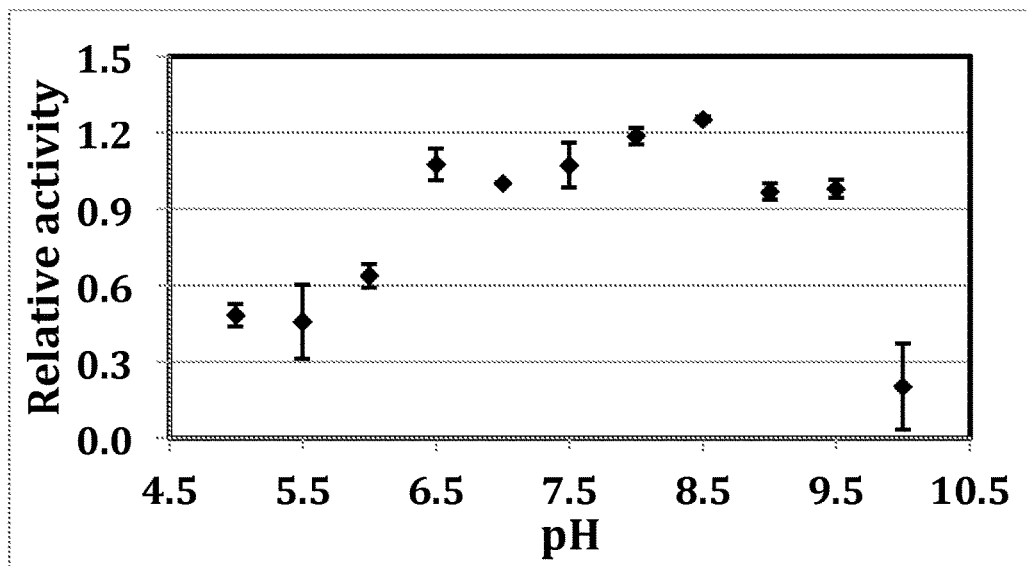
FIG. 3B. pH activity profile of FabI with crotonyl-CoA and NADH relative to pH 7.5 (1.0).

To understand the potential of utilizing FabI for BOX-R, we examined the effect of key CoA thioester intermediates of the BOX-R as well as a broad range of acyl-CoAs on FabI activity (FIG. 3B). Palmitoyl-CoA demonstrated close to 50% inhibition at 20 µM, while myristoyl-CoA (C14) had the highest percent inhibition at 200 µM. The shorter acyl- CoAs thioesters, acetoacetyl-CoA and 3-hydroxy-butyryl-CoA demonstrated minimal inhibitory effects.

Figure 3C:
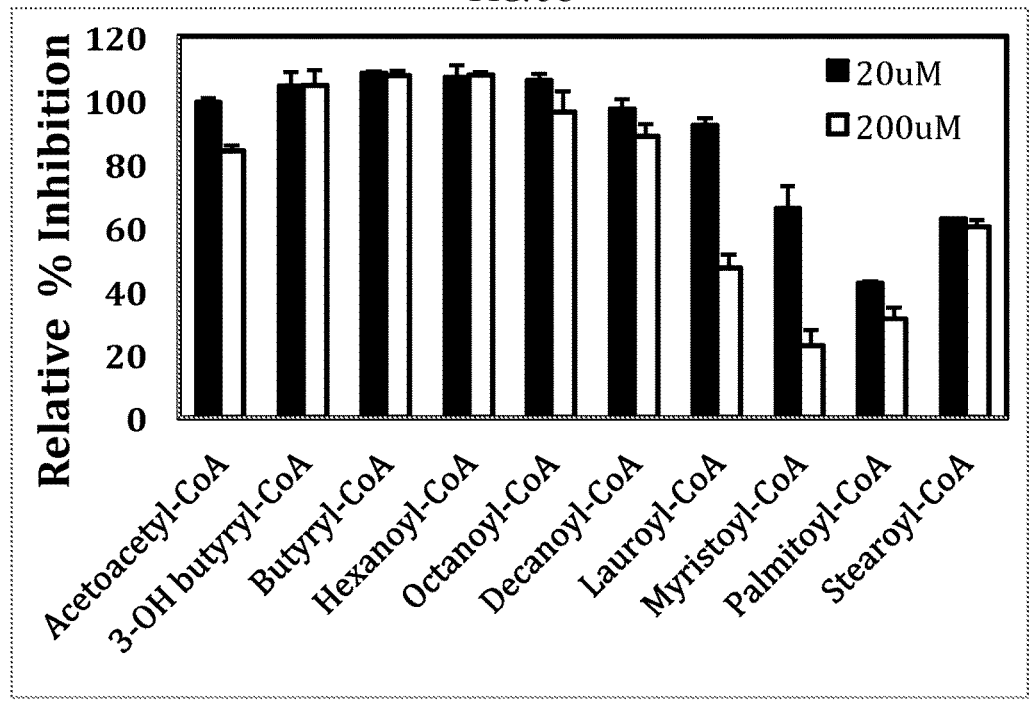
FIG. 3C. Inhibition profile of crotonyl-CoA reduction activity for FabI with the indicated CoA thioesters at either 20 or 200 µM relative to activity in absence of inhibitor (100%).

The pH profile for FabI was also examined for comparison to the reported profile for crotonyl-ACP (Weeks & Wakil, 1968) (FIG. 3C). Using crotonyl-CoA, FabI has a broad range of activities from pH 5.5 up to 9.0. This range is not dissimilar to the reported pH range with crotonyl-ACP, although the optimal pH switched to pH 6.5 and the enzyme remained active at higher pHs.

FABI Supports Synthesis of C>4 Carboxylic Acids

Figure 4A:
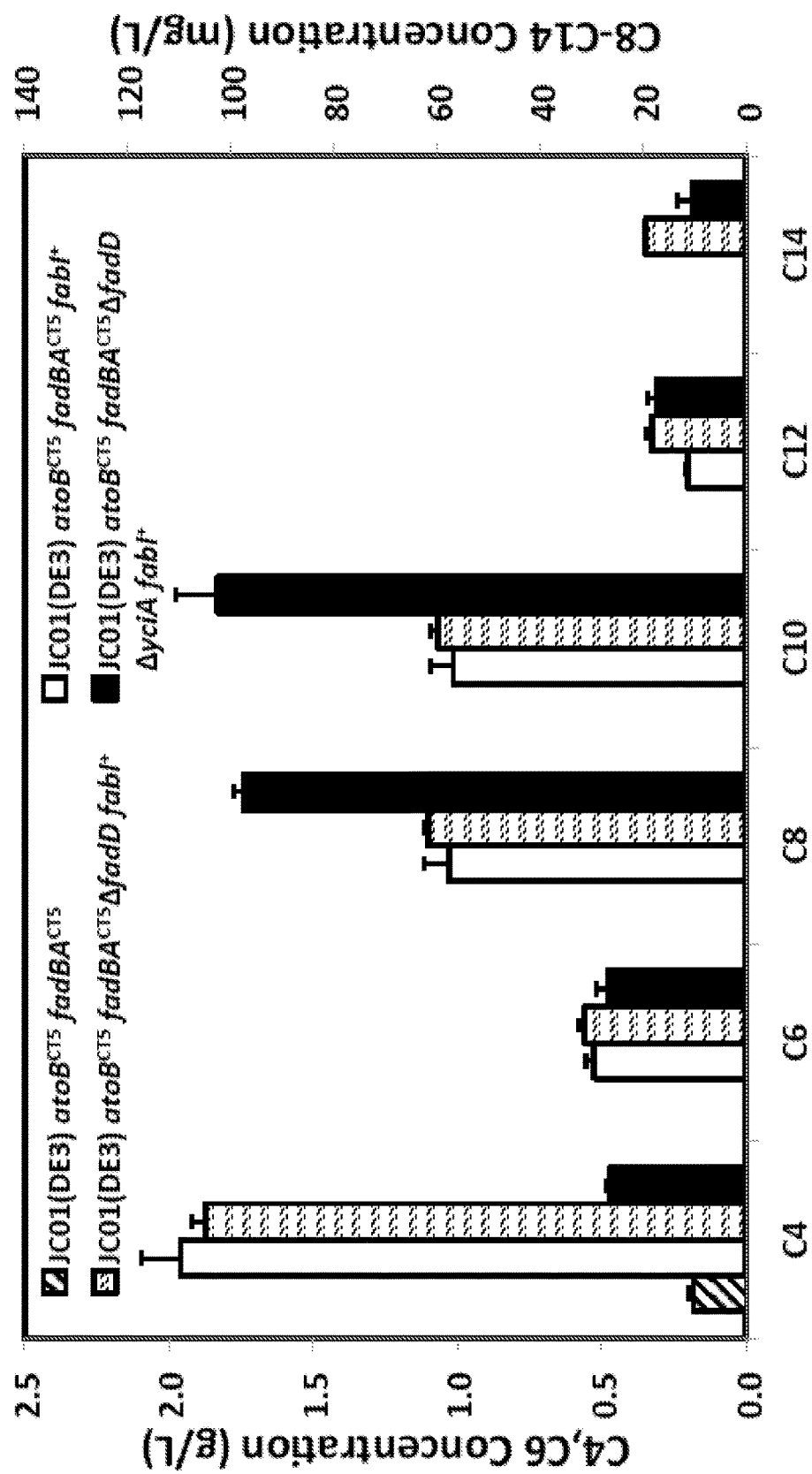
FIG. 4A-B. Synthesis of longer chain carboxylic acids via multiple turns of a BOX-R using FabI as the enoyl-CoA reductase.

Employing AtoB as the thiolase limits the operation of the BOX-R pathway to one cycle and product synthesis to C4 molecules. FadA, which has longer chain length specificity, produces longer chain products. When fabI is overexpressed from pETDuet in JC01(DE3) atoB$^{CT5}$ fadBA$^{CT5}$, the production of extracellular longer chain length carboxylic acids is observed (FIG. 4A). The most abundant carboxylic acid produced is C6 (0.53±0.03 g/L), while C8, C10 and C12 carboxylic acids are produced at 57.8±4.7, 56.8±4.4 and 11.5±0.3 mg/L, respectively (FIG. 4A).

The deletion of fadD has been utilized in numerous studies to facilitate the accumulation of longer chain carboxylic acids by preventing the uptake of free fatty acids from the media (Lennen 2012). Under these conditions, the deletion of fadD in JC01(DE3) atoB$^{CT5}$fadBA$^{CT5}$ with pETDuet-fabI resulted in the extracellular production of 19.4±0.1 mg/L tetradecanoic acid (C14) and a slight increase in dodecanoic acid (C12), with minimal impact on the levels of C4-C10 carboxylic acids produced (FIG. 4A). In order to alter the product profile away from C4 and C6 carboxylic acids, yciA, encoding a thioesterase previously shown to have a marked effect on short chain product profiles (Clomburg 2012), was also deleted. This resulted in significant increases to C8 (97.4±1.9 mg/L) and C10 (102.5±8.0 mg/L) carboxylic acids while greatly reducing the amount of butyrate (0.47±0.01 g/L) (FIG. 4A). Surprisingly, the JC01 (DE3) atoB$^{CT5}$ fadBA$^{CT5}$ ΔfadD ΔyciA variant also resulted in a loss of the long-chain carboxylic acids, indicating that YciA may play a role as a longer chain acyl-CoA thioesterase as well as the shorter chains, while other thioesterases are potentially present to remain active on the medium chain acyl-CoAs (e.g. TesA, TesB, FadM).

Production of Odd Chain Carboxylic Acids

Figure 4B:
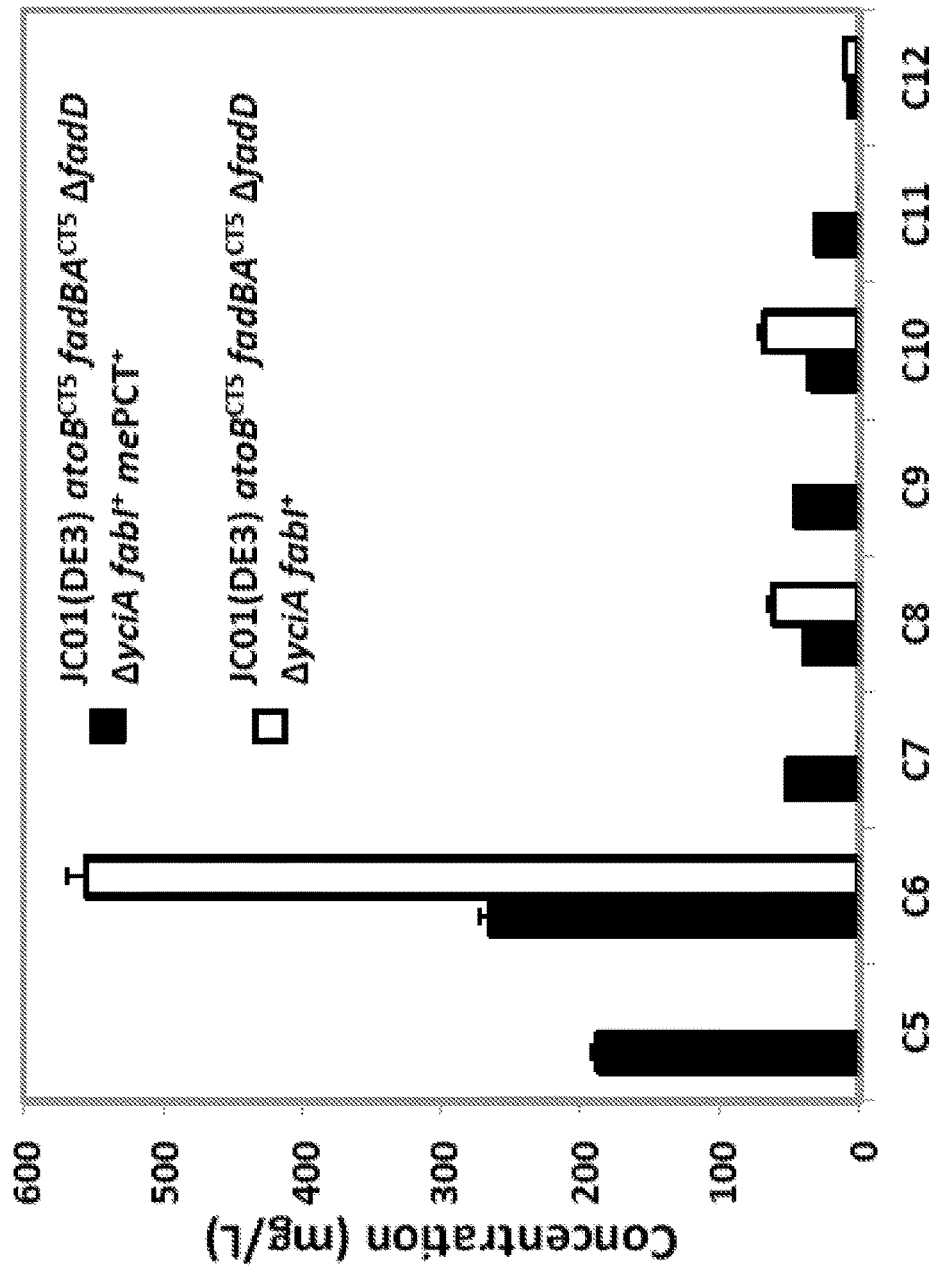

In order to investigate the potential for FabI to be used in the production odd-chain carboxylic acids, strain JC01 (DE3) atoB$^{CT5}$ fadBA$^{CT5}$ ΔfadD ΔyciA was further complemented with the propionate CoA transferase (PCT) from *M. elsdenii* (Taguchi et al., 2008), which has been used to successfully produce a variety of C5 fatty acid molecules (Tseng & Prather, 2012). mePCT was cloned into the pCDFDuet vector to facilitate co-expression with pETDuet-fabI. The two vectors were co-transformed into JC01 (DE3) atoB$^{CT5}$ fadBA$^{CT5}$ ΔfadD ΔyciA to determine odd chain carboxylic acid production in the presence of 15 mM propionate. This strain produced odd chain carboxylic acids ranging from 187±4 mg/L of valerate (C5) to a maximum chain length of C11 at 30.9±0.6 mg/L (FIG. 4B).

FABI Supports Product Synthesis

One concern when utilizing FabI as a trans-enoyl-CoA reductase is that product synthesis (e.g. butyrate and other products) could actually be proceeding through the type II FAS pathway, instead of the BOX-R. Fortunately, the condensation reactions responsible for carbon chain elongation in these two pathways are very different, providing an opportunity to clearly distinguish them. The BOX-R, which employ acetyl-CoA as the extender unit and a non-decarboxylating condensation mechanism (Binstock 1981, Jenkins 1987). The fatty acid biosynthesis pathway uses ketoacyl-ACP synthases, which employ a decarboxylating condensation mechanism and malonyl-ACP as the extender unit (White 2005).

Figure 5:
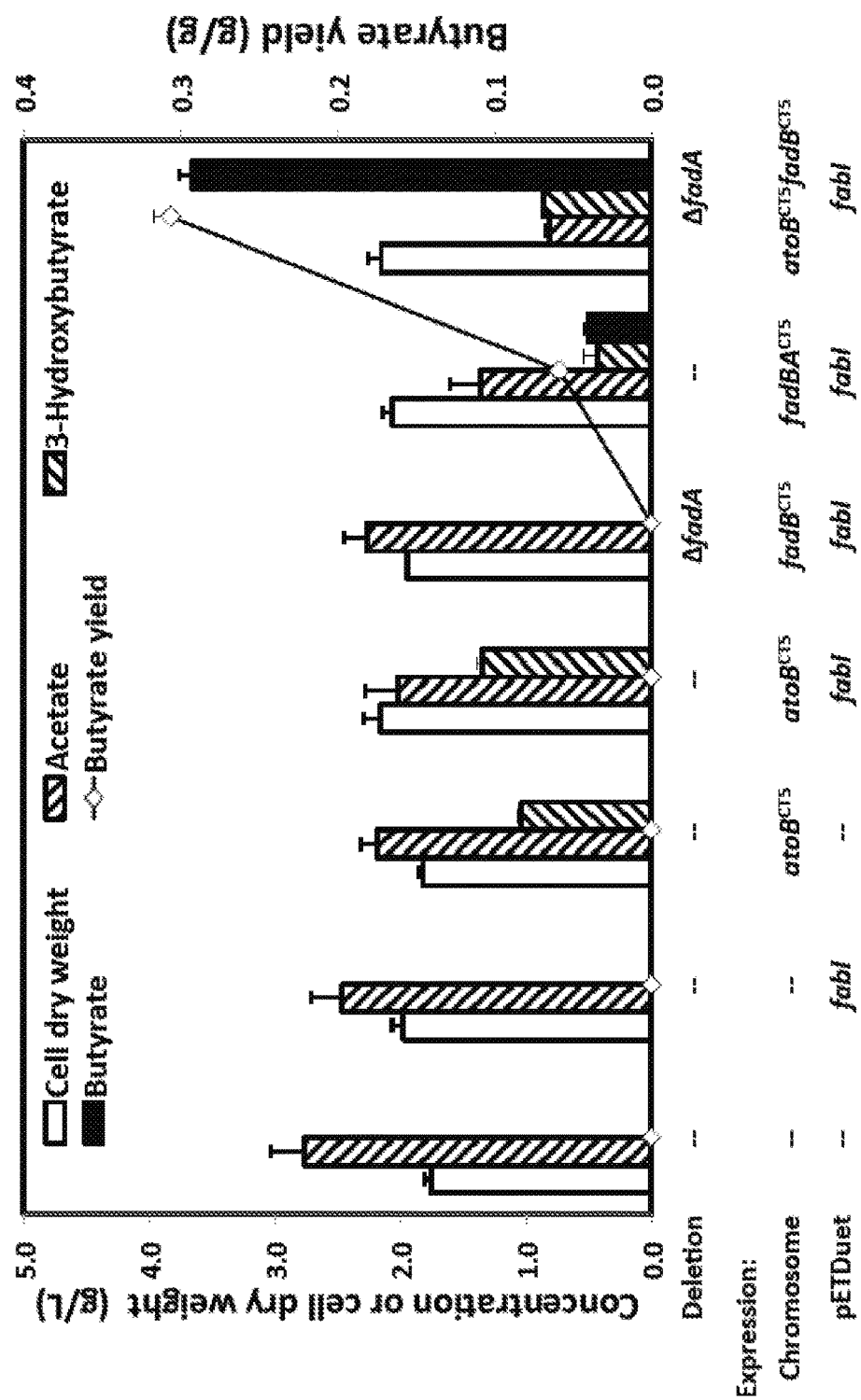
FIG. 5. Cell growth and product synthesis for strain JC01(DE3) and its derivatives demonstrating the FabI-mediated production of carboxylic acids proceeds through a functional reversal of the β-oxidation cycle. Modifications to JC01(DE3) are indicated by either a gene deletion (Δ"gene") or overexpression (chromosome or vector pET-Duet).

Overexpression of FabI in strain JC01(DE3) resulted predominantly in the production of acetate, a fermentation profile essentially undistinguishable from that of JC01(DE3) carrying the empty pETDuet vector (FIG. 5). In fact, butyrate production with FabI expression was only observed when a thiolase (AtoB or FadA) was used in conjunction with FadB (FIG. 5). The requirement of a non-decarboxylating condensation enzyme (e.g. thiolases AtoB or FadA), as well as the β-oxidation enzyme FadB (which only functions with CoA substrates) to observe the synthesis of butyrate indicates that FabI is facilitating a reversal of the β-oxidation cycle despite being an enzyme of the type II fatty acid biosynthesis pathway.

Other Enoyl-ACP Reductases

Figure 6:
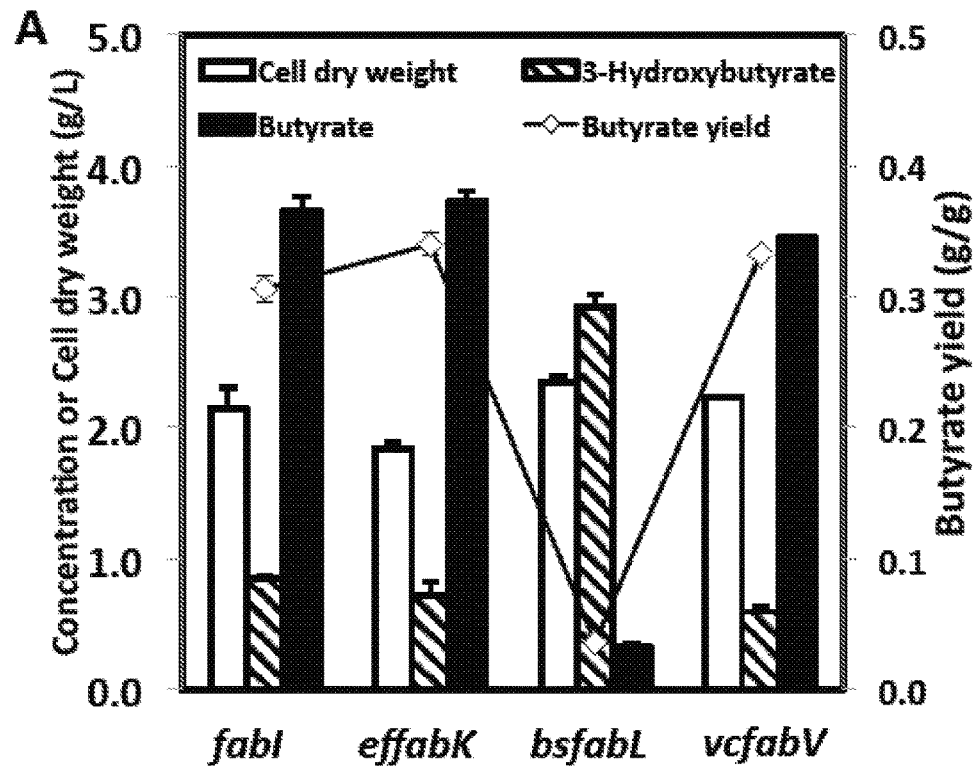
FIG. 6. Operation of a functional reversal of the BOX-R using different enoyl-ACP reductases from the type II fatty acid biosynthesis pathway.
Figure 6:
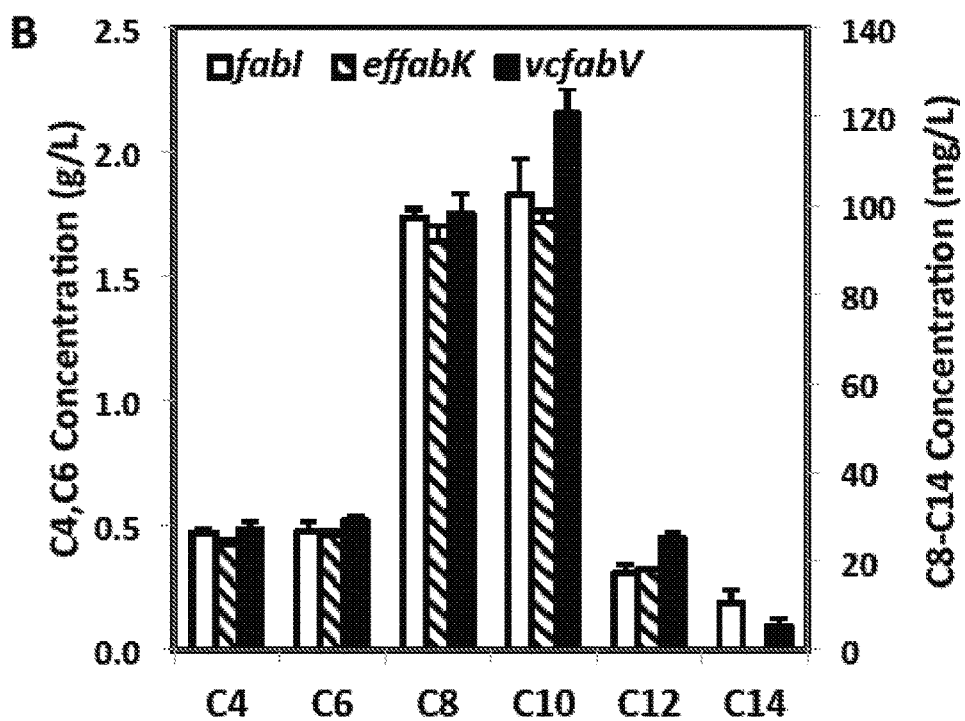

The identification of FabI as an enzyme that enables efficient operation of the β-oxidation reversal prompted us to investigate whether other ENRs from the type II fatty acid biosynthesis pathway can play a similar role. While bsFabL was found to complement a fabI deletion without promiscuous activity on CoA substrates, measurement of crotonyl-CoA reduction activity with strains expressing efabK and vcfabV indicated their potential to support a β-oxidation reversal (Table 1). When overexpressed in JC01(DE3) atoB$^{CT5}$ fadB$^{CT5}$ ΔfadA, both efFabK and vcFabV resulted in a marked increase in butyrate production, similar to that fabI overexpression (FIG. 6A). As expected based on the results from ΔfabI complementation and NAD(P)H-dependent crotonyl-CoA reduction measurements (Table 1), bsFabL had a profile quite similar to the empty pETDuet vector in that only small amounts of butyrate were produced (0.33±0.02 g/L) (FIG. 6A). Observed differences in butyrate production are not due to an altered growth phenotype as all the strains grew to similar densities. In addition to supporting butyrate production from a one-turn β-oxidation reversal, when pETDuet-efabK and pETDuet-vcfabV were overexpressed in JC01(DE3) atoB$^{CT5}$ fadBA$^{CT5}$ ΔfadD ΔyciA, longer chain carboxylic acids were produced at levels similar to that with pETDuet-fabI (FIG. 6B).

Other Type II Fatty Acid Synthesis Enzymes

In addition to the use of FabI or other enoyl-[acyl-carrier-protein] reductases from the type II fatty acid biosynthesis pathway, the 3-oxoacyl-[acyl-carrier-protein]/β-ketoacyl-[ACP] reductase (FabG, others) and 3-hydroxyacyl-[ACP] dehydratase (FabA, FabZ, others) enzymes of the type II FAS pathway can be utilized during BOX-R in place of BOX enzyme(s) (FadB). In order to establish the potential of these enzymes for product formation when expressed with non-decarboxylative thiolase(s), enoyl-[acyl-carrier-protein] reductases, and appropriate termination pathways, product formation was first investigated from a one-turn BOX-R with the overexpression of various combinations of FabG, FabZ, and FabI.

Figure 7:
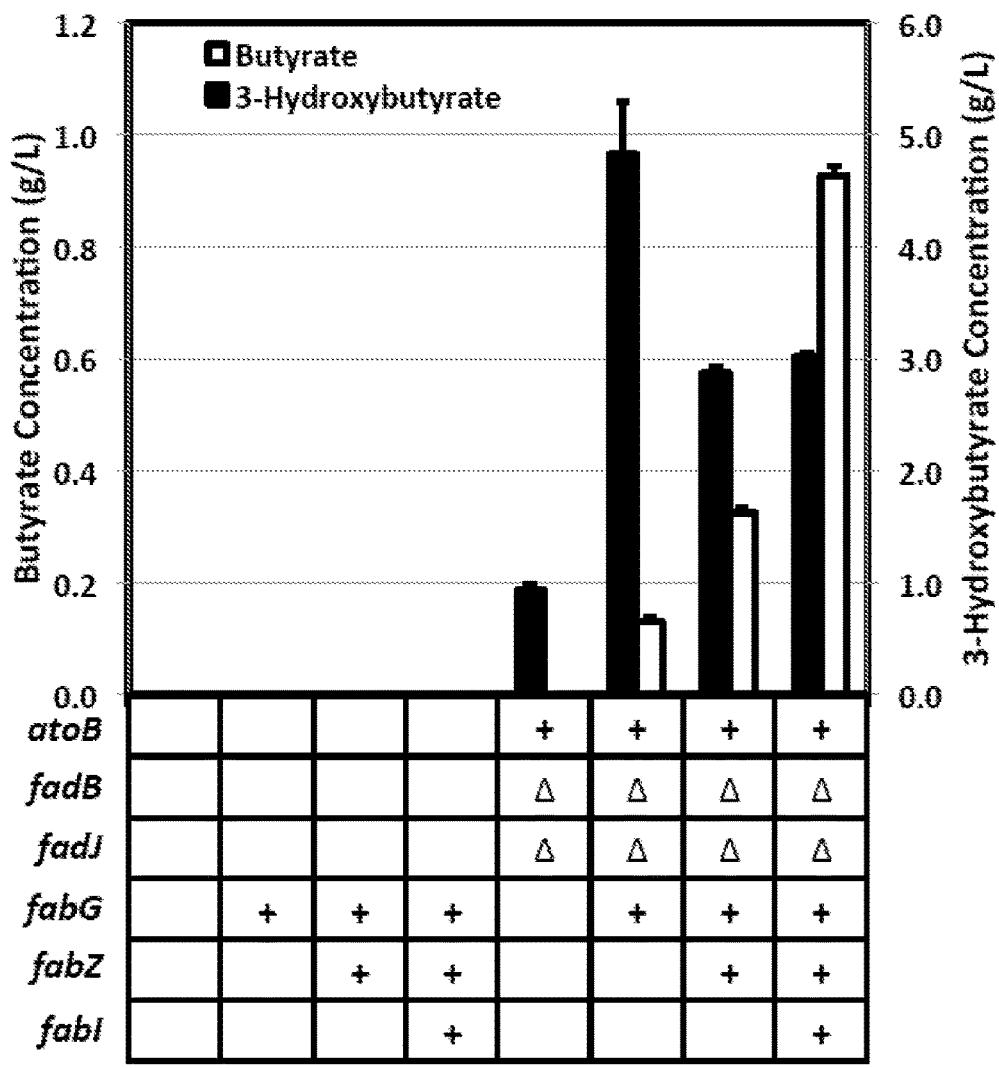
FIG. 7. BOX-R with the use of enzymes from the type II FAS pathway. Carboxylic acid products from a one-turn reversal are only observed with the overexpression of FAS enzymes (FabG, FabZ, FabI) in combination with thiolase (AtoB) overexpression. fadB and fadj is deleted in the case of thiolase expression to ensure product formation is not proceeding through β-oxidation enzymes. Data shown for strain JC01(DE3) with indicated overexpression (+) and deletions (Δ). fabG, fabZ, and fabI overexpressed from pETDuet vector while atoB expression through cumate controlled chromosomal construct at atoB locus.

For this purpose, pETDuet vectors containing FabG (pET-P1-P2-fabG), FabG and FabZ (pET-P1-P2-fabG-fabZ), and all of FabG, FabZ, and FabI (pET-P1-fabI-P2-fabG-fabZ) were utilized for the overexpression of these enzymes in both JC01(DE3) and a JC01(DE3) variant containing the cumate-controlled atoB expression construct. This latter strain also included deletions to fadB and fadJ to ensure any product formation was not a result of endogenous β-oxidation enzymes (JC01(DE3) atoB$^{CT5}$ ΔfadB ΔfadJ). As seen in FIG. 7, the overexpression of FabG, FabZ, and FabI only resulted in β-oxidation reversal product formation (i.e. 3-hydroxybutyrate and/or butyrate) when these enzyme(s) were overexpressed in combination with atoB. Furthermore, the concentration of butyrate, representing the final product of a full one-turn BOX-R with thioesterase termination, increases as FabG is overexpressed in combination with FabZ and further when all 3 FAS enzymes are overexpressed (FabG, FabZ, and FabI). These results provide strong evidence to the fact that a β-oxidation reversal is taking place through a non-decarboxylative condensation mechanism and CoA intermediates even with the use of enzymes from the type II fatty acid biosynthesis pathway.

Figure 8:
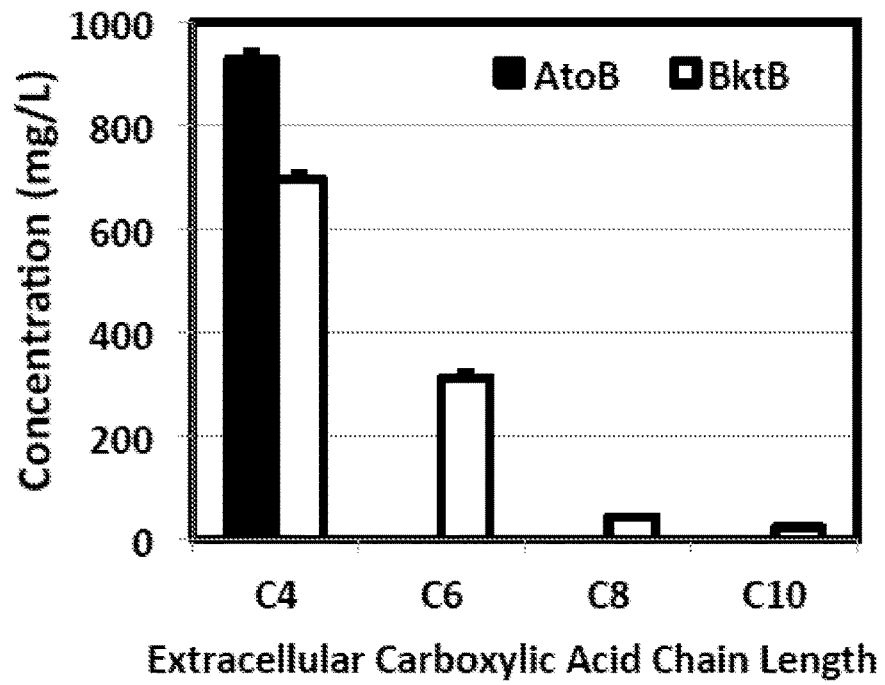
FIG. 8. Multiple cycle BOX-R with the use of enzymes from the type II FAS pathway for the production of longer acid carboxylic acids. The use of longer chain specific thiolase BktB from Ralstonia eutropha in place of AtoB enables the multiple cycle turns leading to carboxylic acid synthesis with endogenous thioesterase termination. Data shown for strain JC01(DE3) ΔfadB ΔfadJ (pET-P1-fabI-P2- fabG-fabZ) with either atoB or btkB overexpression under cumate control at the atoB chromosomal locus. The vectors (pET or pCDF) have 2 promotors that genes can be cloned behind. P1 and P2 indicate first or second promoter use.

The ability for BOX-R with the use of type II FAS pathway to support longer chain product synthesis was investigated through the replacement of AtoB with the longer chain specific thiolase BktB from *Ralstonia eutropha* (Kim 2014). With this thiolase was utilized with FabG, FabZ, and FabI expression in the JC01(DE3) derivative lacking key β-oxidation enzymes (JC01(DE3) btkB$^{CT5}$ ΔfadB ΔfadJ) the synthesis of extracellular longer chain carboxylic acids up to ten carbons in length was observed (FIG. 8), demonstrating the ability for FAS enzymes to support longer chain product formation when utilized with a non-decarboxylative thiolase of longer chain specificity.

Other Primary Termination Pathways

The establishment of the ability for three *E. coli* type II FAS pathway enzymes to support one- and multiple-turn BOX-R cycles when overexpressed with a non-decarboxylative thiolase utilized endogenous termination pathways for the direct conversion of pathway intermediates to carboxylic acids. However, further product diversification can be achieved through the use of additional primary termination pathways for the synthesis of varying product families from β-oxidation reversal intermediates.

To demonstrate this potential, the overexpression of a primary termination pathway for alcohol production was investigated in strains shown to produce one-turn and multiple-turn BOX-R products (i.e. JC01(DE3) atoB$^{CT5}$ ΔfadB ΔfadJ or JC01(DE3) btkB$^{CT5}$ ΔfadB ΔfadJ containing pET-P1-fabI-P2-fabG-fabZ). For this purpose, the combination of the *Clostridium beijerinckii* aldehyde-forming acyl-CoA reductase ALD (cbjALD) (Yan 1990) and *E. coli* alcohol dehydrogenase FucO (Dellomonaco 2011) were cloned into pCDFDuet to provide the ability to co-express all FAS enzymes along with this alcohol producing termination pathway.

As seen in FIG. 9, the overexpression of this termination pathway resulted in primary alcohol production whose chain length was also dependent on the thiolase utilized. With AtoB as the thiolase, the production of butanol was observed from a one-turn β-oxidation reversal, while the use of BktB enabled the synthesis of hexanol and octanol as well as butanol production. In addition to demonstrating the ability for the selection of the primary termination pathway to dictate product synthesis, the use of an aldehyde-forming acyl-CoA reductase provides further evidence to the operation of BOX-R with CoA intermediates even with the use of type II FAS enzymes, as this enzyme directly utilizes CoA substrates as opposed to ACP intermediates.

Production of Odd Chain Products

The ability for type II FAS enzymes to support odd-chain product synthesis through a BOX-R was investigated through the use of propionyl-CoA as the initial primer. This was accomplished through the overexpression of the propionate CoA transferase (PCT) from *M. elsdenii* (Taguchi et al., 2008) for the activation of propionate to propionyl-CoA. When this enzyme was overexpressed from a pCDF vector in strain JC01(DE3) btkB$^{CT5}$ ΔfadB ΔfadJ (pET-P1-fabI-P2-fabG-fabZ) in the presence of propionate, the synthesis of C5, C7, and C9 carboxylic acids was observed through endogenous termination pathways (FIG. 10). Furthermore, when propionate activation was combined with the overexpression of the alcohol-forming acyl-CoA reductase Maqu2507 from *Marinobacter aquaeolei* VT8 (Willis 2011) in JC01(DE3) btkB$^{CT5}$ ΔfadB ΔfadJ (pET-P1-fabI-P2-fabG-fabZ), the production of odd-chain primary alcohols was observed (FIG. 11).

Thus, in addition to demonstrating the ability for odd-chain product synthesis through a full BOX-R with enzymes from the type II FAS pathway, the production of alcohols with Maqu2507 represents the use of an additional primary termination pathway. As opposed to alcohol production with the combination of an aldehyde-forming acyl-CoA reductase and an alcohol dehydrogenase, the production of primary alcohols in this case makes use of a bi-functional enzyme for the 2-step reduction of an acyl-CoA to an alcohol.

Secondary Termination Pathways

Another route to additional product diversification is the use of secondary termination pathways to add additional functional groups to the above mentioned products of primary termination pathways (FIG. 1). An example of this is the use of a carboxylic acid omega hydroxylase to introduce omega functionality in the form of an alcohol group to carboxylic acids produced from a β-oxidation reversal with the use of type II fatty acid biosynthesis enzymes and primary termination pathways. While several potential enzymes can be utilized for this purpose, the alkane monooxygenase AlkBGT from *Pseudomonas putida* was been linked to the ability to omega hydroxylate carboxylic acids (Kusunose 1964; McKenna & Coon 1970) with more recent studies demonstrating the ability for AlkBGT to ω-hydroxylate medium chain length (C5-C12) fatty acid methyl esters (Julsing 2012; Schrewe 2011; Schrewe 2014).

In order to demonstrate the potential for the use of secondary termination to provide increased product functionality and diversity, the alkBGT genes from *P. putida* were cloned into pCDF to allow for co-expression with all other enzymes required to generate carboxylic acids from a BOX-R with type II FAS enzymes. When AlkBGT was overexpressed in strain JC01(DE3) btkB$^{CT5}$ ΔfadB ΔfadJ (pET-P1-fabI-P2-fabG-fabZ), the synthesis of 6-hydroxyhexanoic, 8-hydroxyoctanoic, and 10-hydrodecanoic acids was observed from the omega oxidation of carboxylic acids generated from primary termination pathways (FIG. 12). The production of these compounds demonstrates the potential of secondary termination pathways to generate a diverse set of products dependent on the combination of primary and secondary termination pathways used.

For example, the synthesis of dicarboxylic acids can be achieved through the further oxidation of omega-hydroxyacids, through the use of an alcohol and aldehyde dehydrogenase (Cheng 2000), while omega amino acids such as 6-aminocaproic acid can be synthesized from omega-hydroxyacids through the overexpression of an alcohol dehydrogenase and a transaminase (Schrewe 2013). These product classes represent just a small sample of the potential products that can be generated through a β-oxidation reversal with the use of type II fatty acid biosynthesis enzymes (FIG. 1). As such, the combinatorial selection of various primary and secondary termination pathways can be further exploited to synthesize a wide variety of industrially important fuel and chemical compounds.

Product Diversity Through Functionalized Primers

An additional route to generating further product diversity is the introduction of functional groups at the initial priming step of the BOX-R. For example, the use of a priming molecule such as succinyl-CoA or glycolyl-CoA for initial condensation with acetyl-CoA can introduce ω-carboxyl or ω-hydroxyl groups, respectively, with subsequent β-oxidation cycle turns and primary termination leading to various product classes (FIG. 1). This approach relies on the ability a thiolase to condense a given functionalized acyl-CoA molecule with acetyl-CoA as well as the enzymes involved in the cycle steps (reduction, dehydration, and reduction) to accept substrates with these functional groups.

Several thiolases have been identified with the potential to condense functionalized acyl-CoA molecules such as succinyl-CoA and glycolyl-CoA with acetyl-CoA, including *Ralstonia eutropha* bktB (Martin 2013), *E coli* paaJ (Ismail 2010), and *Pseudomonas putida* pcaF (Harwood 1994) among others. Genetic constructs for the overexpression of these enzymes have been assembled and are currently being investigated along with enzymes for the activation of potential acid primer molecules to their CoA derivatives (such as mePCT and *Clostridium kluyveri* Cat1) to determine their potential for this route to product synthesis (FIG. 13). These constructs will enable further investigation into the ability of type II FAS enzymes to accept substrates with varying functionalities in this context. In should be noted that type II FAS enzymes have been implicated in the biotin synthetic pathway in which FabG, FabZ, and FabI are involved in the reduction, dehydration, and reduction of various chain length omega methyl ester ACP intermediates (Lin 2010), which holds great potential for the utilization of these enzymes in a BOX-R with functionalized intermediates. This type of priming, combined with various primary and secondary termination pathways provides an additional route to potential expand the product diversity that can be achieved through the BOX-R and type II FAS pathways.

| | | Enzyme activity (μmol/mg protein/min)$^a$ | | |
|---|---|---|---|---|
| | | | NADH-Dependent Trans-enoyl-CoA reductase Crotonyl-CoA concentration$^b$ | |
| | | Acyl-CoA | | |
| Strain | Vector | dehydrogenase | 80 μM | 1 mM |
| JC01(DE3) atoB$^{CT5}$ fadB$^{CT5}$ ΔfadA | pETDuet (8 hours) | 0.0034 ± .0001 | n.d.$^c$ | 0.10 ± .001 |
| | pETDuet (48 hours) | 0.0020 ± .0002 | n.d.$^c$ | 0.080 ± .007 |
| JC01(DE3) atoB$^{CT5}$ fadB$^{CT5}$ ΔfadA ΔfadE | pETDuet | 0.0016 ± .00002 | — | — |
| JC01(DE3) atoB$^{CT5}$ fadB$^{CT5}$ ΔfadA ΔydiO | pETDuet | 0.0018 ± .0001 | — | — |
| JC01(DE3) atoB$^{CT5}$ fadB$^{CT5}$ ΔfadA Δcai4 | pETDuet | 0.0011 ± .0001 | — | — |
| JC01(DE3) atoB$^{CT5}$ fadB$^{CT5}$ ΔfadA ΔaidB | pETDuet | 0.0026 ± .00003 | — | — |
| JC01(DE3) atoB$^{CT5}$ fadB$^{CT5}$ ΔfadA | pETDuet-fadE | 0.019 ± .002 | — | — |
| | pETDuet-ydiO | 0.0031 ± .0003 | — | — |
| | pETDuet-caiA | 0.0014 ± .0002 | — | — |
| | pETDuet-egTER | — | 3.1 ± 0.4 | — |
| | pETDuet-fabI | — | 0.5 ± 0.05 | 3.4 ± .27 |
| | pETDuet-effabK | — | 0.05 ± .010 | 0.14 ± .01 |
| | pETDuet-bsfabL | — | n.d.$^c$ | 0.019 ± .006 |
| | pETDuet-vcfabV | — | 0.053 ± .010 | 4.3 ± 1.6 |
| JC01(DE3) atoB$^{CT5}$ fadB$^{CT5}$ ΔfadA ΔfabI | pETDuet-fabI | 0.0010 ± .0032 | 0.14 ± .006 | 1.8 ± .10 |
| | pETDuet-bsfabL | 0.0020 ± .0002 | n.d. | n.d. |

Each reference below is incorporated by reference its entirety for all purposes.

Atsumi, S., Cann, A. F., Connor, M. R., Shen, C. R., Smith, K. M., Brynildsen, M. P., . . . Liao, J. C. (2008). Metabolic engineering of *Escherichia coli* for 1-butanol production. *Metabolic engineering*, 10(6), 305-11.

Baba, T., Ara, T., Hasegawa, M., Takai, Y., Okumura, Y., Baba, M., . . . Mori, H. (2006). Construction of *Escherichia coli* K-12 in-frame, single-gene knockout mutants: the Keio collection. *Molecular systems biology*, 2, 2006.

Bergler, H., et al., (1994) Protein EnvM Is the NADH-dependent Enoyl-ACP Reductase (FabI) of *Escherichia coli*. *The Journal of biological chemistry*, 269(8), 5493-5496.

Bergler, H. et al., (1996) which catalyzes a key regulatory step in fatty acid biosynthesis, accepts NADH and NADPH as cofactors and is inhibited by palmitoyl-CoA, 694, 689-694.

Bi H. K., et al., (2014) Inefficient Translation Renders the *Enterococcus faecalis* fabK Enoyl-Acyl Carrier Protein Reductase Phenotypically Cryptic. J. Bacteriol. 196:170-179.

Binstock J. F. & Schulz H. (1981) Fatty acid oxidation complex from *Escherichia coli*. Methods Enzymol. 71 Pt C:403-411.

Bond-Watts, B. B., et al., (2011a) Enzyme mechanism as a kinetic control element for designing synthetic biofuel pathways. *Nature chemical biology*, 7(4), 222-7. doi:10.1038/nchembio.537

Bond-Watts, B. B., et al., (2011b) Enzyme mechanism as a kinetic control element for designing synthetic biofuel pathways. *Nature chemical biology*, 7(4), 222-7.

Campbell, J. W. & Jr, J. E. C. (2002) The Enigmatic *Escherichia coli* fadE Gene Is yafH, 184(13), 3759-3764.

Campbell, J. W., et al., (2003) A new *Escherichia coli* metabolic competency: growth on fatty acids by a novel anaerobic beta-oxidation pathway. *Molecular microbiology*, 47(3), 793-805.

Cheng, Q., T et al., (2000) Genetic analysis of a gene cluster for cyclohexanol oxidation in *Acinetobacter* sp strain SE19 by in vitro transposition. J. Bacteriol. 182, 4744-4751.

Choi, Y. J., et al., (2010) Novel, versatile, and tightly regulated expression system for *Escherichia coli* strains. *Applied and environmental microbiology*, 76(15), 5058-66.

Clomburg J. M., et al., (2012) A Synthetic Biology Approach to Engineer a Functional Reversal of the β-Oxidation Cycle. ACS Synth. Biol. 1:541-554.

Datsenko, K. A. & Wanner, B. L. (2000) One-step inactivation of chromosomal genes in *Escherichia coli* K-12 using PCR products. *Proceedings of the National Academy of Sciences of the United States of America*, 97(12), 6640-5.

Dellomonaco, C., et al., (2011) Engineered reversal of the β-oxidation cycle for the synthesis of fuels and chemicals. *Nature*, 476(7360), 355-359.

Elssner, T., et al., (2000) Isolation, identification, and synthesis of gamma-butyrobetainyl-CoA and crotonobetainyl-CoA, compounds involved in carnitine metabolism of *E. coli*. *Biochemistry*, 39(35), 10761-9.

Harwood C. S., et al., (1994) Identification of the pcaRKF gene cluster from *Pseudomonas putida*: involvement in chemotaxis, biodegradation, and transport of 4-hydroxybenzoate. J. Bacteriol. 176, 6479-6488.

Heath, R. J. & Rock, C. O. (1995) Enoyl-Acyl Carrier Protein Reductase (fabI) Plays a Determinant Role in Completing Cycles of Fatty Acid Elongation in *Escherichia coli*. *Journal of Biological Chemistry*, 270(44), 26538-26542.

Heath R. J., et al., (2000) The enoyl-acyl-carrier-protein reductases FabI and FabL from *Bacillus subtilis*. J. Biol. Chem. 275:40128-40133.

Ishihama, Y., et al., (2008) Protein abundance profiling of the *Escherichia coli* cytosol. *BMC genomics*, 9, 102.

Ismail W., et al., (2003) Functional genomics by NMR spectroscopy. Phenylacetate catabolism in *Escherichia coli*. Eur. J. Biochem. 270, 3047-3054.

Jenkins L. S. & Nunn W. D. (1987) Genetic and molecular characterization of the genes involved in short-chain fatty-acid degradation in *Escherichia coli*: The ato system. J. Bacteriol. 169:42-52.

Julsing, M. K., et al., (2012) Outer Membrane Protein AlkL Boosts Biocatalytic Oxyfunctionalization of Hydrophobic Substrates in *Escherichia coli*. Appl. Environ. Microbiol. 78, 5724-5733.

Kang, Y., et al., (2004) Systematic mutagenesis of the *Escherichia coli* genome. *Journal of bacteriology*, 186, 4921-4930.

Kim, E. J., et al., (2014) Crystal structure and biochemical characterization of β-keto thiolase B from polyhydroxyalkanoate-producing bacterium *Ralstonia eutropha* H16. Biochem. Biophys. Res. Commun 444, 365-369.

Kitagawa, M., et al., (2005) Complete set of ORF clones of *Escherichia coli* ASKA library (a complete set of *E. coli* K-12 ORF archive): unique resources for biological research. *DNA research: an international journal for rapid publication of reports on genes and genomes*, 12(5), 291-9.

Kusunose, M., et al., (1964) Enzymatic ω-Oxidation of Fatty Acids: I. Products of Octanoate, Decanoate, and Laurate Oxidation. J. Biol. Chem. 239, 1374-1380.

Landini, P., et al., (1994) Structure and transcriptional regulation of the *Escherichia coli* adaptive response gene aidB. *J. Bacteriol.*, 176(21), 6583-9.

Lennen R. M. & Pfleger B, F. (2012) Engineering *Escherichia coli* to synthesize free fatty acids. Trends Biotechnol. 30:659-667.

Lin S., et al., (2010) Biotin synthesis begins by hijacking the fatty acid synthetic pathway. Nat. Chem. Biol. 6, 682-688.

Magner, D. B., et al., (2007) RecQ promotes toxic recombination in cells lacking recombination intermediate-removal proteins. *Molecular cell*, 26(2), 273-86.

Martin C. H., et al., (2013) A platform pathway for production of 3-hydroxyacids provides a biosynthetic route to 3-hydroxy-γ-butyrolactone. Nat. Commun 4, 1414.

Massengo-Tiasse R. P. & Cronan J. E. (2008) *Vibrio cholerae* FabV defines a new class of enoyl-acyl carrier protein reductase. J. Biol. Chem. 283:1308-1316.

Miller, J. H. (1972) *Experiments in Molecular Genetics*. Cold Spring Harbor, New York: Cold Spring Harbor Laboratory Press.

McKenna, E. J. & Coon, M. J. (1970) Enzymatic ω-Oxidation: IV. Purification and Properties of the ω-Hydroxylase of *Pseudomonas oleovorans*. J. Biol. Chem. 245, 3882-3889.

O'Brien, W. J. & Frerman, F. E. (1977) Evidence for a complex of three beta-oxidation enzymes in *Escherichia coli*: induction and localization. *Journal of bacteriology*, 132(2), 532-40.

Preusser, A., et al., (1999) Crotonobetaine reductase from *Escherichia coli* consists of two proteins. *Biochimica et biophysica acta*, 1431(1), 166-78.

Rohankhedkar, M. S., et al., (2006) The AidB Component of the *Escherichia coli* Adaptive Response to Alkylating Agents Is a Flavin-Containing, DNA-Binding Protein, 188 (1), 223-230.

Shams Yazdani, S. & Gonzalez, R. (2008) Engineering *Escherichia coli* for the efficient conversion of glycerol to ethanol and co-products. *Metabolic engineering*, 10(6), 340-51.

Shen, C. R., et al., (2011) Driving forces enable high-titer anaerobic 1-butanol synthesis in *Escherichia coli*. *Applied and environmental microbiology*, 77(9), 2905-15.

Schrewe, M., et al., (2011) Kinetic Analysis of Terminal and Unactivated C—H Bond Oxyfunctionalization in Fatty Acid Methyl Esters by Monooxygenase-Based Whole-Cell Biocatalysis. Adv. Synth. Catal. 353, 3485-3495.

Schrewe M., at al., (2013) Direct Terminal Alkylamino-Functionalization via Multistep Biocatalysis in One Recombinant Whole-Cell Catalyst. Adv. Synth. Catal. 355, 1693-1697.

Schrewe, M., et al., (2014) Reaction and Catalyst Engineering to Exploit Kinetically Controlled Whole-Cell Multistep Biocatalysis for Terminal FAME Oxyfunctionalization. Biotechnol. Bioeng. 111, 1820-1830.

Taguchi, S., et al., (2008) A microbial factory for lactate-based polyesters using a lactate-polymerizing enzyme. *PNAS(USA)*, 105(45), 17323-7.

Thomason, L., et al., (2007) Recombineering: genetic engineering in bacteria using homologous recombination. *Current protocols in molecular biology*/edited by Frederick M. Ausubel . . . [et al.], Chapter 1, Unit 1.16.

Tseng, H.-C., & Prather, K. L. J. (2012). Controlled biosynthesis of odd-chain fuels and chemicals via engineered modular metabolic pathways. *Proceedings of the National Academy of Sciences of the United States of America,* 109(44), 17925-30. doi:10.1073/pnas.1209002109

Tucci, S. & Martin, W. (2007) A novel prokaryotic trans-2-enoyl-CoA reductase from the spirochete *Treponema denticola. FEBS letters,* 581(8), 1561-6.

Vick, J. E., et al., (2011) Optimized compatible set of BioBrick™ vectors for metabolic pathway engineering. *Applied microbiology and biotechnology,* 1275-1286.

Weeks, G. & Wakil, S. J. (1968) GENERAL PROPERTIES OF THE REDUCTASES FROM *ESCHERICHIA* on the Mechanism of Fatty Acid.

Willis R. M., et al., (2011) Characterization of a Fatty Acyl-CoA Reductase from *Marinobacter aquaeolei* VT8: A Bacterial Enzyme Catalyzing the Reduction of Fatty Acyl-CoA to Fatty Alcohol. Biochemistry 50:10550-8.

White S. W., et al., (2005) The structural biology of type II fatty acid biosynthesis, p. 791-831, Annual Review of Biochemistry, vol. 74. Annual Reviews, Palo Alto.

Wiesenborn, D. P., et al., (1988) Thiolase from *Clostridium acetobutylicum* ATCC 824 and Its Role in the Synthesis of Acids and Solvents. *App. Environ. Microbiol.,* 54(11), 2717-22.

Yan R. T. & Chen J. S. (1990 (Coenzyme A-acylating aldehyde dehydrogenase from *Clostridium beijerinckii* NRRL B592. Appl. Environ. Microbiol. 56, 2591-2599.

Zhu L., et al. (2013) The Two Functional Enoyl-Acyl Carrier Protein Reductases of *Enterococcus faecalis* Do Not Mediate Triclosan Resistance. MBio 4:10.

The invention claimed is:

1. A genetically engineered microorganism, said microorganism having a reverse beta oxidation (BOX-R) cycle that grows a primer by adding a 2-carbon donor thereto in each cycle, said BOX-R cycle comprising:
   a) an overexpressed thiolase that catalyzes the non-decarboxylative condensation of an acyl-CoA primer with a 2-carbon donor acetyl-CoA to produce a β-ketoacyl-CoA;
   b) an overexpressed 3-oxoacyl-[acyl-carrier-protein] reductase or overexpressed 3-hydroxyacyl-CoA dehydrogenase that catalyzes the reduction of a β-ketoacyl-CoA to a β-hydroxyacyl-CoA;
   c) an overexpressed 3-hydroxyacyl-[acyl-carrier-protein] dehydratase or an overexpressed enoyl-CoA hydratase or 3-hydroxyacyl-CoA dehydratase that catalyzes the dehydration of a (3R)-β-hydroxyacyl-CoA to a transenoyl-CoA;
   d) an overexpressed enoyl-[acyl-carrier-protein] reductase or acyl-CoA dehydrogenase or trans-enoyl-CoA reductase that catalyzes the reduction of a transenoyl-CoA to an acyl-CoA that is two carbons longer than said acyl coA primer;
      i) wherein at least one of the enzymes from steps b-d is a fatty acid synthesis enzyme; and
   e) an overexpressed termination pathway that catalyzes the exit of an intermediate from said BOX-R cycle.

2. The microorganism of claim 1, wherein said termination pathway is selected from the group consisting of i) a thioesterase, ii) an acyl-CoA:acetyl-CoA transferase, and iii) a phosphotransacylase and a carboxylate kinase, and wherein said microorganism produces a product selected from the group consisting of carboxylic acids, (3R)-β-hydroxy carboxylic acids, β-keto carboxylic acids, and α,β-unsaturated carboxylic acids.

3. The microorganism of claim 1, wherein said termination pathway is selected from the group consisting of i) an alcohol-forming coenzyme-A thioester reductase, and ii) an aldehyde-forming CoA thioester reductase and an alcohol dehydrogenase, and wherein said microorganism produces a product selected from the group consisting of primary alcohols, 1,(3R)-β diols, β-keto primary alcohols, and α,β-unsaturated primary alcohols.

4. The microorganism of claim 1, wherein said termination pathway consists of an aldehyde-forming CoA thioester reductase and an aldehyde decarbonylase, and wherein said microorganism produces a product selected from the group consisting of linear alkanes, linear alkan-3-ols, linear methyl-ketones, and 1-alkenes.

5. The microorganism of claim 1, wherein said termination pathway consists of an aldehyde-forming CoA thioester reductase and a transaminase, and wherein said microorganism produces a product selected from the group consisting of primary amines, 3-hydroxy-amines, 3-keto-amines, and α,β-unsaturated primary amines.

6. The microorganism of claim 2, wherein said microorganism expresses a carboxylic acid omega hydroxylase and produces a product selected from the group consisting of ω-hydroxylated carboxylic acids, (3R)-β-, ω-dihydroxy carboxylic acids, β-keto, ω-hydroxy carboxylic acids, and α,β-unsaturated ω-hydroxylated carboxylic acids.

7. The microorganism of claim 3, wherein said microorganism expresses a carboxylic acid ω hydroxylase, an alcohol oxidase, and an aldehyde dehydrogenase, and produces a product selected from the group consisting of ω-hydroxylated carboxylic acids, (3R)-β-, ω-dihydroxy carboxylic acids, β-keto, ω-hydroxy carboxylic acids, and α,β-unsaturated omega-hydroxylated carboxylic acids.

8. The microorganism of claim 3, wherein said microorganism expresses a carboxylic acid ω hydroxylase, and produces a product selected from the group consisting of 1-,ω-diols, 1-,(3R)-β-, ω-triols, β-keto, 1-,ω-diols, and α,β-unsaturated 1-,ω-diols.

9. The microorganism of claim 2, wherein said microorganism expresses a carboxylic acid ω hydroxylase, an alcohol oxidase, and an aldehyde dehydrogenase, and produces a product selected from the group consisting of di-carboxylic acids, (3R)-β-hydroxy di-carboxylic acids, β-keto di-carboxylic acids, and α,β-unsaturated di-carboxylic acids.

10. The microorganism of claim 3, wherein said microorganism expresses a carboxylic acid ω hydroxylase, an alcohol oxidase, and a transaminase, and produces a product selected from the group consisting of primary alkanolamines (i.e. 1, ω-hydroxyamines), (3R)-β-hydroxy primary alkanolamines, β-keto primary alkanolamines, and α,β-unsaturated primary alkanolamines.

11. The microorganism of claim 5, wherein said microorganism expresses a carboxylic acid ω hydroxylase, and produces a product selected from the group consisting of primary alkanolamines (i.e. 1, ω-hydroxyamines), (3R)-β-hydroxy primary alkanolamines, β-keto primary alkanolamines, and α,β-unsaturated primary alkanolamines.

12. The microorganism of claim 5, wherein said microorganism expresses a carboxylic acid ω hydroxylase, an alcohol oxidase, and an aldehyde dehydrogenase, and produces a product selected from the group consisting of ω-amino acids, (3R)-β-hydroxy ω-amino acids, β-keto ω-amino acids, and α,β-unsaturated ω-amino acids.

13. The microorganism of claim 2, wherein said microorganism expresses a carboxylic acid alpha hydroxylase, and produces a product selected from the group alpha-hydroxy carboxylic acids, alpha-, (3R)-β-dihydroxy carboxylic acids, α-hydroxy, β-keto carboxylic acids, and α,β-unsaturated α-hydroxy carboxylic acids.

14. The microorganism of claim 3, wherein said microorganism expresses a carboxylic acid α hydroxylase, and produces a product selected from the group consisting of 1,2-diols, 1,2,3-triols, β-keto, 1,2-diols, and α,β-unsaturated 1,2-diols.

15. The microorganism of claim 5, wherein said microorganism expresses a carboxylic acid α hydroxylase, and produces a product selected from the group consisting of α-hydroxylated primary amines, α-, β- dihydroxy primary amines, α-hydroxy, β-keto primary amines, and α-hydroxy, α,β-unsaturated primary amines.

16. The microorganisms of claim 1, further comprising reduced expression of fermentation enzymes leading to reduced production of lactate, acetate, ethanol and succinate.

17. The microorganism of claim 1, wherein said overexpressed thiolase is encoded by E. coli atoB (NP_416728.1), E. coli yqeF (NP_417321.2), E. coli fadA (YP_026272.1), E. coli fadI (NP_416844.1), Ralstonia eutropha bktB (AAC38322.1), Pseudomonas sp. Strain B13 catF (AAL02407.1), E coli paaJ (NP_415915.1), Pseudomonas putida pcaF (AAA85138.1), Rhodococcus opacus pcaF (YP_002778248.1), Streptomyces sp. pcaF (AAD22035.1), Ralstonia eutropha phaA (AEI80291.1), Clostridium acetobutylicum thlA (AAC26023.1), and Clostridium acetobutylicum thlB (AAC26026.1).

18. The microorganism of claim 1, wherein said overexpressed 3-oxoacyl-[acyl-carrier-protein] reductase is encoded by E. coli fabG (NP_415611.1).

19. The microorganism of claim 1, wherein said overexpressed 3-hydroxyacyl-[ acyl-carrier-protein] dehydratase is encoded by a gene selected from the group consisting of E. coli fabA (NP_415474.1), and E. coli fabZ (NP_414722.1).

20. The microorganism of claim 1, wherein said enoyl-[acyl-carrier-protein] reductase is encoded by a gene selected from the group consisting of E. coli fabI (NP_415804.1), Enterococcus faecalis fabK (NP_816503.1), Bacillus subtilis fabL (KFK80655.1), and Vibrio cholerae fabV (ABX38717.1).

21. The microorganism of claim 2, wherein said overexpressed thioesterase is encoded by a gene selected from the group consisting of E. coli tesA (NP_415027.1), E. coli tesB (NP_414986.1), E. coli yciA (NP_415769.1), E. coli fadM (NP_414977.1), E. coli ydil (NP_416201.1), E. coli ybgC (NP_415264.1), Alcanivorax borkumensis tesB2 (YP_692749.1) Fibrobacter succinogenes Fs2108 (YP_005822012.1), Prevotella ruminicola Pr655 (YP_003574018.1) and Prevotella ruminicola Pr1687 (YP_003574982.1).

22. The microorganism of claim 2, wherein said overexpressed acyl-CoA:acetyl-CoA transferase is encoded by a gene selected from the group consisting of E. coli atoD (NP_416725.1), Clostridium kluyveri cat2 (AAA92344.1), Clostridium acetobutylicum ctfAB (NP_149326.1, NP_149327.1) and E. coli ydiF (NP_416209.1).

23. The microorganism of claim 2, wherein said overexpressed phosphotransacylase is encoded by a gene selected from the group consisting of Clostridium acetobutylicum ptb (NP_349676.1), Enterococcus faecalis ptb (AAD55374.1), and Salmonella enterica pduL (AAD39011.1).

24. The microorganism of claim 2, wherein said overexpressed carboxylate kinase is encoded by a gene selected from the group consisting of Clostridium acetobutylicum buk (AAK81015.1), Enterococcus faecalis buk (AAD55375.1), and Salmonella enterica pduW (AAD39021.1).

25. The microorganism of claim 3, wherein said overexpressed alcohol-forming coenzyme-A thioester reductase is encoded by a gene selected from the group consisting of Clostridium acetobutylicum adhE2 (YP_009076789.1), Arabidopsis thaliana At3g11980 (AEE75132.1), Arabidopsis thaliana At3g44560 (AEE77915.1), Arabidopsis thaliana At3g56700 (AEE79553.1), Arabidopsis thaliana At5g22500 (AED93034.1), Arabidopsis thaliana CER4 (AEE86278.1), Marinobacter aquaeolei VT8 maqu_2220 (YP_959486.1), and Marinobacter aquaeolei VT8 maqu_2507 (YP_959769.1).

26. The microorganism of claim 3, wherein said overexpressed aldehyde-forming CoA thioester reductase is encoded by a gene selected from the group consisting of Acinetobacter calcoaceticus acr1 (AAC45217.1), Acinetobacter sp Strain M-1 acrM (BAB85476.1), Clostridium beijerinckii ald (AAT66436.1), E. coli eutE (NP_416950.1), Salmonella enterica eutE (AAA80209.1), and E. coli mhpF (NP_414885.1).

27. The microorganism of claim 3, wherein said overexpressed alcohol dehydrogenase is encoded by a gene selected from the group consisting of E. coli betA (NP_414845.1), E. coli dkgA (NP_417485.4), E. coli eutG (NP_416948.4), E. coli fucO (NP_417279.2), E. coli ucpA (NP_416921.4), E. coli yahK (NP_414859.1), E. coli ybbO (NP_415026.1), E. coli ybdH (NP_415132.1), E. coli yiaY (YP_026233.1), and E. coli yjgB (NP_418690.4).

28. The microorganism of claim 4, wherein said aldehyde decarbonylase overexpressed is encoded by a gene selected from the group consisting of Synechococcus elongatus PCC7942 orf1593 (Q54764.1), Nostoc punctiforme PCC73102 npun_R1711 (B2J1M1.1), and Prochlorococcus marinus MIT9313 pmt1231 (Q7V6D4.1).

29. The microorganism of claim 5, wherein said overexpressed transaminase is encoded by a gene selected from the group consisting of Arabidopsis thaliana At3g22200 (NP_001189947.1), Alcaligenes denitrificans AptA (AAP92672.1), Bordetella bronchiseptica BB0869 (WP_015041039.1), Bordetella parapertussis BPP0784 (WP_010927683.1), Brucella melitensis BAWG_0478 (EEW88370.1), Burkholderia pseudomallei BP1026B_10669 (AFI65333.1), Chromobacterium violaceum CV2025 (AAQ59697.1), Oceanicola granulosus OG2516_07293 (WP_007254984.1), Paracoccus denitrificans PD1222 Pden_3984 (ABL72050.1), Pseudogulbenkiania ferrooxidans ω-TA (WP_008952788.1), Pseudomonas putida ω-TA (P28269.1), Ralstonia solanacearum ω-TA (YP_002258353.1), Rhizobium meliloti SMc01534 (NP_386510.1), and Vibrio fluvialis ω-TA (AEA39183.1), Mus musculus abaT (AAH58521.1) and E. coli gabT (YP_490877.1).

30. The microorganism of claims 7, wherein said overexpressed carboxylic acid omega hydroxylase is encoded by a gene selected from the group consisting of Pseudomonas putida alkBGT (YP_009076004.1, Q9WWW4.1, Q9L4M8.1),Marinobacter aquaeolei CYP 153A (ABM17701.1),Mycobacterium marinum CYP 153A16 (YP_001851443.1), Polaromonas sp. CYP 153A (YP_548418.1), Nicotiana tabacum CYP94A5 (AAL54887.1), Vicia sativa CYP94A1 (AAD10204.1), Vicia sativa CYP94A2 (AAG33645.1), Arabidopsis thaliana CYP94B1 (BAB08810.1), Arabidopsis CYP86A8 (CAC67445.1), Candida tropicalis CYP52A1 (AAA63568.1, AAA34354.1, AAA34334.1), Candida

*tropicalis* CYP52A2 (AAA34353.2, CAA35593.1), and *Homo sapiens* CYP4All (AAQ56847.1).

31. The microorganism of claim 7, wherein said overexpressed alcohol oxidase is encoded by a gene selected from the group consisting of *Rhodococcus ruber* SC1 cddC (AAL14237.1), *Acinetobacter* sp. SE19 chnD (AAG10028.1), *E. coli* yahK (NP_414859.1), and *E. coli* yjgB (NP_418690.4).

32. The microorganism of claim 7, wherein said overexpressed aldehyde dehydrogenase is encoded by a gene selected from the group consisting of *Rhodococcus ruber* SC1 cddD (AAL14238.1), and *Acinetobacter* sp. SE19 chnE (AAG10022.1).

33. The microorganism of claim 13, wherein said overexpressed fatty acid alpha hydroxylases is encoded by a gene selected from the group consisting of *Myxococcus xanthus* MXAN_0191 (YP_628473.1), and *Stigmatella aurantiaca* STIAU_3334 (YP_003957653.1).

34. The microorganism of claim 1, wherein said overexpressed thiolase is able to condense an omega-hydroxylated primer, an omega-carboxylated primer or a omega-aminated primer with acetyl-CoA and is encoded by a gene selected from the group consisting of *E. coli* atoB (NP_416728.1), *E. coli* yqeF (NP_417321.2), *E. coli* fadA (YP_026272.1), *E. coli* FadI (NP_416844.1), *Ralstonia eutropha* bktB (AAC38322.1), *Pseudomonas* sp. Strain B13 catF (AAL02407.1), *E coli* paaJ (NP_415915.1), *Pseudomonas putida* pcaF (AAA85138.1), *Rhodococcus opacus* pcaF (YP_002778248.1), *Streptomyces* sp. pcaF (AAD22035.1), *Ralstonia eutropha* phaA (AEI80291.1), *Clostridium acetobutylicum* thlA (AAC26023.1), and *Clostridium acetobutylicum* thlB (AAC26026.1).

35. The microorganism of claim 34, wherein said overexpressed 3-oxoacyl-[acyl-carrier-protein] reductase, overexpressed 3-hydroxyacyl-[acyl-carrier-protein] dehydratase, and overexpressed enoyl-[acyl-carrier-protein] reductase are able to act on omega-hydroxylated, omega-carboxylated or omega-aminated substrates and encoded by genes selected from the group consisting of *E. coli* fabA, *E. coli* fabG, *E. coli* fabI, *Enterococcus faecalis* fabK, *Bacillus subtilis* fabL, *Vibrio cholerae* fabV and *E. coli* fabZ.

36. The microorganism of claim 35, wherein said overexpressed termination pathways are able to act on omega-hydroxylated, omega-carboxylated or omega-aminated substrates and encoded by genes selected from the group consisting of *E. coli* tesA, *E. coli* tesB, *E. coli* yciA, *E. coli* fadM, *E. coli* ydiI, *E. coli* ybgC, *E. coli* paaI, *E. coli* ybdB, *A. Borkumensis* tesB, *A. thaliana* ACH2, *M. musculus* acot8, *S. cerevisiae* PTE1, *E. coli* atoD, *Clostridium kluyveri* cat2, *Clostridium acetobutylicum* ctfB, *E. coli* ydiF, *Clostridium acetobutylicum* ptb/buk, *Enterococcus faecalis* ptb/buk, *Salmonella enterica* pduL/pduW, *Clostridium acetobutylicum* adhE2, *Arabidopsis thaliana* At3g11980, *Arabidopsis thaliana* At3g44560, *Arabidopsis thaliana* At3g56700, *Arabidopsis thaliana* At5g22500, *Arabidopsis thaliana* CER4, *Marinobacter aquaeolei* VT8 maqu2507, *Acinetobacter calcoaceticus* acr 1, *Acinetobacter* sp Strain M-1 acrM, *Clostridium beijerinckii* ald, *E. coli* eutE, *Salmonella enterica* eutE, *E. coli* mhpF, *E. coli* betA, *E. coli* eutG, *E. coli* fucO, *E. coli* ucpA, *E. coli* ybbO, *E. coli* ybdH, *E, coli* yiaH, *Synechococcus elongatus* PCC7942 orf1593, *Nostoc punctiforme* PCC73102 npun_R1711, *Prochlorococcus marinus* MIT9313 pmt1231, *Mus musculus* abaT and *E. coli* gabT.

37. The microorganism of claim 1, wherein said overexpressed thiolase is able to condense an omega-carboxylated primer (e.g. oxalyl-CoA, malonyl-CoA, succinyl-CoA) with acetyl-CoA and encoded by a gene selected from the group consisting of *E. coli* atoB (NP_416728.1), *E. coli* yqeF (NP_417321.2), *E. coli* fadA (YP_026272.1), *E. coli* FadI (NP_416844.1), *Ralstonia eutropha* bktB (AAC38322.1), *Pseudomonas* sp. Strain B13 catF (AAL02407.1), *E coli* paaj (NP_415915.1), *Pseudomonas putida* pcaF (AAA85138.1), *Rhodococcus opacus* pcaF (YP_002778248.1), *Streptomyces* sp. pcaF (AAD22035.1), *Ralstonia eutropha* phaA (AEI80291.1), *Clostridium acetobutylicum* thlA (AAC26023.1), and *Clostridium acetobutylicum* thlB (AAC26026.1).

38. The microorganism of claim 37, wherein said overexpressed 3-oxoacyl-[acyl-carrier-protein] reductase, overexpressed 3-hydroxyacyl-[acyl-carrier-protein] dehydratase, and overexpressed enoyl-[acyl-carrier-protein] reductase are able to act on omega-carboxylated substrates and encoded by genes selected from the group consisting of *E. coli* fabA, *E. coli* fabG, *E. coli* fabI, *Enterococcus faecalis* fabK, *Bacillus subtilis* fabL, *Vibrio cholerae* fabV and *E. coli* fabZ.

39. The microorganism of claim 38, wherein said overexpressed termination pathways are able to act on omega-carboxylated substrates and encoded by genes selected from the group consisting of *E. coli* tesA, *E. coli* tesB, *E. coli* yciA, *E. coli* fadM, *E. coli* ydiI, *E. coli* ybgC, *E. coli* paaI, *E. coli* ybdB, *A. Borkumensis* tesB, *A. thaliana* ACH2, *M. musculus* acot8, *S. cerevisiae* PTE1, *E. coli* atoD, *Clostridium kluyveri* cat2, *Clostridium acetobutylicum* ctfB, *E. coli* ydiF, *Clostridium acetobutylicum* ptb/buk, *Enterococcus faecalis* ptb/buk, *Salmonella enterica* pduL/pduW, *Clostridium acetobutylicum* adhE2, *Arabidopsis thaliana* At3g11980, *Arabidopsis thaliana* At3g44560, *Arabidopsis thaliana* At3g56700, *Arabidopsis thaliana* At5g22500, *Arabidopsis thaliana* CER4, *Marinobacter aquaeolei* VT8 maqu2507, *Acinetobacter calcoaceticus* acr 1, *Acinetobacter* sp Strain M-1 acrM, *Clostridium beijerinckii* ald, *E. coli* eutE, *Salmonella enterica* eutE, *E. coli* mhpF, *E. coli* betA, *E. coli* eutG, *E. coli* fucO, *E. coli* ucpA, *E. coli* ybbO, *E. coli* ybdH, *E, coli* yiaH, *Synechococcus elongatus* PCC7942 orf1593, *Nostoc punctiforme* PCC73102 npun_R1711, *Prochlorococcus marinus* MIT9313 pmt1231, *Mus musculus* abaT and *E. coli* gabT.

40. The microorganism of claim 1, wherein said overexpressed thiolase is able to condense an omega-aminated primer (e.g. 2-amino-acetyl-CoA, 3-amino-propionyl-CoA, 4-amino-butyryl-CoA) with acetyl-CoA and encoded by a gene selected from the group consisting of *E. coli* atoB (NP_416728.1), *E. coli* yqeF (NP_417321.2), *E. coli* fadA (YP_026272.1), *E. coli* fadI (NP_416844.1), *Ralstonia eutropha* bktB (AAC38322.1), *Pseudomonas* sp. Strain B13 catF (AAL02407.1), *E coli* paaj (NP_415915.1), *Pseudomonas putida* pcaF (AAA85138.1), *Rhodococcus opacus* pcaF (YP_002778248.1), *Streptomyces* sp. pcaF (AAD22035.1), *Ralstonia eutropha* phaA (AEI80291.1), *Clostridium acetobutylicum* thlA (AAC26023.1), and *Clostridium acetobutylicum* thlB (AAC26026.1).

41. The microorganism of claim 40, wherein said overexpressed 3-oxoacyl-[acyl-carrier-protein] reductase, overexpressed 3-hydroxyacyl-[acyl-carrier-protein] dehydratase, and overexpressed enoyl-[acyl-carrier-protein] reductase are able to act on omega-aminated substrates and encoded by genes selected from the group consisting of *E. coli* fabA, *E. coli* fabG, *E. coli* fabI, *Enterococcus faecalis* fabK, *Bacillus subtilis* fabL, *Vibrio cholerae* fabV and *E. coli* fabZ.

42. The microorganism of claim 41, wherein said overexpressed termination pathways are able to act on omega-aminated substrates and encoded by genes selected from the group consisting of *E. coli* tesA, *E. coli* tesB, *E. coli* yciA, *E. coli* fadM, *E. coli* ydiI, *E. coli* ybgC, *E. coli* paaI, *E. coli* ybdB, *A. Borkumensis* tesB, *A. thaliana* ACH2, *M. musculus* acot8 *S. cerevisiae* PTE1, *E. coli* atoD, *Clostridium kluyveri* cat2, *Clostridium acetobutylicum* ctfB, *E. coli* ydiF, *Clostridium acetobutylicum* ptb/buk, *Enterococcus faecalis* ptb/buk, *Salmonella enterica* pduL/pduW, *Clostridium acetobutylicum* adhE2, *Arabidopsis thaliana* At3g11980, *Arabidopsis thaliana* At3g44560, *Arabidopsis thaliana* At3g56700, *Arabidopsis thaliana* At5g22500, *Arabidopsis thaliana* CER4, *Marinobacter aquaeolei* VT8 maqu2507, *Acinetobacter calcoaceticus* acr 1, *Acinetobacter* sp Strain M-1 acrM, *Clostridium beijerinckii* ald, *E. coli* eutE, *Salmonella enterica* eutE, *E. coli* mhpF, *E. coli* betA, *E. coli* eutG, *E. coli* fucO, *E. coli* ucpA, *E. coli* ybbO, *E. coli* ybdH, *E, coli* yiaH, *Synechococcus elongatus* PCC7942 orf1593, *Nostoc punctiforme* PCC73102 npun_R1711, *Prochlorococcus marinus* MIT9313 pmt1231, *Mus musculus* abaT and *E. coli* gabT.

43. The microorganism of claim 16 wherein said reduced expression of fermentation enzymes are ΔadhE, (Δpta or ΔackA or ΔackApta), ΔpoxB, ΔldhA, and ΔfrdA and less acetate, lactate, ethanol and succinate are thereby produced.

44. The microorganism of claim 1, comprising one or more termination enzymes from Table C.

45. A method of making a desired product, comprising growing the microorganism of claim 1 for a time sufficient to make a product by reverse beta oxidation, and then producing said product.

* * * * *